US007667002B2

(12) United States Patent
Mishra

(10) Patent No.: US 7,667,002 B2

(45) Date of Patent: Feb. 23, 2010

(54) PEPTIDES AND PROTEINS FOR EARLY LIVER DEVELOPMENT AND ANTIBODIES THERETO

(76) Inventor: Lopa Mishra, 6910 Oakridge Ave., Bethesda, MD (US) 20815

( * ) Notice: Subject to any disclaimer, the term of this patent is extended or adjusted under 35 U.S.C. 154(b) by 137 days.

(21) Appl. No.: 11/783,459

(22) Filed: Apr. 10, 2007

(65) Prior Publication Data

US 2008/0287353 A1 Nov. 20, 2008

Related U.S. Application Data

(60) Division of application No. 10/695,994, filed on Oct. 30, 2003, now Pat. No. 7,202,347, which is a division of application No. 09/431,184, filed on Nov. 1, 1999, now Pat. No. 6,642,362, which is a continuation-in-part of application No. PCT/US98/08656, filed on Apr. 30, 1998, which is a continuation-in-part of application No. 08/841,349, filed on Apr. 30, 1997, now Pat. No. 5,955,594.

(51) Int. Cl.
*C07K 14/475* (2006.01)

(52) U.S. Cl. ............ 530/387.9; 530/387.1; 530/388.23

(58) Field of Classification Search ....................... None
See application file for complete search history.

(56) References Cited

OTHER PUBLICATIONS

Mishra et al., "Characterization of differentially expressed mRNAs in mouse embryonic liver", vol. 16, No. 4, Part 2, 1992, p. 186A.

Mishra et al., "Characterization of a novel stage-specific gene (SC 32) isolated from developing liver", Gastroenterology, vol. 104, No. 4, Suppl., 1993; p. A956.

Bankert et al., "Identification of two novel stage specific genes from developing liver", FASEB Journal, vol. 7, No. 3-4, 1993, p. A821.

Cheroutre et al., "Analysis of MHC Class 23-27 I Gene Expression in Adult Bone Marrow . . . ", Journal of Immunology, The Williams and Wilkins Co., vol. 146, No. 10, May 15, 1991, pp. 3263-3272.

Monga et al., "Liv 88, a novel goliath-related gene encoding a RING-H2 motif in hepatocyte growth and differentiation", Gastroenterology, vol. 112, No. 4 Supp., Apr. 1997, p. A1336.

Payne et al., "The multiple murine 26, 27 3-beta-hydroxysteroid dehydrogenase isoform: structure, function and tissue- and developmentally specific expression", Steroids, vol. 62, No. 1, Jan. 1997, pp. 169-175.

Duncan et al., "Expression of transcription factor HNF-4 in the extraembryonic endoderm, gut and nephrogenic tissue . . . ", Proceedings of the National Academy of Sciences of the United States, vol. 91, No. 16, 1994, pp. 7598-7602.

Harrison et al., "Isolation of novel tissue-specific genes from cdna libraries representing the individual tissue . . . " Development, Company of Biologists, vol. 121, No. 8, 1995, pp. 2479-2489.

Schweinfest et al., "Subtraction hybridization cDNA libraries from colon carcinoma and hepatic cancer", Gene Analysis Techniques, Elsevier Science Publishers, vol. 7, 1990, pp. 64-70.

Bankert et al., "Mus musculus clone Sc developing liver stage specific mRNA", Database EMBL (online), Accession No. U06945, Feb. 5, 1998.

Cai Tao et al., "Molecular cloning and expression of mouse ITIH-4: Encodes a scaffolding protein in liver formation", Gastroenterology, vol. 114, No. 4, Part 2, Apr. 15, 1998, p. A1218.

Mishra et al., "Identification of elf1, a beta-spectrin, in early mouse liver development", International Journal of Developmental Biology, vol. 42, No. 2, Mar. 1998, pp. 221-224.

Cai Tao et al., "Identification of mouse itih-4 encoding a glycoprotein with two EF-hand motifs from early embryonic liver", Biochimica et Biophysica Acta, vol. 1398, No. 1, May 29, 1998, pp. 32-37.

*Primary Examiner*—Prema Mertz
(74) *Attorney, Agent, or Firm*—B. Aaron Schulman; Stites & Harbison PLLC

(57) ABSTRACT

Early developing stage-specific liver proteins and the genes coding for them that have been isolated and sequenced are provided, and these genes and proteins can be utilized to diagnose and/or treat a wide variety of liver disorders and other ailments. Since the early developing liver proteins of the invention arise during embryogenesis when the liver and other organs are in transition from an undifferentiated state to a differentiated one, these proteins are involved in tissue differentiation and thus can be utilized in methods of diagnosing and treating a variety of liver diseases and other disorders including those relating to oncogenesis and tissue repair. Antibodies recognizing early developing liver proteins and peptides are also provided.

1 Claim, 30 Drawing Sheets

*FIG. 1A*

1 TCGGGAAANGATTGATTTGGCCNCCTCGGNAAGGCNTTTTATTTTGCNNCAAGGAGGGCCCGGGGGGTTTCCAACCN[illegible]ATAAAATT 87

88 TTTTTCGGATCCCGGGGGTTTCCTCAGGGAGTTGGGGAATTTTACTTTGAAAGCAGATNTTTCNGAGNTCCGGGTAGCTNTCCAAT 174

175 AACTNTTTGTCATCATTGCCAGACGGCAGATCAAGGATGCCTTCGGTTTACCCGTGCTGTTCAGAGAACGGCTTTTGGAAGATTGAT 261

262 TTTAAGTTATTTAACAGTCACAGACAGGTGTCATNTNTGGAGAATAGAGGCAAGTCCGCGGTGAGGGATGAAGCAGGAGAGATAGGG 348

349 GAAGGCAGACAGGACTGCTGGGCCAAGGAAGCTGTGCTGATTTGAGCACAGTGGGAATTCACGTACGCAATTTCAAAGGCTTTAGTG 435

436 GTAAATTCTGAAGCTCAGATGCAGGCAAGACCCAAGAGGATAGTGTACACAGAGAGAAGAGGGTCNTCAGGATCGTGCGTAGAGTGG 522

523 AGAGAGCCCCAAAGGCAGGAGGGAAGAGCCTCAGTGGATTACTTAGGGATGAGGGAGAGAAGAAAAAAGGTTCTTGCAAGGTGTGGG 609

610 GTCTTCCAAATTCAGGAGTTCACTGAACTATAGAGAAGGTGTAGCGGGTGAAAGGGGCCATGTGATGAGGATGGCAAGCAAGGCTGT 696

697 GGCGCAGATGACGAGATGCCTGGGTCGGGAGGTCAGGGGAGACCCAGGATTGGGGTCACCTGTGTCTGCGCAGAGGGGAAGCCACCC 783

784 TGCAACTGGCCCAGCACTGAGTCCAGAGGAAAATGAGGCAGAGGACAAACCAGAGCTTCGGAGACTAAGTGCAGGTAGGGCGCGGGC 870

871 GGAGCGTGAGGAGGGCAGCGGACCACGCGAGAGGCNTCGAAGGCCACCGGACCCGCGTCCGAGAGTCTGAGGGCCCTGCCCACACCT 957

958 GCGRGGCCCCCTCCCCAGAGGCCACACTCCAAGGCCACCCTAGAACCCGTCTGTCTGCTCAAGCCCTTGCAAAAGACGTCTGCGCAG 1044

1045 AGGGGGCGTGGCAGGCGTGCTGTCACTCACGGCCTGTTAGCCAATCCACGAGTGCGCCCCTCCCCGGAGAGGGTGCGCGGAGGGCCC 1131

1132 GCCCCCGCCGCCACCGCGGGTGTGAGGAGGCCAGGCTGGCGCGGCTCCCTCCGCCCGGCAGCCTTGCCAGGTAACCGGGTTCGGCGG 1218

1219 GAGGGCTGGGGGTCGCGCAGCCCCCTCGCTCCCTGGGAGGCGTGCACACTGCCGCGGCGGGTCCCGTGTGGCCGGAGGCCCGTGCG 1305

1306 CGCGTCGGACCGACGGGCCGCAGCCTGTGGGCGGGGTTGCGTGCGTGACGGGCGGCCGTGCCCCGCGTTGTGTCAGGCCTGCGCGGG 1392

1393 GAAAGCTCGGCCGAACCGAGGTGTCCAGGTCCGCCCGCTGCGGCCTGCCCCGGGTTGCGGGGCGCAGGCGCGGCGGTGGGCGGGGGT 1479

1480 CGTCCCCAGGAGCGTCTTTGTTCCCGGCGCGCTGAGGGCGGAGCCTCACCCCGCCCCGCCCCCGCGCTCAGTCCCCGCCCCGCGTCC 1566

1567 GCCCGCAGGAGCTGCCACCGGGTCCCGCTGGCCTCCCCGGCCGCCGCCACCGCCTCCGCCTCCGCCGCTCCGGGCCCGCCGGCTTGC 1653

1654 GTCGCCGAGGTCGCTGCAGCATGGCGNGCGTCGCGACCCCCTGCGCCAACGGCTGCGGGCCTGGCGCACCCTCCGAAGCCGAGGTGC 1740

M A ? V A T P C A N G C G P G A P S E A E V L

1741 TGCACCTCTGCCGCAGCCTCGAGGTGGGCACCGTCATGACTTTGTTCTACTCCAAGAAGTCGCAGCGGCCAGAACGGAAGANCTTCC 1827

H L C R S L E V G T V M T L F Y S K K S Q R P E R K ? F Q

1828 AGGTCAAGTTGGAGACGCGCCAGATCACATGGAGCCGCGGCGCGGACAAAATCGAGGGGTCCAGTAAGTGCGCCCCACTCCGGCCTG 1914

V K L E T R Q I T W S R G A D K I E G S S K C A P L R P A

1915 CCTCGCGCCTGCCCGCCTCCCAAACACTTGGGCAAACTTTCGGGCCTCGCGCCTGGCGCCCCGTCTCCGCCCAGTCCCTGGTGGTCA 2001

S R L P A S Q T L G Q T F G P R A W R P V S A Q S L V V T

2002 CTCTGGGGCGGGTGGAGGGGGGCATCCGGGTCTTGGATCACCTGATAGGACACCCCCTCCCCCAGTAGGGGGGGAGTGTTCCAGGCA 2088

L G R V E G G I R V L D H L I G H P L P Q *

2089 CTTTGCCCTGAGGCCTAAGAGTCCTCACTGGTTGGACAAGTGGAGTGGGATTCCGGCCCTTAGCATCGGGCGGCTGTCAGTGGCTGT 2175

2176 GAGGGGAAGCCAAGACAGGGACCCCCTCATCCAACCTGAGAACCTGGGGAACCGACAAGATCTTCCTGCCCACTGCCATTTCTCCAG 2262

2263 AGTGTGCTGTCTGTGAAAACTCCTAAGAGCTCCGGGATGGGCTTATTGGCGCAAGAACCTTTGGAATCCTCATGTAGAACTTAGGCA 2349

2350 GATGTTGGGGTAGGGCTGGTGGTGAAGCAGAGCCCTACTCATCTCCCCTCTTCTTTGGGAGGATGGGGTATGAAAGCTAAAACCGTG 2436

2437 ACTGCTTCCCCCTCCCATGTCCCGTGGATGGGTTTTTTTTTTTTTTTTTTGCCCCAGATCTGAATTTTGGAGGTCCATGGTGCTA 2523

2524 GGCAGCCATCCAAAGCTAGAGCCATGGCTCCTTTGCCCTTGCAGCATATAACAAGGAGCTTGCATTCAGAAAGGTTCCCTGGCCTTG 2610

FIG. 1B

2611 GGTTTTGGGGTCCAGCCCTTTGTGTTGGATGTTCTCGTGACCACAGGGTAGCCCANAGTTGCTCCTCTGGTTTCCTGTCGTACCCTT 2697
2698 CCCAAACCTGAGTGTGGTGGGTTTACACACAAGTCTCTGGTGGGAGAAGTAAGTCAGGAGTTTTGAGAAACCTCGGCTCTTTGTGAT 2784
2785 AGTCATTTTCCTCGGTGTGAGGCAGGATGAGGAGTCTTTGCAACTCCAGGCTTTGAGATGTTTCTTACAAGAACCCCCAAAGAGTCT 2871
2872 ATGGTTGAAGGGACCTAGCCTAAGAGCCAGGTCTGTGTTAGAGAAGGGGGGGTGGTGTCAGGAAGTAACAACGGCGAGAAGGTCCCA 2958
2959 CAGATCTTCCTGGGGATGGTGTACATGTGTGTCGATGGGTGAGGAGATGAGGAGGAAGGAAGGTTTCTGTGGTAAGACAGCCATCCT 3045
3046 CAACTACAAACTTCAGGTCTGACAGAATTGGCCCTTAACCATCACCAGTGCCCATCAGCCCTGGCCTCCGCTGGAAGAACATTTCAG 3132
3133 TGATTTTCAGTGTTGGGGGATGGAACTGCAGACAGTTCCGGTAGTCCTGAGACATCACTCAGACATCAGGTTGCAGGCATGGCATTT 3219
3220 TACGTTTGTAGTATTTCCTGTGTTTAAGTGGTGGCATTAGTTCCCCGGTAGCTAGCTCTTGGTAACAGCTGCACTGTAAACCGTGTG 3306
3307 TGTAGCCCAGTAGTGGAAGATAGCTATGGTATTTGAAGCCAGTGTGTTAGCTGTACGTCACCCAGCCAGGTGCTTTCCCTCTCGGAG 3393
3394 CCTCGGTTCCTCTGTAAGTTAGCAGAAGTATATTTACTATAAATGGTCACTTTTGGAAGTGAGATAGTTGGTGTAAAGTAAGCAAAC 3480
3481 TAAATATGTAATAGATGCGAGCAGAGACGTTACAGAAGTTTAAGAACCAGTTATTAGTAGCAGTAGCTATGGTAGATGCTTGTCCTC 3567
3568 CTAGACCCTGGGATGGGGCTTCTGAGGGAGGTCTAATGTGGCTGTTAGAAAAAGAAAGGGCTCTGAGGGAGGAGGGCCGAGAGAGGG 3654
3655 TCCCGTTCTCCTTAATTGCATTACCCAGGATAAAAGAGGAAACTCTTGTTTTGCCGTACATCGTTTACCCTTCTGTTCACCTGTCAT 3741
3742 GTAAGATGAGTTTCTATGTTTGGAATTTTGTACATTGGATGCCATTGTGAGTTGGGGCCTGGACAGAAAGAAGGGACTTAGAGACAG 3828
3829 AACCATCCAGTCCGTTTTGTCTCACTTGGGTCTTTGAGGATGGGTGGCAGGAATACAGAGGACGTCACCTTTCCAGACCCAGAAAAG 3915
3916 TCACCCAGAGATATGCATGTTTTCATTGGGCCCGACCCTGTGATTTTTGGGGTCCAGAATGAAGGCTGCAGACTAGCCTGTGTGGAC 4002
4003 TTCATACCTTGTAAATGGAGCCCACCACCGAAGCCCTGCCCCACTTCTGCTGGAATGCACCTCACTGCCTTTGTGGGTTCCCAAACC 4089
4090 TGCAGCCTCCTGCAGATTGTGAAAAGGCTTGAGTTGCCAGCTCCCTCCCTACTGTCTGGTCTCTTGTTCAGATGCCTCAGGTATTTG 4176
4177 ACTTTTTGCTGATAACCTTATCCCTACCTGAAGCCAGGCCAGAGAGAAAGACTGCCGCTGTCTGCCCTCAGGGTGCTCACGGAACAC 4263
4264 AACGACAGGCTGACTGCCATTTCCTAAATCTTGAGTTCTCTCACTGTGACACCTGTGAAACTAGTTAGCACCTTCTGATGTCTAAGG 4350
4351 CAGCGGTCTACTTGAGAAGTGCTTTGGTGCTGTTTGGTTGTGTGACTGAAGTCAGGCTGGTGTCTGGCATTTATGTTGCAGAATTTA 4437
4438 GTGAGTTAAAAGCAGCCATAGACTTCCTGCCCAGTGCTAAACAGACTTTTCACTCTGCTGCAGGCTAGTCCTCAGAGGACTCTGCTC 4524
4525 CCAGGTTGTGTTGGTGGTAGGCCTTGGTCTCCTGTTTTCTGTAGCCTTTGTTGCCCCTTGTGAAGAGAAACCTCCATGTTTAGGTGG 4611
4612 TATTTACAGGCAGAGACCTCCATCTTCATCAAAGACGCCTTCCTAGGCTTTCCATATGTAATGCCTGTAGTGAGATGGCTCAGACCT 4698
4699 ATTCTTCGTGAGGTTGTCCAGTTAAGGACCACTGTTGGCATAGTAGCTCCAGTAGAGACTCTAAAGCTATGTTGTTATTGTGGTGAG 4785
4786 GATTGCAGTACCAAGGGGCTGGCTCTGAGAGTAGGTCCGTGGCACCTAAGAATTGTCTGCACATGTCCCTCAAGGATTCCTTTTNGC 4872
4873 TGGCCCACAGTGAGAGAGCAGCAGAAAGCATGCGCCTGGATCTAAGAAAGGTTAATGAAACCATGGTACCTATGGGAGCTTTACAAC 4959
4960 CTGGGCTTCTGTCTCCGGTAGCCATTTCTAAAAGANATTATGAAATTGTGGTAGATTGAAAGATGTTCCTTACTATTCCTTTACATC 5046
5047 CTGAGGATCACGAAAGATTTGCTTTCAGTATTCCTACTATTAATTTTAAAGAACCTATGAAAAGATATCAATGGACAGTTCTTCCAC 5133
5134 AAGGCATGGCTAATAATCCTACCTTATGTCAAANTTGTGGCACAACCATTCACCTGTGAGACACAATGACTATGACTACTCNTCNTG 5220
5221 ATGATGATGANGATGATGAGATGATGATGATGATGATGATGACACACAMGATAGAGATGATTCTAANGCGGAAANATCCCGACTGCT 5307
5308 TTNCTTAAAATTACCNNCCTNCGAAAAGATTAAACCCGAAAGGTCACCGATCTATATTTNGTTTAANTNATACCGTTTCCCAAAATT 5394
5395 TTNCGGACCTNAANTTTNATCAATTTTGTNTATGNTCCCC 5434

FIG. 2A

CCTGCGTCCTTCCTCCTTTTCCTCCTTCCCTCCTCCCTCCCGGGTAATTTATTTCTAGCTTCCAGGCAAGGGCCACACAAGGAAGGAAATCCACAGGGGATTAGATGCCGGGGTGGTAAC 120

TCCACCAGGCTAGGTTGGACTCTGCAGCCAACTTCCTATCAGATCACCCTGCACCTATTTCCGACCCGACCGGAATGCGACTGGCTTGAGGTCCAGCCCTTTCGCCTGGGCGGAGCAGA 240

GCCGCGGAAGCTGCTTGGAGTTGGATGGGGTAGGAAGGGGCTGGAGCGGGAATCCTACGATGCAACTGGCCTGGGCCTAAGGTTGGGCA[illegible]AATGGAGTTGCAGAGGACATCCAGCGTTT 360

M E L Q R T S S V S 10

CAGGGCCGCTGTCGCCGGCCTACACCGGGCAGGTGCCTTACAACTACAACCAACTGGAGGGAAGATTCAAACAGCTCCAAGATGAGCGTGAAGCTGTACAGAAGAAGACCTTCACCAAGI 480

G P L S P A Y T G Q V P Y N Y N Q L E G R F K Q L Q D E R E A V Q K K T F T K W 50

GGGTCAATTCCCACCTTGCAAGAGTGTCCTGCCGAATCACAGACCTGTACACGGACCTTCGAGATGGACGGATGCTCATCAAGCTACTGGAGGTCCTCTCTGGAGAGAGGCTGCCTAAAC 600

V N S H L A R V S C R I T D L Y T D L R D G R M L I K L L E V L S G E R L P K P 90

CCACTAAGGGACGGATGCGGATCCACTGTCTGGAGAATGTCGACAAGGCTCTTCAATTCCTGAAAGAGCAGAGAGTCCATCTTGAGAACATGGGCTCCCATGACATTGTGGATGGAAACC 720

T K G R M R I H C L E N V D K A L Q F L K E Q R V H L E N M G S H D I V D G N H 130

ACCGGCTGACCCTCGGCCTCATCTGGACAATTATTCTGCGCTTCCAGATCCAGGATATTAGTGTGGAGACTGAAGATAACAAAGAGAAAAAGTCTGCTAAGGATGCATTGCTGCTGTGGT 840

R L T L G L I W T I I L R F Q I Q D I S V E T E D M K E K K S A K D A L L L W C 170

GCCAGATGAAGACAGCTGGGTACCCCAATGTCAACATTCACAATTTCACCACTAGCTGGAGGGATGGCATGGCCTTCAATGCACTGATACATAAACATCGGCCTGACCTGATAGATTTTG 960

G M K T A G Y P N V N I H N F T T S W R D G M A F M A L I H K H R P D L I D F D 210

ATAAACTGAAGAAATCTAATGCACACTACAATCTGCAGAATGCATTTAACCTGGCAGAGCAGCACCTTGGCCTCACTAAACTGTTAGACCCTGAAGATATCAGTGTGGACCACCCTGATG 1080

K L K K S N A H Y N L Q N A F N L A E Q H L G L T K L L D P E D I S V D H P D E 250

AGAAGTCTATCATCACATACGTGGTGACTTACTACCACTACTTCTCCAAGATGAAGGCCTTGGCTGTCGAAGGAAAGCGCATTGGAAAGGTGCTTGATAATGCTATAGAAACAGAGAAAA 1200

K S I I T Y V V T Y Y H Y F S K M K A L A V E G K R I G K V L D N A I E T E K M 290

TGATTGAGAAGTACGAGACACTTGCTTCTGACCTTCTGGAGTGGATTGAACAAACCATCATCATCCTAAACAACCGCAAATTTGCTAATTCACTGGTTGGGGTCCAACAGCAGCTCCAAG 1320

I E K Y E T L A S D L L E W I E Q T I I I L N N R K F A N S L V G V Q Q Q L Q A 330

CATTCAACACGTACCGCACAGTGGAGAAACCACCTAAGTTTACTGAGAAGGGGAATTTGGAGGTGCTCCTTTTCGCGATTCAGAGCAAGATGCGAGCGAATAATCAGAAGGTCTACATGC 1440

F N T Y R T V E K P P K F T E K G N L E V L L F A I Q S K M R A N N Q K V Y M P 370

CCCGCGAGGGGAAGCTCATCTCTGACATCAACAAGGCCTGGGAAAGACTGGAAAAAGCAGAACATGAGAGAGAACTGGCTCTGCGGAATGAGCTCATACGGCAGGAAAAACTGGAACAAC 1560

R E G K L I S D I N K A W E R L E K A E H E R E L E L R N E L I R Q E K L E Q L 410

TCGCCCGAAGATTTGATCGCAAGGCAGCTATGAGGGAGACATGGCTGAGTGAAAACCAGCGTCTTGTGTCTCAGGACAACTTTGGATTTGACCTTCCCGCTGTTGAGGCTGCTACCAAAA 1680

```
AACACGAGGCCATTGAGACAGACATCGCTGCATATGAAGAACGAGTTCAGGCCGTGGTGGCTGTGGCCAGGGAACTTGAAGCCGAGAACTACCATGACATCAAGCGCATCACAGCGAGGA 1800
 H  E  A  I  E  T  D  I  A  A  Y  E  E  R  V  Q  A  V  V  A  V  A  R  E  L  E  A  E  N  Y  H  D  I  K  R  I  T  A  R  K  490
AGGACAATGTCATCCGGCTCTGGGAATACTTGCTGGAACTGCTCAGGGCCAGGAGGCAGCGTCTTGAGATGAACCTGGGATTGCAAAAGATATTCCAGGAAATGCTTTATATTATGGACT 1920
 D  N  V  I  R  L  W  E  Y  L  L  E  L  L  R  A  R  R  Q  R  L  E  M  N  L  G  L  Q  K  I  F  Q  E  M  L  Y  I  M  D  W  530
GGATGGATGAAATGAAGGTGCTATTGCTGTCTCAAGACTATGGCAAACACTTACTTGGTGTTGAAGACCTGTTACAGAAGCATGCCCTGGTTGAAGCAGACATTGCAATCCAAGCAGAGC 2040
 M  D  E  M  K  V  L [L] L  S  Q  D  Y  G  K  H  L  L  G  V  E  D  L  L  Q  K  H [A] L  V  E  A  D  I [A] I  Q  A  E  R  570
GTGTAAGAGGTGTGAATGCCTCTGCCCAGAAGTTTGCAACAGATGGGGAAGGCTACAAGCCATGTGACCCCCAGGTAATTCGAGACCGTGTTGCCCACATGGAGTTCTGCTATCAAGAGC 2160
 U  R  G  V  N  A  S  A  Q  K  F  A  T  D  G  E  G  Y  K  P  C  D  P  Q  V  I  R  D  R  V  A  H  M  E  F  C  Y  Q  E  L  610
TTTGTCAGCTGGCTGCCGAGCGTAGGGCTCGCCTGGAAGAGTCCCGTCGCCTCTGGAAGTTCTTCTGGGAGATGGCAGAAGAGGAAGGCTGGATACGAGAGAAGGAAAAGATCCTGTCCT 2280
 C  Q  L  A  A  E  R  R  A  R  L  E  E  S  R  R  L  W  K  F  F  W  E  M  A  E  E  E  G  W  I  R  E  K  E  K  I  L  S  S  650
CTGATGATTACGGGAAAGACTTGACCAGTGTCATGCGCCTGCTGAGCAAGCACCGGGCATTTGAGGATGAGATGAGTGGCCGTAGTGGCCATTTTGAGCAGGCCATTAAAGAAGGTGAAG 2400
 D  D  Y  G  K  D  L  T  S  V  M  R  L  L  S  K  H  R  A  F  E  D  E  M  S  G  R  S  G  H  F  E  Q  A  I  K  E  G  E  D  690
ACATGATTGCAGAGGAACACTTTGGATCGGAAAAGATCCGTGAGAGAATCATTTATATCCGGGAGCAGTGGGCCAACCTGGAACAGCTCTCAGCCATTAGGAAGAAGCGCCTAGAGGAAG 2520
 M  I  A  E  E  H  R  G  S  E  K  I  R  E  R  I  I  Y  I  R  E  Q  W  A  N  L  E  Q  L  S  A  I  R [K] K  R  L  E  E  E  730
CCTCATTACTGCACCAGTTCCAGGCTGATGCTGATGATATTGATGCTTGGATGTTAGATATACTCAAGATTGTCTCCAGCAATGATGTGGGCCATGATGAGTACTCCACGCAGTCTCTGG 2640
 S  L  L  H  Q  F  Q  A  D  A  D  D  I  D  A  W  M  L  D  I  L  K  I  V  S  S [N] D  V  G  H  D  E  Y  S  T  Q  S  L  V  770
TCAAGAAGCATAAAGATGTAGCAGAAGAGATCACCAACTGCAGGCCCACTATTGACACACTGCATGAGCAAGCCAGTGCCCTTCCACAAGCACATGCAGAGTCTCCAGATGTGAAGGGCC 2760
 K  K  H  K  D  V  A  E  E  I [T] N [O] R  P  T [I] D  T  L  H  E  Q  A  S  A  L  P  Q [A] H  A  E  S  P  D  V [K] G  R  810
GGCTGGCAGGAATTGAGGAGCGCTGCAAGGAGATGGCAGAGTTAACACGGCTAAGGAAGCAGGCTCTGCAGGACACCCTGGCCCTGTACAAGATGTTCAGTGAGGCTGATGCCTGTGAGC 2880
 L [A] G  I  E  E  R [C] K  E [M] A  E  L  T  R  L  R  K  Q  A  L [Q] D  T  L  A  L  Y  K  M  F  S  E  A  D  A  C  E  L  850
TCTGGATTGACGAGAAGGAGCAGTGGCTCAACAACATGCAGATCCCAGAGAAGCTGGAGGACCTGGAAGTCATCCAGCACAGATTTGAGAGCCTAGAACCAGAAATGAACAACCAGGCTT 3000
 W  I  D  E  K  E  Q  W  L  N  N  M  Q  I  P  E  K  L  E  D  L  E  V  I  Q  H  R  F  E  S  L  E  P  E  M  N  N  Q  A  S  890
CCCGGGTTGCTGTGGTGAACCAGATTGCACGGCAGCTGATGCACAATGGCCACCCCAGTGAAAAGGAAATCAGAGCTCAGCAAGACAAACTCAACACGAGGTGGAGTCAGTTCAGAGAAC 3120
 R  V  A  V  V  N  Q  I  A  R  Q  L  M  H [N] G  H  P  S  E  K  E  I [R] A  Q  Q  D  K  L  N  T  R  W  S  Q  F  R  E  L  930
TGGTGGACAGGAAAAAGGATGCTCTTCTGTCTGCCCTGAGCATCCAGAACTACCACCTCGAGTGCAATGAAACCAAATCCTGCATCCGGGAGAAGACCAAGGTCATCGAGTCTACCCAAG 3240
 V  D  R  J  J  D  A  K  K  S  A  K  S  U  Q  N  Y  H  L  E  C  N  E  T  K  S  C  I  R  E  K  T  K  V  I  E  S  T  Q  D  970
```

FIG. 2C

```
ACCTTGGCAATGACCTGGCAGGTGTCATGGCCCTGCAGTGCAAGCTGACTGGCATGGAACGAGACTTGGTAGCCATTGAGGCGAAGCTGAGTGACCTGCAGAAAGAAGCTGAGAAGCTGG 3360
 L G N D L A G V M A L Q C X L T G M E R D L V A I E A K L S D L Q K E A A K L E 1010
AGTCCGAGCACCCTGACCAGGCTCAAGCTATCCTGTCTCGGCTGGCCGAGATCAGTGATGTGTGGGAGGAAATGAAGACAACCCTGAAGAACCGAGAGGCCTCCCTGGGAGAGGCCAGCA 3480
 S E H P D Q A Q A I L S R L A E I S D V W E E M K T T L K N R E A S L G E A S K 1050
AGCTGCAGCAGTTTCTGCGGGACTTGGACGACTTCCAGTCTTGGCTCTCCAGGACCCAGACTGCTATCGCCTCAGAGGACATGCCCAATACCCTCACTGAGGCAGAGAAGCTTCTCACAC 3600
 L Q Q F L R D L D D F Q S W L S R T Q T A I A S E D M P N T L T E A E K L L T Q 1090
AGCACGAGAATATCAAAAATGAGATCGACAATTATGAGGAAGACTACCAGAAGATGCGGGACATGGGCGAGATGGTCACCCAGGGGCAGACTGATGCCCAGTATATGTTTCTGCGGCAGC 3720
 H E N I K N E I D N Y E E D Y Q K M R D M G E M V T Q G Q T D A Q Y M F L R Q R 1130
GGCTGCAGGCCTTAGACACTGGCTGGAATGAGCTCCACAAAATGTGGGAGAACAGGCAAAACCTCCTCTCCCAGTCCCATGCCTACCAGCAGTTCCTTAGGGACACCAAACAAGCTGAAG 3840
 L Q A L D T G W N E L H K M W E N R Q N L L S Q S H A Y Q Q F L R D T K Q A E A 1170
CTTTTCTTAATAACCAGGAGTATGTTTTGGCTCATACTGAAATGCCCACCACCCTGGAAGGAGCTGAAGCAGCCATTAAAAAGCAGGAGGACTTCATGACCACCATGGATGCCAACGAGG 3960
 F L N N Q E Y V L A H T E M P T T L E G A E A A I K K Q E D F M T T M D A N E E 1210
AGAAGATCAATGCTGTTGTGGAGACTGGCCGAAGACTGGTGAGCGATGGGAACATCAACTCCGACCGCATCCAGGAGAAGGTGGACTCTATTGACGACAGACACAGGAAGAATCGAGAAG 4080
 K I N A V V E T G R R L V S D G N I N S D R I Q E K V D S I D D R H R K N R E A 1250
CAGCCAGTGAACTTCTGATGAGGTTAAAGGACAACCGTGATCTACAGAAGTTCCTGCAAGATTGTCAAGAGCTGTCCCTCTGGATCAATGAAAAGATGCTTACAGCTCAAGACATGTCTT 4200
 A S E L L M R L K D N R D L Q K F L Q D C Q E L S L W I N E K M L T A Q D M S Y 1290
ATGATGAAGCCAGAAATCTGCACAGTAAATGGTTAAAGCATCAAGCATTTATGGCGGAACTTGCATCCAACAAAGAATGGCTTGACAAAATTGAGAAGGAAGGAATGCAGCTTATTTCAG 4320
 D E A R N L H S K W L K H Q A F M A E L A S N K E W L D K I E K E G M Q L I S E 1330
AAAAGCCAGAAACAGAAGCTGTGGTAAAGGAAAAACTCACTGGTTTACATAAAATGTGGGAAGTCCTTGAATCCACAACCCAGACCAAGGCCCAGCGGCTCTTTGATGCAAATAAGGCTG 4440
 K P E T E A V V K E K L T G L H K M W E V L E S T T W T K A W R L F D A N K A E 1370
AGCTTTTCACACAAAGCTGCGCAGATCTTGACAAATGGCTACATGGCCTGGAGAGCCAGATTCAATCTGACGACTATGGCAAAGACCTTATTAGTGTCAATATTCTTCTGAAAAAGCAAC 4560
 L F T Q S C A D L D K W L H G L E S O T W S D D Y G K D L T S O N T L L K K Q Q 1410
AGATGCTGGAGAATCAGATGGAAGTTCGGAAGAAAGAGATCGAGGAACTGCAGAGCCAAGCCCAGGCGCTGAGTCAGGAGGGGAAGAGCACAGATGAGGTGGACAGCAAACGCCTTACTG 4680
 M L E N Q M E O R K K E I E E L Q S Q A Q A L S Q E G K S T D E V D S K R L T V 1450
TGCAGACCAAGTTCATGGAGCTTCTGGAGCCCTTGAGTGAGAGGAAGCATAACCTGTTAGCTTCCAAGGAGATCCATCAGTTCAACAGGGATGTGGAGGACGAAATCCTATGGGTTGGCG 4800
 Q T K F M E L L E P L S E R K H N L L A S K E I H Q F N R D V E D E I L W V G F 1490
```

FIG. 2D

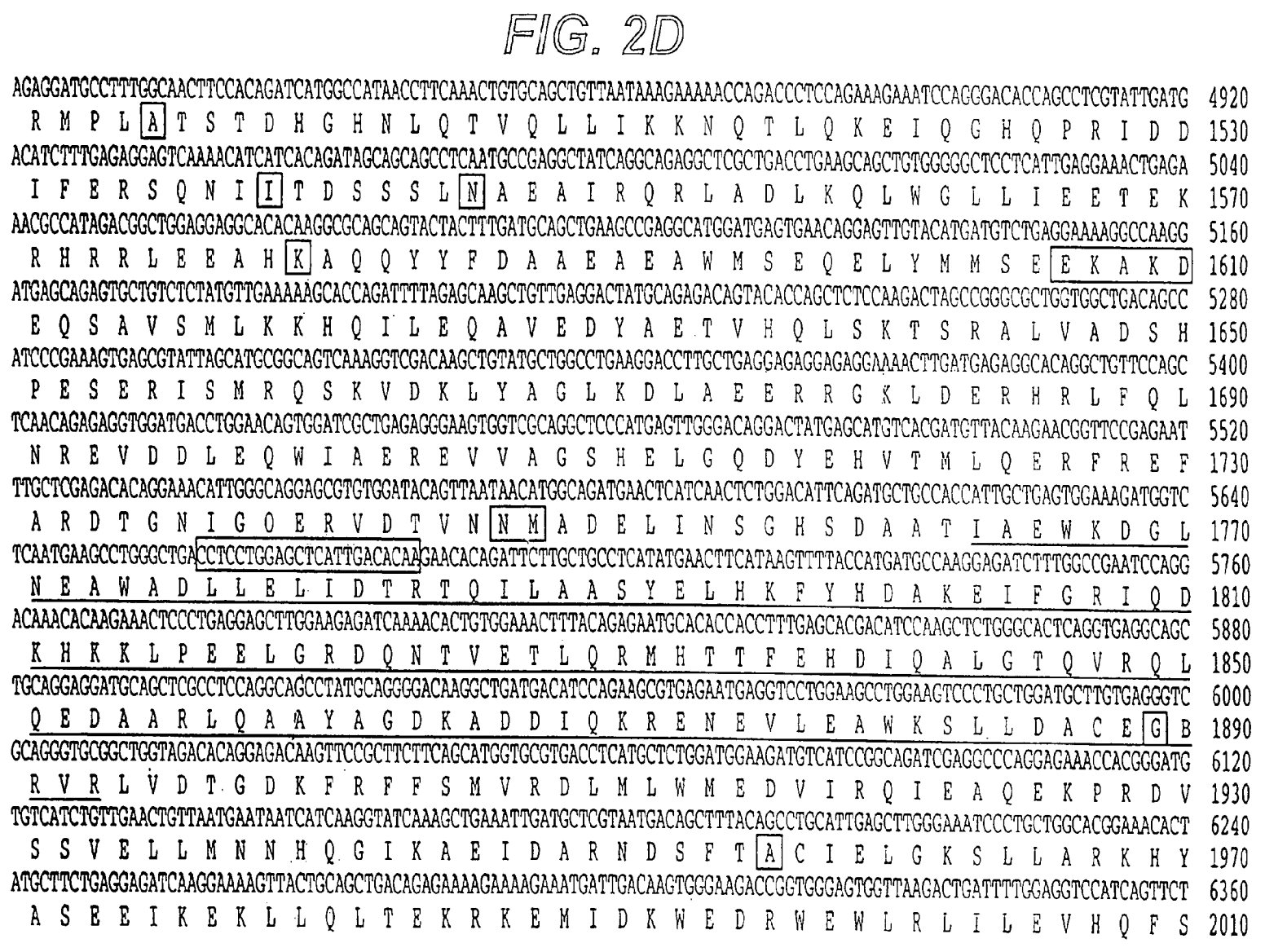

```
AGAGGATGCCTTTGGCAACTTCCACAGATCATGGCCATAACCTTCAAACTGTGCAGCTGTTAATAAAGAAAAACCAGACCCTCCAGAAAGAAATCCAGGGACACCAGCCTCGTATTGATG 4920
 R  M  P  L [A] T  S  T  D  H  G  H  N  L  Q  T  V  Q  L  L  I  K  K  N  Q  T  L  Q  K  E  I  Q  G  H  Q  P  R  I  D  D 1530
ACATCTTTGAGAGGAGTCAAAACATCATCACAGATAGCAGCAGCCTCAATGCCGAGGCTATCAGGCAGAGGCTCGCTGACCTGAAGCAGCTGTGGGGGCTCCTCATTGAGGAAACTGAGA 5040
 I  F  E  R  S  Q  N  I [I] T  D  S  S  S  L [N] A  E  A  I  R  Q  R  L  A  D  L  K  Q  L  W  G  L  L  I  E  E  T  E  K 1570
AACGCCATAGACGGCTGGAGGAGGCACACAAGGCGCAGCAGTACTACTTTGATGCAGCTGAAGCCGAGGCATGGATGAGTGAACAGGAGTTGTACATGATGTCTGAGGAAAAGGCCAAGG 5160
 R  H  R  R  L  E  E  A  H [K] A  Q  Q  Y  Y  F  D  A  A  E  A  E  A  W  M  S  E  Q  E  L  Y  M  M  S  E [E  K  A  K  D] 1610
ATGAGCAGAGTGCTGTCTCTATGTTGAAAAAGCACCAGATTTTAGAGCAAGCTGTTGAGGACTATGCAGAGACAGTACACCAGCTCTCCAAGACTAGCCGGGCGCTGGTGGCTGACAGCC 5280
 E  Q  S  A  V  S  M  L  K  K  H  Q  I  L  E  Q  A  V  E  D  Y  A  E  T  V  H  Q  L  S  K  T  S  R  A  L  V  A  D  S  H 1650
ATCCCGAAAGTGAGCGTATTAGCATGCGGCAGTCAAAGGTCGACAAGCTGTATGCTGGCCTGAAGGACCTTGCTGAGGAGAGGAGAGGAAAACTTGATGAGAGGCACAGGCTGTTCCAGC 5400
 P  E  S  E  R  I  S  M  R  Q  S  K  V  D  K  L  Y  A  G  L  K  D  L  A  E  E  R  R  G  K  L  D  E  R  H  R  L  F  Q  L 1690
TCAACAGAGAGGTGGATGACCTGGAACAGTGGATCGCTGAGAGGGAAGTGGTCGCAGGCTCCCATGAGTTGGGACAGGACTATGAGCATGTCACGATGTTACAAGAACGGTTCCGAGAAT 5520
 N  R  E  V  D  D  L  E  Q  W  I  A  E  R  E  V  V  A  G  S  H  E  L  G  Q  D  Y  E  H  V  T  M  L  Q  E  R  F  R  E  F 1730
TTGCTCGAGACACAGGAAACATTGGGCAGGAGCGTGTGGATACAGTTAATAACATGGCAGATGAACTCATCAACTCTGGACATTCAGATGCTGCCACCATTGCTGAGTGGAAAGATGGTC 5640
 A  R  D  T  G  N  I  G  O  E  R  V  D  T  V  N [N  M] A  D  E  L  I  N  S  G  H  S  D  A  A  T  I  A  E  W  K  D  G  L 1770
TCAATGAAGCCTGGGCTGA[CCTCCTGGAGCTCATTGACACAA]GAACACAGATTCTTGCTGCCTCATATGAACTTCATAAGTTTTACCATGATGCCAAGGAGATCTTTGGCCGAATCCAGG 5760
 N  E  A  W  A  D  L  L  E  L  I  D  T  R  T  Q  I  L  A  A  S  Y  E  L  H  K  F  Y  H  D  A  K  E  I  F  G  R  I  Q  D 1810
ACAAACACAAGAAACTCCCTGAGGAGCTTGGAAGAGATCAAAACACTGTGGAAACTTTACAGAGAATGCACACCACCTTTGAGCACGACATCCAAGCTCTGGGCACTCAGGTGAGGCAGC 5880
 K  H  K  K  L  P  E  E  L  G  R  D  Q  N  T  V  E  T  L  Q  R  M  H  T  T  F  E  H  D  I  Q  A  L  G  T  Q  V  R  Q  L 1850
TGCAGGAGGATGCAGCTCGCCTCCAGGCAGCCTATGCAGGGGACAAGGCTGATGACATCCAGAAGCGTGAGAATGAGGTCCTGGAAGCCTGGAAGTCCCTGCTGGATGCTTGTGAGGGTC 6000
 Q  E  D  A  A  R  L  Q  A  A  Y  A  G  D  K  A  D  D  I  Q  K  R  E  N  E  V  L  E  A  W  K  S  L  L  D  A  C  E [G] B 1890
GCAGGGTGCGGCTGGTAGACACAGGAGACAAGTTCCGCTTCTTCAGCATGGTGCGTGACCTCATGCTCTGGATGGAAGATGTCATCCGGCAGATCGAGGCCCAGGAGAAACCACGGGATG 6120
 R  V  R  L  V  D  T  G  D  K  F  R  F  F  S  M  V  R  D  L  M  L  W  M  E  D  V  I  R  Q  I  E  A  Q  E  K  P  R  D  V 1930
TGTCATCTGTTGAACTGTTAATGAATAATCATCAAGGTATCAAAGCTGAAATTGATGCTCGTAATGACAGCTTTACAGCCTGCATTGAGCTTGGGAAATCCCTGCTGGCACGGAAACACT 6240
 S  S  V  E  L  L  M  N  N  H  Q  G  I  K  A  E  I  D  A  R  N  D  S  F  T [A] C  I  E  L  G  K  S  L  L  A  R  K  H  Y 1970
ATGCTTCTGAGGAGATCAAGGAAAAGTTACTGCAGCTGACAGAGAAAAGAAAAGAAATGATTGACAAGTGGGAAGACCGGTGGGAGTGGTTAAGACTGATTTTGGAGGTCCATCAGTTCT 6360
 A  S  E  E  I  K  E  K  L  L  Q  L  T  E  K  R  K  E  M  I  D  K  W  E  D  R  W  E  W  L  R  L  I  L  E  V  H  Q  F  S 2010
```

FIG. 2E

```
CAAGGGATGCCAGTGTGGCAGAGGCTTGGCTGCTTGGACAGGAACCATACCTATCCAGCCGTGAAATTGGCCAGAGTGTAGACGAAGTGGAGAAGCTTATTAAGCGCCATGAGGCHTTTG  6480
 R  D  A  S  V  A  E  A  W  L  L  G  Q  E  P  Y  L  S  S  R  E  I  G  Q  S  U  D  E  V  E  K  L  I  K  R  H  E  A  F  E  2050
AAAAGTCTGCAGCGACCTGGGATGAGAGATTCTCTGCTCTGGAAAGGCTGACAACGTTGGAGCTACTGGAAGTGCGCAGACAGCAAGAGGAAGAAGAAAGAAAGAGGCGGCCACCTTCTC  6600
 K  S  A  A  T  W  D  E  R  F  S  A  L  E  R  L  T  T  L  E  L  L  E  V  R  R  Q  Q  E  E  E  E  R  K  R  R  P  P  S  P  2090
CGGACCCAAACACGAAGGTTTCAGAGGAGGCTGAGTCCCAGCAATGGGATACTTCAAAAGGAGACCAAGTTTCCCAGAATGGTTTGCCGGCTGAGCAGGGATCTCCACGGGTTAGTTACC  6720
[D] P [N] T  K  V  S  E  E  A  E  S  Q  Q  W  D  T  S  K  G [D] Q  V  S  Q  M  G  L  P  A  E  Q  G  S  P  R [U  S  Y  R] 2130
GCTCTCAAACGTACCAAAACTACAAAAACTTTAATAGCAGACGGACAGCCAGTGACCATTCATGGTCTGGAATGTGAAGTTCACTACCATTTGTCAAGAACCACTCTGTCCACATCCTTT  6840
[S  Q  T  Y  Q  N  Y  K  N  F  N  S  R  R  T  A  S  D  H  S  W  S  G  M]                                                  2170
GACCTTTTGGCTTCCACGTCACCCAGAGTGTTAAAATTTTTACTTAATTCATAGCTGTCCTTGATTTCATATTTGTTTGCATTTAATTTATGTTTCTTTGGATCCTCATTGCCTCAAAGC  6960
AGCATACTTAATTTTTGTTTATTTATTGTGAGCTTTTTACTTTAAGATTTTACATGAGTAATCAAAATTAAATTATAGCATAATGAAATTAGACTCTTAACAGGTACGGCACACACAAGT  7080
TAATAGTACTCTGCTATAGGTGCTATGTTACTTACAAGTATTATTAACCTATTGGCTTCCATTGTATAGTAGTTAGTAACTATGAAAACTGGTTTGTAAGGAAGGAAACGTTTACTACTA  7200
AGGTTAGGCCTGCAGTTGCTCTGGAACATTCCATGGAGAATGCATTCATCAAACGGCCCGAAAGAAGCTACATTTTGTTGGGAAGCTGGATAAGTTTTAGGTGCAGGACCCCAAATGTTC  7320
TGAGACCTTTGGGGCCATTTATTACTTTGTACAAGCCCAATAATCCTCTCTTTTCTGCCAAGTCCTCAACCCAGAAATGTAGGCTTCTGTGCACCACACGGCACAGCCCACTGATTGCTG  7440
CCACCGGCTCTGTCTTGGTCAGTGTTACCACTGCCAGCACTCAGGCTGTGGCAGATGCCAGCAGCTCTTACCATCAGTCAGAGTCTTCAGGGTGTCAAGCTGTTTTCATTTTTTAGGCAA  7560
ATAGAACAAAAGCCATTTTGGTTCATCCTGATCACTTGAATGATAGACTCAATGCCCTGTGCCTGGCAGGGAGCGCTTGCAGAGGTGTCCTAGCCTTAGAGGGCTACTTCAGTGTCTCTA  7680
CTGACAGAAACTCCTGTATCTCAAATGGATCTCGAAGTTCTCTAGTAAGGAGTCCTAAGGATGACATGTATTGGGCCACTAGCAGGGATTGAAAACATTTTAAAAGAAATCCTTTTTCTT  7800
AGGAGTAAAAGCTGGTAAAAGGGGTGACTTCCTGGTTCTGATCAAAACCAGACCAAACCCTCATTTCAGCAAAGCCTTGCAAGACACTCCCTTGCTCATTTGCCATATTTAGATGTCTTA  7920
GTGGAGTCAGAGCCCTGTTTGGTATGTGTTTTTCATGCTAAGTCTAAATTGTCTTTTCATTTCATGATGCATTTTTTCTCTTTTGTCAGGATAACATCATATAGCATCTTGTTTGTTTTT  8040
CCTAATCTCTATGAACATATCTATCTACCTGTAACCGTAGATAGGTATCTAGATAGATACCAAGCTTTTAAGCTCTGGGCCACTATGCATCATTATTGGGTCTCTGCCTTAAAACACATC  8160
CAAATTTATATT(AAAA)29
```

FIG. 2F

```
   1 CCTGCGTCCT TCCTCCTTTT CCTCCTTCCC TCCTCCCTCC CGGGTAATTT
  51 ATTTCTAGCT TCCAGGCAAG GGCCACACAA GGAAGGAAAT CCACAGGGGA
 101 TTAGATGCCG GGGTGGTAAC TCCACCAGGA TAGGTTGGAC TCTGCAGCCA
 151 ACTTCCTATC AGATCACCCT GCACCTATTT CCGACCCGAC CGGAATGCGA
 201 CTGGCTTGAG GTCCAGCCCT TTCGCCTGGG CGGGAGCAGA GCCGCGGAAG
 251 CTFCTTGGAG TTGGATGGGG GTAGGAAGGG GCTGGAGCGG GAATCCTACG
 301 ATGCAACTGG CCTGGGCCTA AGGTTGGGCA TAATGGAGTT GCAGAGGACA
 351 TCCAGCGTTT CAGGGCCGCT GTCGCCGGCC TACACCGGGC AGGTGCCTTA
 401 CAACTACAAC CAACTGGAGG GAAGATTCAA ACAGCTCCAA GATGAGCGTG
 451 AAGCTGTACA GAAGAAGACC TTCACCAAGT GGGTCAATTC CCACCTTGCA
 501 AGAGTGTCCT GCCGAATCAC AGACCTGTAC ACGGACCTTC GAGATGGACG
 551 GATGCTCATC AAGCTACTGG AGGTCCTCTC TGGAGAGAGG CTGCCTAAAC
 601 CCACTAAGGG ACGGATGCGG ATCCACTGTC TGGAGAATGT CGACAAGGCT
 651 CTTCAATTCC TGAAAGAGCA GAGAGTCCAT CTTGAGAACA TGGGCTCCCA
 701 TGACATTGTG GATGGAAACC ACCGGCTGAC CCTCGGCCTC ATCTGGACAA
 751 TTATTCTGCG CTTCCAGATC CAGGATATTA GTGTGGAGAC TGAAGATAAC
 801 AAAGAGAAAA AGTCTGCTAA GGATGCATTG CTGCTGTGGT GCCAGATGAA
 851 GACAGCTGGG TACCCCAATG TCAACATTCA CAATTTCACC ACTAGCTGGA
 901 GGGATGGCAT GGCCTTCAAT GCACTGATAC ATAAACATCG GCCTGACCTG
 951 ATAGATTTTG ATAAACTGAA GAAATCTAAT GCACACTACA ATCTGCAGAA
1001 TGCATTTAAC CTGGCAGAGC AGCACCTTGG CCTCACTAAA CTGTTAGACC
1051 CTGAAGATAT CAGTGTGGAC CACCCTGATG AGAAGTCTAT CATCACATAC
1101 GTGGTGACTT ACTACCACTA CTTCTCCAAG ATGAAGGCCT TGGCTGTCGA
1151 AGGAAAGCGC ATTGGAAAGG TGCTTGATAA TGCTATAGAA ACAGAGAAAA
1201 TGATTGAGAA GTACGAGACA CTTGCTTCTG ACCTTCTGGA GTGGATTGAA
1251 CAAACCATCA TCATCCTAAA CAACCGCAAA TTTGCTAATT CACTGGTTGG
1301 GGTCCAACAG CAGCTCCAAG CATTCAACAC GTACCGCACA GTGGAGAAAC
1351 CACCTAAGTT TACTGAGAAG GGGAATTTGG AGGTGCTCCT TTTCGCGATT
1401 CAGAGCAAGA TGCGAGCGAA TAATCAGAAG GTCTACATGC CCCGCGAGGG
1451 GAAGCTCATC TCTGACATCA ACAAGGCCTG GGAAAGACTG GAAAAAGCAG
1501 AACATGAGAG AGAACTGGCT CTGCGGAATG AGCTCATACG GCAGGAAAAA
1551 CTGGAACAAG TCGCCCGAAG ATTTGATCGC AAGGCAGCTA TGAGGGAGAC
1601 ATGGCTGAGT GAAAACCAGC GTCTTGTGTC TCAGGACAAC TTTGGATTTG
1651 ACCTTCCCGC TGTTGAGGCT GCTACCAAAA AACACGAGGC CATTGAGACA
1701 GACATCGCTG CATATGAAGA ACGAGTTCAG GCCGTGGTGG CTGTGGCCAG
1751 GGAACTTGAA GCCGAGAACT ACCATGACAT CAAGCGCATC ACAGCGAGGA
1801 AGGACAATGT CATCCGGCTC TGGGAATACT TGCTGGAACT GCTCAGGGCC
1851 AGGAGGCAGC GTCTTGAGAT GAACCTGGGA TTGCAAAAGA TATTCCAGGA
1901 AATGCTTTAT ATTATGGACT GGATGGATGA AATGAAGGTG CTATTGCTGT
1951 CTCAAGACTA TGGCAAACAC TTACTTGGTG TTGAAGACCT GTTACAGAAG
```

FIG. 2G

2001 CATGCCCTGG TTGAAGCAGA CATTGCAATC CAAGCAGAGC GTGTAAGAGG
2051 TGTGAATGCC TCTGCCCAGA AGTTTGCAAC AGATGGGGAA GGCTACAAGC
2101 CATGTGACCC CCAGGTAATT CGAGACCGTG TTGCCCACAT GGAGTTCTGC
2151 TATCAAGAGC TTTGTCAGCT GGCTGCCGAG CGTAGGGCTC GCCTGGAAGA
2201 GTCCCGTCGC CTCTGGAAGT TCTTCTGGGA GATGCCAGAA GAGGAAGGCT
2251 GGATACCAGA GAAGGAAAAG ATCCTGTCCT CTGATGATTA CGGGAAAGAC
2301 TTGACCAGTG TCATGCGCCT GCTGAGCAAG CACCGGGCAT TTGAGGATGA
2351 GATGAGTGGC CGTAGTGGCC ATTTTGAGCA GGCCATTAAA GAAGGTGAAG
2401 ACATGATTGC AGAGGAACAC TTTGGATCGG AAAAGATCCG TGAGAGAATC
2451 ATTTATATCC GGGAGCAGTG GGCCAACCTG GAACAGCTCT CAGCCATTAG
2501 GAAGAAGCGC CTAGAGGAAG CCTCATTACT GCACCAGTTC CAGGCTGATG
2551 CTGATGATAT TGATGCTTGG ATGTTAGATA TACTCAAGAT TGTCTCCAGC
2601 AATGATGTGG GCCATGATGA GTACTCCACG CAGTCTCTGG TCAAGAAGCA
2651 TAAAGATGTA GCAGAAGAGA TCACCAACTG CAGGCCCACT ATTGACACAC
2701 TGCATGAGCA AGCCAGTGCC CTTCCACAAG CACATGCAGA GTCTCCAGAT
2751 GTGAAGGGCC GGCTGGCAGG AATTGAGGAG CGCTGCAAGG AGATGGCAGA
2801 GTTAACACGG CTAAGGAAGC AGGCTCTGCA GGACACCCTG GCCCTGTACA
2851 AGATGTTCAG TGAGGCTGAT GCCTGTGAGC TCTGGATTGA CGAGAAGGAG
2901 CAGTGGCTCA ACAACATGCA GATCCCAGAG AAGCTGGAGG ACCTGGAAGT
2951 CATCCAGCAC AGATTTGAGA GCCTAGAACC AGAAATGAAC AACCAGGCTT
3001 CCCGGGTTGC TGTGGTGAAC CAGATTGCAC GGCAGCTGAT GCACAATGGC
3051 CACCCCAGTG AAAAGGAAAT CAGAGCTCAG CAAGACAAAC TCAACACGAG
3101 GTGGAGTCAG TTCAGAGAAC TGGTGGACAG GAAAAAGGAT GCTCTTCTGT
3151 CTGCCCTGAG CATCCAGAAC TACCACCTCG AGTGCAATGA AACCAAATCC
3201 TGCATCCGGG AGAAGACCAA GGTCATCGAG TCTACCCAAG ACCTTGGCAA
3251 TGACCTGGCA GGTGTCATGG CCCTGCAGTG CAAGCTGACT GGCATGGAAC
3301 GAGACTTGGT AGCCATTGAG GCGAAGCTGA GTGACCTGCA GAAAGAAGCT
3351 GAGAAGCTGG AGTCCGAGCA CCCTGACCAG GCTCAAGCTA TCCTGTCTCG
3401 GCTGGCCGAG ATCAGTGATG TGTGGGAGGA AATGAAGACA ACCCTGAAGA
3451 ACCGAGAGGC CTTCCTGGGA GAGGCCAGCA AGCTGCAGCA GTTTCTGCGG
3501 GACTTGGACG ACTTCCAGTC TTGGCTCTCC AGGACCCAGA CTGCTATCGC
3551 CTCAGAGGAC ATGCCCAATA CCCTCACTGA GGCAGAGAAG CTTCTCACAC
3601 AGCACGAGAA TATCAAAAAT GAGATCGACA ATTATGAGGA AGACTACCAG
3651 AAGATGCGGG ACATGGGCGA GATGGTCACC CAGGGGCAGA CTGATGCCCA
3701 GTATATGTTT CTGCGGCAGC GGCTGCAGGC CTTAGACACT GGCTGGAATG
3751 AGCTCCACAA AATGTGGGAG AACAGGCAAA ACCTCCTCTC CCAGTCCCAT
3801 GCCTACCAGC AGTTCCTTAG GGACACCAAA CAAGCTGAAG CTTTTCTTAA
3851 TAACCAGGAG TATGTTTTGG CTCATACTGA AATGCCCACC ACCCTGGAAG
3901 GAGCTGAAGC AGCCATTAAA AAGCAGGAGG ACTTCATGAC CCACATGGAT
3951 GCCAACGAGG AGAAGATCAA TGCTGTTGTG GAGACTGGCC GAAGACTGGT

FIG. 2H

```
4001 GAGCGATGGG AACATCACCT CCGACCGCAT CCAGGAGAAG GTGGACTCTA
4051 TTGACGACAG ACACAGGAAG AATCGAGAAG CAGCCAGTGA ACTTCTGATG
4101 AGGTTAAAGG ACAACCGTGA TCTACAGAAG TTCCTGCAAG ATTGTCAAGA
4151 GCTGTCCCTC TGGATCAATG AAAAGATGCT TACAGCTCAA GACATGTCCT
4201 ATGATGAAGC CAGAAATCTG CACAGTAAAT GGTTAAAGCA TCAAGCATTT
4251 ATGGCGGAAC TTGCATCCAA CAAAGAATGG CTTGACAAAA TTGAGAAGGA
4301 AGGAATGCAG CTTATTTCAG AAAAGCCAGA AACAGAAGCT GTGGTAAAGG
4351 AAAAACTCAC TGGTTTACAT AAAATGTGGG AAGTCCTTGA ATCCACAACC
4401 CAGACCAAGG CCCAGCGGCT CTTTGATGCA AATAAGGCTG AGCTTTTCAC
4451 ACAAAGCTGC GCAGATCTTG ACAAATGGCT ACATGGCCTG GAGAGCCAGA
4501 TTCAATCTGA CGACTATGGC AAAGACCTTA CCAGTGTCAA TATTCTTCTG
4551 AAAAAGCAAC AGATGCTGGA GAATCAGATG GAAGTTCGGA AGAAAGAGAT
4601 CGAGGAACTG CAGAGCCAAG CCCAGGCGCT GAGTCAGGAG GGGAAGAGCA
4651 CAGATGAGGT GGACAGCAAA GCGGTTACTG TGCAGACCAA GTTCATGGAG
4701 CTTCTGGAGC CCTTGAGTGA GAGGAAGCAT AACCTGTTAG CTTCCAAGGA
4751 GATCCATCAG TTCAACAGGG ATGTGGAGGA CGAAATCCTA TGGGTTGGCG
4801 AGAGGATGCC TTTGGCAACT TCCACAGATC ATGGCCATAA CCTTCAAACT
4851 GTGCAGCTGT TAATAAAGAA AAACCAGACC CTCCAGAAAG AAATCCAGGG
4901 ACACCAGCCT CGTATTGATG ACATCTTTGA GAGGAGTCAA AACATCATCA
4951 CAGATAGCAG CAGCCTCAAT GCCGAGGCTA TCAGGCAGAG GCTCGCTGAC
5001 CTGAAGCAGC TGTGGGGGCT CCTCATTGAG GAAACTGAGA AACGCCATAG
5051 ACGGCTGGAG GAGGCACACA AGGCGCAGCA GTACTACTTT GATGCAGCTG
5101 AAGCCGAGGC ATGGATGAGT GAACAGGAGT TGTACATGAT GTCTGAGGAA
5151 AAGGCCAAGG ATGAGCAGAG TGCTGTCTCT ATGTTGAAAA AGCACCAGAT
5201 TTTAGAGCAA GCTGTTGAGG ACTATGCAGA GACAGTACAC CAGCTCTCCA
5251 AGACTAGCCG GGCGCTGGTG GCTGACAGCC ATCCCGAAAG TGAGCGTATT
5301 AGCATGCGGC AGTCAAAGGT CGACAAGCTG TATGCTGGCC TGAAGGACCT
5351 TGCTGAGGAG AGGAGAGGAA AACTTGATGA GAGGCACAGG CTGTTCCAGC
5401 TCAACAGAGA GGTGGATGAC CTGGAACAGT GGATCGCTGA GAGGGAAGTG
5451 GTCGCAGGCT CCCATGAGTT GGGACAGGAC TATGAGCATG TCACGATGTT
5501 ACAAGAACGG TTCCGAGAAT TTGCTCGAGA CACAGGAAAC ATTGGGCAGG
5551 ACGCTGTGGA TACAGTTAAT AACATGGCAG ATGAACTCAG CAACTCTGGA
5601 CATTCAGATG CTGCCACCAT TGCTGAGTGG AAAGATGGTC TCAATGAAGC
5651 CTGGGCTGAC CTCCTGGAGC TCATTGACAC AAGAACACAG ATTCTTGCTG
5701 CCTCATATGA ACTTCATAAG TTTTACCATG ATGCCAAGGA GATCTTTGGC
5751 CGAATCCAGG ACAAACACAA GAAACTCCCT GAGGAGCTTG GAAGAGATCA
5801 AAACACTGTG GAAACTTTAC AGAGAATGCA CACCACCTTT GAGCACGACA
5851 TCCAAGCTCT GGGCACTCAG GTGAGGCAGC TGCAGGAGGA TGCAGCTCGC
5901 CTCCAGGCAG CCTATGCAGG GGACAAGGCT GATGACATCC AGAAGCGTGA
5951 GAATGAGGTC CTGGAAGCCT GGAAGTCCCT GCTGGATGCT TGTGAGGGTC
```

FIG. 2I

```
6001 GCAGGGTGCG GCTGGTAGAC ACAGGAGACA AGTTCCGSTT CTTCAGCATG
6051 GTGCGTGACC TCATGCTCTG GATGGAAGAT GTCATCCGGC AGATCGAGGC
6101 CCAGGAGAAA CCACGGGATG TGTCATCTGT TGAACTGTTA ATGAATAATC
6151 ATCAAGGTAT CAAAGCTGAA ATTGATGCTC GTAATGACAG CTTTACAGCC
6201 TGCATTGAGC TTGGGAAATC CCTGCTGGCA CGGAAACACT ATGCTTCTGA
6251 GGAGATCAAG GAAAAGTTAC TGCAGCTGAC AGAGAAAAGA AAAGAAATGA
6301 TTGACAAGTG GGAAGACCGG TGGGAGTGGT TAAGACTGAT TTTGGAGGTC
6351 CATCAGTTCT GAAGGGATGC CAGTGTGGCA GAGGCTTGGC TGCTTGGACA
6401 GGAACCATAC CTATCCAGCC GTGAAATTGG CCAGAGTGTA GACGAAGTGG
6451 AGAAGCTTAT TAAGCGCCAT GAGGCGTTTG AAAAGTCTGC AGCGACCTGG
6501 GATGAGAGAT TCTCTGCTCT GGAAAGGCTG ACAACGTTGG AGCTACTGGA
6551 AGTGCGCAGA CAGCAAGAGG AAGAAGAAAG AAAGAGGCGG CCACCTTCTC
6601 CGGACCCAAA CACGAAGGTT TCAGAGGAGG CTGAGTCCCA GCAATGGGAT
6651 ACTTCAAAAG GAGACCAAGT TTCCCAGAAT GGTTTGCCGG CTGAGCAGGG
6701 ATCTCCACGG GTTAGTTACC GCTCTCAAAC GTACCAAAAC TACAAAAACT
6751 TTAATAGCAG ACGGACAGCC AGTGACCATT CATGGTCTGG AATGTGAAGT
6801 TCACTACCAT TTGTCAAGAA CCACTCTGTC CACATCCTTT GACCTTTTGG
6851 CTTCCACGTC ACCCAGAGTG TTAAAATTTT TACTTAATTC ATAGCTGTCC
6901 TTGATTTCAT ATTTGTTTGC ATTTAATTTA TGTTTCTTTG GATCCTCATT
6951 GCCTGAAAGC AGCATACTTA ATTTTTGTTT ATTTATTGTG A
```

FIG. 2J

```
GCGCTGCTCTGTGAGCTGGAGCACAGCGTGCTTAGAGTTGGCCATATTTAAAATATTTTCCAATAGGATCCTGCGTCCTTCCTCCTTTTCCTCCTTCCCTCCTCCCTCCCGGGTAATTTA  120
TTTCTAGCTTCCAGGCAAGGGCCACACAAGGAAGGAAATCCACAGGGGATTAGATGCCGGGGTGGTAACTCCACCAGGCTAGGTTGGACTCTGCAGCCAACTTCCTATCAGATCACCCTG  240
CACCTATTTCCGACCCGACCGGAATGCGACTGGCTTGAGGTCCAGCCCTTTCGCCTGGGCGGGAGCAGAGCCGCGGAAGCTGCTTGGAGTTGGATGGGGGTAGGAAGGGGCTGGAGCGGG  360
AATCCTACGGTGCAAGTGGCCTGGGCCTAAGGTTGGGCATAATGGAGTTGCAGAGGACATCCAGCATTTCAGGGCCGCTGTCGCCGGCCTACACCGGGCAGGTGCCTTACAACTACAACC  480
                                         M  E  L  Q  R  T  S  S [I] S  G  P  L  S  P  A  Y  T  G  Q  V  P  Y  N  Y  N  Q    27
AACTGGAAGGAAGATTCAAACAGCTCCAAGATGAGCGTGAAGCTGTACAGAAGAAGACCTTCACCAAGTGGGTCAATTCCCACCTTGCGAGAGTGTCCTGCCCGAATCACAGACCTGTACA  600
 L  E  G  R  F  K  Q  L  Q  D  E  R  E  A  V  Q  K  K  T  F  T  K  W  V  N  S  H  L  A  R  V  S  C  R  I  T  D  L  Y  T    67
CGGACCTTCGAGATGGACGGATGCTCATCAAGCTACTGGAGGTCCTCTCTGGAGAGAGGCTGCCTAAACCCACTAAGGGACGGATGCGGATCCACTGTCTGGAGAATGTCGACAAGGCTC  720
 D  L  R  D  G  R  M  L  I  K  L  L  E  V  L  S  G  E  R  L  P  K  P  T  K  G  R  M  R  I  H  C  L  E  N  V  D  K  A  L   107
TTCAATTCCTGAAAGAGCAGAGAGTCCATCTTGAGAACATGGGCTCCCATGACATTGTGGATGGAAACCACCGGCTGACAACGTTGGAGCTACTGGAAGTGCGCAGACAGCAAGAGGAAG  840
 Q  F  L  K  E  Q  R  V  H  L  E  N  M  G  S  H  D  I  V  D  G  N  H  R  L  T  T  L  E  L  L  E  V  R  R  Q  Q  E  E  E   147
AAGAAAGAAAGAGGCGGCCACCTTCTCCGGACCCAAACACGAAGGTTTCAGAGGAGGCTGAGTCCCAGCAATGGGATACTTCAAAAGGAGACCAAGTTTCCCAGAATGGTTTGCCGGCTG  960
 E  R  K  R  R  P  P  S  P  D  P  N  T  K  V  S  E  E  A  E  S  Q  Q  W  D  T  S  K  G  D  Q  V  S  Q  N  G  L  P  A  E   187
AGCAGGGATCTCCACGGGTTAGTTACCGCTCTCAAACGTACCAAAACTACAAAAACTTTAATAGCAGACGGACAGCCAGTGACCATTCATGGTCTGGAATGTGAAGTTCACTACCATTTG  1080
 Q  G  S  P  R  V  S  Y  R  S  Q  T  Y  Q  N  Y  K  N  F  N  S  R  R  T  A  S  D  H  S  W  S  G  M                         227
TCAAGAACCACTCTGTCCACATCCTTTGACCTTTTGGCTTCCACGTCACCCAGAGTGTTAAAATTTTTACTTAATTCATAGCTGTCCTTGATTTCATATTTGTTTGCATTTAATTTATGT  1200
TTCTTTGGATCCTCATTGCCTCAAAGCAGCATACTTAATTTTTGTTTATTTATTGTGAGCTTTTTACTTTAAGATTTTACATGAGTAATCAAAATTAAATTATAGCATAATG  1312
```

FIG. 3A

```
1    TTGGAACAGTTACTTCAGTGGAGGCAGCAGAAATGAGGCTAGTCCAGACTCACAGGAATAGGGTTCCATTCTCAAGAAGATGATTTA

88   AAGTAATTATCCTTTACGCATAGTTATCATCACCACAAAAAAAGATTCCAACCTTTTCCACAGAACTATTATGATTTATTTTTATAT

175  GAATGTATGTATTTATTATTATATGAACTCCTATAATGATCACCTTTACATATTCACATTTTCTTAATAATTAGTTTAGCCGCGTCC
         ——► W57358, W47742

262  GGAGGTCCGACAGCTCTGCAGCTCCGAGCGCGCGACTAGCCAGAAAGTTTCAGGCCATCCATGAGCCACCAGGAAAGGATTGCCAGC
                                                                  M  S  H  Q  E  R  I  A  S

349  CAGAGGAGGACAACAGCCGAAGTCCCAATGCACAGATCAACTGCCAATCAAAGCAAGAGGAGCCGGTCACCATTTGCCAGCACACGT
     Q  R  R  T  T  A  E  V  P  M  H  R  S  T  A  N  Q  S  K  R  S  R  S  P  F  A  S  T  R

436  CGTCGCTGGGATGACAGCGAGAGCTCGGGAGCCAGCCTGGCTGTTGAGAGTGAGGATTATTCCAGGTGGCGGGATGCTGCCGATGCT
     R  R  W  D  D  S  E  S  S  G  A  S  L  A  V  E  S  E  D  Y  S  R  W  R  D  A  A  D  A

523  GAGGAGGCTCATGCCGAGGGCCTAGCCAGAAGAGGCCGAGGTGAGGCTGCCAGCAGCTCAGAGCCAAGGTATGCTGAAGACCAGGAT
     E  E  A  H  A  E  G  L  A  R  R  G  R  G  E  A  A  S  S  S  E  P  R  Y  A  E  D  Q  D

610  GCCAGGAGTGAACAAGCGAAGGCAGACAAAGTGCCAAGACGGCGGCGAACCATGGCAGACCCTGACTTCTGGGCATACACCGACGAT
     A  R  S  E  Q  A  K  A  D  K  V  P  R  R  R  R  T  M  A  D  P  D  F  W  A  Y  T  D  D

697  TACTACCGATACTACGAGGAAGATTCTGACAGCGACAAAGAGTGGATGGCTGCCCTGCGCAGGAAGTACCGAAGCCGAGAGCAACCC
     Y  Y  R  Y  Y  E  E  D  S  D  S  D  K  E  W  M  A  A  L  R  R  K  Y  R  S  R  E  Q  P

784  CAGTCCTCCAGCGGAGAAAGCTGGGAGCTTCTGCCAGGAAAGGAAGAACTGGAACGTCAGCAAGCCGGAGCTGGGAGCCTCGCCAGT
     Q  S  S  S  G  E  S  W  E  L  L  P  G  K  E  E  L  E  R  Q  Q  A  G  A  G  S  L  A  S

871  GCTGGCAGCAATGGCAGTGGTTATCCTGAAGAAGTACAAGACCCATCTCTTCAGGAGGAAGAACAGGCCTCTCTGGAAGAAGGAGAA
     A  G  S  N  G  S  G  Y  P  E  E  V  Q  D  P  S  L  Q  E  E  E  Q  A  S  L  E  E  G  E

958  ATCCCTTGGCTTCGCTACAATGAGAATGAAAGCAGCAGCGAGGGTGATAATGAGTCTACCCATGAGCTCATACAGCCTGGGATGTTC
     I  P  W  L  R  Y  N  E  N  E  S  S  S  E  G  D  N  E  S  T  H  E  L  I  Q  P  G  M  F

1045 ATGCTGGATGGAAACAACAACCTGGAAGATGACTCCAGCGTGAGCGAAGACCTCGAAGTGGACTGGAGCCTGTTTGATGGGTTTGCC
     M  L  D  G  N  N  N  L  E  D  D  S  S  V  S  E  D  L  E  V  D  W  S  L  F  D  G  F  A

1132 GATGGCTTGGGAGTGGCCGAAGCCATCTCCTACGTGGATCCTCAGTTCCTCACCTACATGGCTCTGGAAGAGCGTCTGGCCCAGGCA
     D  G  L  G  V  A  E  A  I  S  Y  V  D  P  Q  F  L  T  Y  M  A  L  E  E  R  L  A  Q  A
                                  ——► clone CH7
```

FIG. 3B

```
1219 ATGGAGACGGCCCTGGCACACTTGGAGTCTCTCGCCGTTGATGTCGAAGTGGCCAACCCACCAGCAAGCAAGGAGAGCATTGATGCC
     M  E  T  A  L  A  H  L  E  S  L  A  V  D  V  E  V  A  N  P  P  A  S  K  E  S  I  D  A

1306 CTTCCTGAGATCCTGGTCACCGAAGATCATGGTGCAGTGGGCCAGGAAATGTGCTGTCCTATCTGCTGCAGCGAATATGTGAAGGGG
     L  P  E  I  L  V  T  E  D  H  G  A  V  G  Q  E  M  C  C  P  I  C  C  S  E  Y  V  K  G

1393 GAGGTGGCAACTGAGGTACCATGCCACCACTATTTCCACAAGGGCTGCGTGTCCATGTGGCTTCAGAAGTCTGGGACCTGCCCAGTG
     E  V  A  T  E  L  P  G  H  H  Y  F  H  K  P  C  V  S  I  W  L  Q  K  S  G  T  C  P  V

1480 TGCCGCTGCATGTTCCCTCCCCCGCTCTAAAAGCCAAGGCTCGTCGTAACAGTCAGCCTGGTTACATTCCCTGTCCGAAACCCACAA
     C  R  C  M  F  P  P  P  L  *

1567 TACTACAGGAGCCCTTGTTCTAAACTTACAATGAAACCAGTCAGTCAATTAGACTAAAGTTGTTGATTCCTTGTGATTATTTGGATG

1654 TGAAAATGGTTGTGTACAATGACATTTAAAAAAAATCATCCTCTCGTTTAGAAGGTAGAAAGGGGGAAAGGAAACTTTCTAAATGCT

1741 GCTTGAGATTGCAGTAAGAACATACATTTTCTAACCTGAAAGTTGAAACAAATCCCACTTGTTCTGTAGACTGTGTCTCTCTTACCT

1828 GTTGCTGTCAGGGTTACCTATCTGCTAAACTATGTCGGAAAGACAAAATTACTTTTGTTGCATGTCATGGGTTAATGTTCCTGTATT

                                                ← primer DI
1915 TGCAGTGGTGTAAAAGCTTATTAAAGTTCTTCTTTTGCTTTGACCCCGAA
```

FIG. 4A

```
   1 GGGCAACTGA AGGCAGATGA AGAGCCCTGC CCCTGCCCAC ATGTGGAACC
  51 TTGTGCTGTT CTTGCCTTCA CTGTTGGCTG TGCTTCCGAC CACTACTGCC
 101 GAGAAGAATG GCATCGATAT CTACAGCCTC ACGGTGGACT CCCGGGTCTC
 151 TTCCCGATTT GCCCATACTG TTGTCACCAG CCGGGTGGTC AACAGAGCCG
 201 ATGCTGTTCA AGAAGCGACC TTCCAAGTAG AGCTACCCAG GAAAGCCTTC
 251 ATCACCAACT TCTCCATGAT CATCGATGGC GTGACCTACC CAGGGGTTGT
 301 CAAAGAGAAG GCCGAAGCCC AGAAACAATA CAGTGCCGCC GTGGGCAGGG
 351 GAGAGNGTGC TGGCATCGTC AAGACCACTG GGAGGCAGAC AGAGAAGTTT
 401 GAAGTGTCAG TCAACGTGGC CCCTGGTTCC AAGATTACCT TCGAACTCAT
 451 ATACCAGGAA CTGCTCCAAA GGCGACTGGG AATGTATGAG CTACTCCTCA
 501 AAGTGAGGCC TCAGCAGCTG GTGAAGCACC TTCAGATGGA CATCTACATC
 551 TTTGAGCCTC AGGGTATTAG CATCCTGGAG ACAGAGAGCA CCCTCATGAC
 601 CCCGGAGCTG GCAAATGCCC TTACCNCTTC ACAGAACAAG ACCAAGGCTC
 651 ATATCCGGTT CAAGCCGACG CTCTCCCAGC AACAGAAGTC TCAGAGTGAG
 701 CAGGACACGG TGCTGAATGG GGACTTCATC GTCCGCTATG ATGTCAACCG
 751 GTCTGACTCT GGGGGCTCCA TTCAGATTGA GGAAGGCTAC TTTGTGCACC
 801 ACTTTGCTCC AGAGAACCTT CCTACAATGT CCAAGAATGT GATCTTTGTC
 851 ATTGATAAAA GCGGATCTAT GTCAGGCAAG AAAATCCAGC AGACCCGAGA
 901 AGCCCTAGTC AAGATCTTGA AAGACCTCAG CCCCCAAGAC CAGTTCAACC
 951 TCATTGAGTT CAGTGGGGAA GCAAACCAAT GGAAGCAGTC ACTGGTGCAA
1001 GCGACAGAAG AGAATTTGAA CAAGGCTGTA AACTATGCTT CCAGGATCCG
1051 GGCTCACGGA GGGACCAACA TCAATANTGC AGTGCTGTTG GCTGTGGAGC
1101 TGCTGGACAG AAGCAACCAA GCTGAGCTAC TGCCCTCGAA GAGCGTCTCC
1151 CTTATCATCC TGCTCACGGA CGGTGACCCC ACTGTGGGAG AAACCAACCC
1201 CACGATTATC CAGAACAACG TGCGGGAAGC CATCAATGGG CAGTATAGCC
1251 TCTTCTGCCT GGGGTTCGGC TTTGATGTGA ACTATCCTTT CCTGGAGAAG
1301 ATGGCACTGG ACAATGGTGG CCTGGCCAGG CGCATCTATG AGGATTCAGA
1351 CTCTGCACTG CAGCTTCAGG ATTTCTACCA CGAAGTAGCC AATCCACTGC
1401 TCTCATCAGT GGCCTTCGAA TACCCCAGTG ATGCTGTGGA GGAAGTCACT
1451 CGGTACAAGT TCCAACACCA CTTTAAGGGC TCAGAGATGG TGGTGGCTGG
1501 GAAGCTCCAg GACCAGGGTC CTGATGTCCT CTTAGCCAAA GTCAGTGGGC
1551 AGATGCACAT GCAGAACATC ACTTTCCAAA CGGAGGCCAG cGTAGCCCAA
1601 CAAGAGAAGG AGTTTAAGAG CCCCAAGTAc ATCTTTCACA AcTTTATGGA
1651 GAGACTGTGG GCAcTGCTGA cTATACAGCA ACAGCTGGAG CAGAGGATTT
1701 CAGCGTCAGG TGCCGAATTA GAGGCCCTCG NGGCCCAAGT TCTGAAcTTG
1751 TCACTCAAGT ACAATTTTGT CACCCCTCTC ACGCACATGG TGGTCACCAA
1801 ACCTGAAgGT CAAGAaCAAT TCCAAGTNGC TGAGAAGCCT GTGGAAGTCG
1851 GTGATGGCAT GNAGAGACTC CCCTTAGCAG CTCAAGCCCA CCCCTTCAGG
1901 CCTCCTGTCA GAGGATCTAA ACTGATGACC GTGCTGAAAG GAAGCAGGTC
1951 CCAGATACCC AGACGCGGTG ATGCCGTTAG GGCATCTAGG CAATACATTN
```

FIG. 4B

```
2001 CTCCCGGATT CCCCGGACCT CCTGGACCTC CCGGATTTCC TGCACCCCCT
2051 GGACCTCCTG GATTNCCTGC ACCCCCTGGA CCTCCTCTTG CTTCTGGCTC
2101 TGACTTCAGC CTTCAGCCTT CCTATGAAAG GATGCTAAGC CTGCCCTCCG
2151 TTGCAGCACA ATATCCTGCT GACCCACATC TGGTTGTGAC GGAAAAAAGT
2201 AAAGAAAGCA CCATACCAGA GGAATCCCCN AACCCAGACC ACCCCCAGGT
2251 TCCTACTATT ACCTTGCCGC TTCCGGGATC CAGTGTGGAC CAGCTCTGTG
2301 TGGATATCTT ACATTCTGAG AAGCCCATGA AGCTGTTCGT AGACCCCAGT
2351 CAGGGTCTGG AGGTGACTGG TAAGTATGAG AATACTGGGT TCTCGTGGCT
2401 CGAAGTGACC ATCCAGAAGC CTCACCTGCA GGTCCATGCA ACCCCTGAAC
2451 GACTGGTGGT GACACGAGGC AGAAAANACA CTGAATACAA GTGGAAGAAG
2501 ACGCTGTTCT CTGTGTTACC TGGCTTGAAG ATGACCATGA ATATGATGGG
2551 ACTCCTACAG CTCAGTGGCC CAGACAAAGT CACCATCGGC CTCCTGTCCC
2601 TGGATGACCC TCAGAGAGGA CTAATGCTGC TTTTGAATGA CACCCAGCAC
2651 TTCTCCAACA ACTGGAAAGG GGAGCTTGGT CAGTTTTACC GGGACATCGT
2701 CTGGGAGCCA CCCGTCGAGC CAGATAATAC AAAACGGACA GTCAAAGTTC
2751 AAGGAGTTGA CTACCTGGCT ACCAGAGAGC TCAAGTTGAG TTACCAAGAA
2801 GGGTTCCCAG GAGCAGAGAT TTCCTGCTGG ACAGTGGAGA TATAGAACTG
2851 TTAGGAGCGC CGCTCCCTGC CATGTTGTCC TCGTACGCAG GCAGATGACA
2901 CCTTATGCCA ACAGGGACGC CTGTGAGGCC GAGACCTTGA TGGGAAGAGG
2951 ATGCTCCCTT GTTACAAATA AAGAAGGGCA GTGTGAACCC GA
```

FIG. 5

GGTGGCCAAGAGCAGTTCACCTGCTCTGGGGCAAGCCTTGCTTGTG
TTTTAGTGAGTCAGGGCCTCCCCAGGCAGTAAGATGTTGAGTGTGG
AGGCCCAGGCCGCTGACCTGCAGCCCTGTCCCCCACAGGCAGGCTG
CATGCTCTTCCCCCACATTTCTCCTTGCGAGGTGCGCGTGCTCATG
CTCCTGTACTCGTCTAAGAAGAAGATCTTCATGGGCCTCATCCCCT
ACGACCAGAGCGGNTTCGTCAACGCCATACGACAGGTCATCACCAC
CCGCAAACAGGTGTGCCAGCTGAGGGTAGNCTGCTCCTGCTCCTAC
CCTTGGTAGACCCACTGNCTCCCACTGGTGTGGAATGTGGCATCAA
GGCTGAGTCGGCGNCTGGGGAGGAGCTGTGACGANGCAGTGCCATA
CCCAAATGGGCTCGAGGGAAACNTAGCTTTATAGGGTTCAGAGGGG
CAGAACTAGAGGGTGGGGCCTGGGTGTAGAGGCAGGGCAGGAGTGG
GGTGGCAGGTTTGGCAAGAGGCCCAGAGTCTCTGGAGGGTCACAGT
GTTGATGACATCTTTCTNAGAANCCTGCTACTNGCTTAGNCAGCTG
TGGTCCTCTCTNCCACCTGGGGGATACCTGGCNACAGGCNGTGGGC
NNCGGGGGTGAANACTCTGGACCTGTTNAGANTGTCAACAACAAAT
TCTTGACATGGAGTGGTGTCATGGAGTGGNAGGAGGTGANCTGCCG
GGGACTGTGTGGACTGTTGNCCCTAAGCTGCCCTCCCCTGAAGTGC
CTTCTCGCTCTGCCCCAAAACCCAGACCTGAGCCCAACAGCCGGTC
CAAGAGGTGGCTGCCATCCCACGTCTATGTGAACCAAGGGGAGATC
CTGTGATTCCGGGTACCCCCGGGTGGCCCCATTGACAGTGCCGCCC
CCCTGGGGGAGGACTTCTGACTGATACCTCCTGTCTTGTGTGGCAG
GAGAACAGACCAGTGGCCTCGGAGGCTCTTCATGCAGCTCATTCCC
CAGCAGTTGCTGGTGAGGGGTCAGGGGATTCCAGGCTGGGGGTGGG
CCAAAGACCCTGTGGTGGGCTGGTTCAGAGGCCTGCCTGGCTTCCC
CAGCAAGCTAGGGTTCCATAAAGAAGCCCTCGGCCTTCCCCCAGAC
CACCCTCGTGCCACTGTTCCGGAATTC

FIG. 6A

GGCACGAGCTTAACTGTGCTAACTTCTGTGATGATCATGTGTGATGAGTATGTGCTCT
CATTTGATTTGTGGAAAAAAGAAAAGAAAAAAATCCGAAGGACACAAAGAGGACT
AATCTTAAACCAGATATCTAGTAGTCACCAAAGCCACACTTTGAATTCGAAAAGCTT
AGCACTGTAGCTTAGCTCATGCTATCTTTTAAAGAGAGAATTTAATTATTTAATATAT
GGAAGGACATTAGGCTAGTGTGTCTGGCACATGGTATAAACTCAATAAATGGTGGAC
GTTATCAGTGCTACTATAATGAGTTTAATAATTTGGTTTCATCTCCTTTAATCAGACC
AGTGTTCACTACTAGCTGGGTCTCTGGAATAGGCACAGATATATTCATCTGGAGTGTC
ACACATACTCTGTGCGCGAAAGAGTTCAGAATAGCCCTTCAATAAGCCAATTACTCTT
GCTGTCATCCTTATTTCTTAACTTTCCCTTAGCGTTGCTTTTATGTATCAAACTTTTCT
TCCTTATTTTACGTAATACTTTTAATGACAACTTTCTAGAAATAAGAACTATACCCTA
AAAGATTGAAATATTCTTAGTTTTCTTTATCTACATCAGAAATTGTTTAGCTGATACA
ACATACTTATATTGTTTAAGGAATTCTGTTTAATACCTTGGTATTTATAATTTTCATAA
GTTTATTTGTATTAATAGGAACTCTTACAAAGAATGTATAGAAAATAAGCCCCATCAT
TTGTCAGTGTGACAATTTTCCCAGTGTTTAAATTGTTTAAGCTGTTTGTACCCCTATAT
AAGCTCTGTTCCTTCTTTGGCCCTTTCCCCCTTAGCCTAAATCTCCATTTTGCCTGACG
ATCTCTTCCCTGACAAAATGCCTGCTTCTGCGCACTGAGTCACAGTCTACTAAAATGC
ATTCCATTGTGCCCATGTCCCTCTTAATGTGATGACCCCAGACATGACCAGGGCAGAG
CACAGAGGGAGCATCACTTTCTTTGACCAGAGCATCTATTTCCAGCAATGCAGCCTA
AGGTCACATTAGCATTTTTGGCAGCAAAATACACCCTTGGCTCATGCTGTTATGCTGT
CAACCAAATCCTCCATGACTTTTTCACATGAACTCCCATTAAATAAGGCTTCCCACAT
CCGGTACGAATATAGACAGTAATGTGCAGTCTGGTGAAGTTATTTACATAAGTTCCTA
TTAAACATCAGCTAATCTATATTTATTATTTTAGAATATTGAGACAGATTTCTATTCC
CAGCTATATAGATATGGTTTTAGAATACTTTATTATTATTTTTTTAATGTGTCTTCTCT
GAACCCGATAAGAACATAGTCCCAGACAATCTTTAAGTTCAGAGTCTTACAGTTTGT
ATAGAGACCTAGAGGCTAGCTATATTTCTTTAGACATCAACACATCATCAGATAGGA
TCCACCCAAGGCCTTACAAATCCTGTATACTGAAATGCCTTTTCCTGACGATATTCT
GGAGACTGTTAAGTGAATGCGCAGATCTGAACCGAGCCGAGCCTGTAGTGGGGAAGA
GCTAAAGCATGGCAGTTGTCTTCATCAATGATGGAGTCTTTCATTATGTTGTCTCAAA
AGACACATGCTTCAGCCCTGGGTCTCAAAACTCTCATGCTTCGGCCCTGGGTCTCACA
CTCCTGGCTTCCCGAGTGGTCATAGCTAAGACCTTCTCACACTAAATCCCAGGATGAG
CTCATGTTGATGTTCCTGCTTGCTTCTCTGAAATTGGCAGTTCTCGTGGAAAAAAA
TCTACTTATACTTGTGTGCTTCATAAAGCAACTCGGTAGCAGGGCTTAGGGGTGCTTC
GAGTGTGGCAGTGATAGAGAAGACCGATAAAGCGAAATCTATGATATCTCATACATC
ATTTTAATTATTTAAATTACTTTTGTTAGTACACAAAAGTATTTGTTAGTACACCCTG
TTTATCTATGTGTATACTCTACCTTTCGCATACACTGACTTCATTTCTTTTTCTCCTCA
CCCATCCTGATGAGCTGCTCTCCTCCCAGACAAGCTCTGGCAGTTTTAAAGTCACGTG
TGTATCTTTTAACTCTAGCTTCTGCCTATTAGACAAAACAAGATACTTGTCTTTCTCCC
CATCTCCCTCCTTTTGTTTAATTCTCCTCCAGCCCTACATGGATCCCCCTTGACCTCGT
GTCATATATCTAAATCTGTATAAATAAAGAGATGATTTAATCTACGTTCTATGTACAA
AAGAGAATATAAATGCTCGTCTTTCTGAATCTGTCTTATTTGGTTTCACACAATATCT

FIG. 6B

GCTCTCTTTTACCGCAAATGGTATCATCTCGTTCCCTTTACACGTTGAAGAAAATTTC
ATTTGTGTGTGTGTGTGTGTGTGTGTGTGAACTATATATTTTTACGCTATCTGGTG
AGGAACATCAAGGCCAAGATATGGATCTTGGCTATTGTAAAGAGTGTAGTAAGAAAC
ACAACCGTATAATCATCTTCTGTTGCATGCTGGCATGCTGGCTACAATCCTCACCTGTG
TACCCAGAGTGAGAGCTGGACCACATGGTAATGCAACCTGTAGTTATTATTTAATGT
GTACTTCTTGTTTAATGTTTAAAGATACTACTTATTTTAATGTTATGTGTATGGATGTT
TTATCTATGTGTTTGTCTGTATATAGTGGGCACGTACTGGTCTCAGAGCCAGAGGAAG
GCATCAGAGTCCCTGGGGTTGGAATTAAAGATGTTTGTGAGTACCTGCGTGTATCCTG
GACTTCAAACCCGGGTCTTCTTCAAGAGCAGCCAGTGCTCTTAACCACTGAGGATCTC
TCCAGCCTCATCGCTGATTTAGGAAGGACTTTTACTGATTTGGAGTAGCTGTAGGCAA
TGCAGTCTATGACGATTTCCTTTTAGCAGTTCTTGTTTGTTTTCTTAATGATAGCCATA
CTGATTGCTGAGATTTACAGCAGCACTAGCAAGCTGGAA

FIG. 7

```
CTCGAGTTTTTTTTTTTTTTTTTTT GGAGAAGGGNAACATTTATTCATTC   50
AACAAATNTTGATGACCTGATGGGGNAGATAACTGAGCTAGTCAGCGCGT  100
AGGTAGCAAACATAAGGNTATAGTACCCCAGNTAATGGTCTNCCCACATG  150
TCACTGAAGGAGTGTCAGTTCTCAGCATTTTACCTTTAATTTTAATTTTT  200
ACCTCTAAATGCGCTTTAGGAGGCTACCCACAGTTGATGACAAACAGTGT  250
AGCCAGGCATGCCAGAACTGTTACCAGCAGAACTTTTGGCCGACTGTAGC  300
TGGCAGTGTTCTCAGTAGTGCAGTTCATGCCTGGTGGGTGTAACTAGGGT  350
ACAACGAAGTCACTTTGAACTCTTTTGCTAACTAAATAAGCCAAATAAAC  400
AAATCATGAAATACTGATTAGCAATGCAATATTTCATGGCATGGGAAGAG  450
CTTCGACTTCTCCATCGGTGACAAGGAGCAGCTTCTGGAAGGAAGGTCTG  500
GAGAAAACAAGTGACGGGGAGCTCCGAGGAGCCCTGAACACGTCACTCAA  550
CAGCACTGGCGTTGACACAGCTGCTGTGGTCCAGCAGTCACTCAGTGGAG  600
AGTGCCAAAGGGTGGGCAGACAGNCAGNCCTACTTCTTCATCTCCAGGAT  650
GGCACTTCCAGGCCCACGGTTCTTAGCACTACAGATGTTGCAGTATTGTG  700
CAGGAGCATTCATGCTCGGCATAGGCAGGCACTCCTTGTGGAACATGTGC  750
CGGCAGTGGAAGACCACCACGCTGAAGGGCTTCNCTGCATCTGTTGGGAG  800
GATGGGAGAAAGGCATGATTCACAGATATTCTCTTCATCAACCAGAACGC  850
CTTTCATTTGGGTTCGGNGCATTTTTTCACACACCAACGACAATGAGTCA  900
GCTACGAGGATTTTCTTGCAGCCTTCCCGAAGCAGAATCTTCAAGTTATA  950
ATCTTGCAGAATTTTAACCAAGGAATCTCTCAAATTGGGAATCTCCATTC 1000
CTTCCTTAATTCGGTGGATAAGTAGAATCGGGTCCACATGTGTGCCAATG 1050
TTGTTCAACAAGCCAGTGATAAATGGTGGTTTGTCGATGGAGTATAGAAT 1100
CAGATCTTCTCGTGCCGAATTC                             1122
```

FIG. 8

```
CTCGAGAGATGCCCCACAGTCCCTCAGGACCCGAGTCAGGTAATCTGCCT   50
TTGGCCTTAGTGACCTCCTTTTCTGGCGAGTATACCATCCACTTTCCTC  100
CCTGACAGGCAGTTCAGTAACCCAACCCTTTCATTCCTCCTTCAGTTGTC  150
AAAGACAAGTTAACATCCAAGACTAACAAGCAAGATGACTCAGGAGCATG  200
GNCTCTGGGTTCCCCTGGCACCATGCATGGTGATGCTAGTTAAGGCTGAC  250
TTAGCTCTTAGCAACCTTGGTTGGGATAGCTTAAGCTCATCTCCACTTTC  300
CTACCAAACAGAAAAGAATTTGAGTCCTCTTGCTATGAGGCTCTCGCTCC  350
CATCTCAGGCGAGCTTCCTGCCCCTCACCCAAGCTTGGGAGGTAGAGTTA  400
TGGAGAGGGCAAGGAAGCAGGACTGGAAAGATAGACTTATGGATCCACCA  450
CTCATAAAGTCACAAAGTCCCCTCACACCTGCTAGACTTAGACTCTAAAT  500
CATTACGTTGTCACCAACAGAGGTGACTCCTCAACCACAAGAGCCTGTAG  550
TGAGCTTCAAGAGAGAAGAGGACAAGNCAGACCTGGACTGCATGACCTTG  600
CACCTGTGATGAAGTCACAGCAATAGGTGATGCTCAAAAAGCCCCAATAA  650
AATGCAAGACAGNCAAACAGAAGCCCTGTCTGTCCCCATTGGTGGGTAAT  700
GTAGCTGATGTGGCTGGTTCTCCTTCCTTGACTTCACCCTGACTATGGGA  750
ATTGTCCTTCAGTGCCTCGTGCCGAATTC                        779
```

FIG. 9

```
CTCGAGAGGTGAAGGCAGAAGTATCACAAGTTCAAGTTCAAGGNCAGCCT    50
GGGCTTCACAAGACCCAAAAAAATAAATATGAGGNCAGTCCAGGCTGGGA   100
CTCAGGTCACTGCTGTGCTGAGCCATCGTCAGAGAAGTTTCTTCTTTNNT   150
TTTGATAGGAGCTAACACAGCGACCCACANCTGGACAGNCTGCAGTGAGT   200
GAGTGAGTAAGTGACCTAAAAGTGATGTCTTCATTAATCTCCCCTCCCCA   250
GGCNTCAGGGAGCTCTGAGGAAGAGGAGGCAGAAAGATGGTGAGAGCCAG   300
CAGGGATGGAGGACACCAAGGAAGCAGTGTCTTCCGACACAACAGGACTG   350
GCATTTAGGAAGTCACAGAGGCTGTGGCTGCCCAGGGCCTGCACGGTCCA   400
AGCTGGCTGAGATTCCAGTGCTGAGAGAGACAATTCAACACGGNCTCCCA   450
CCCCTAGNCAAGAAGTTATCTCCAACTGATATCCACTTGCAAAGGAAAAA   500
ATTAGGGGGNTAGAGAGATGGCTCAGTGGNTAAGAGCACTGACT......   544
..................................................   600

.....TANAAAATAGAAATNGCANATTNGNTNNGANGTTNGCNAAATNGC  1200
TGAGAAATGGCCAATTGGCTGGAAAACTTGCAACATTGCCTGGAGAACTG  1250
CCAAATTGCCTGGAGAGCTGCCAAATTGGCCTGGAGAGCTGCCTACATGG  1300
CCTGGAGAGCTGCCCACATGGCCTGGAGAACTGGCTACATGTCCTGGAGA  1350
GCTGCCAACATGTCCTGGAGATCTGCCTACATGGCCTGGAGAACTGCCTA  1400
CATGACCTGGAGAGCTGGCCACATGGCCTGGAGAGCTGGCTACATGACCT  1450
GGAGAGCTGNCTACATGGCCTGGAGAGCTGGCTACATGGCCTGGAGAGCT  1500
GGCTACATGGCCTGGAGAGCTGGCTACATGGCCTGGAGAGCTGGCTACAT  1550
GGCCTGGAGAGCCTCCCAGCAAGGCCTCTCTAAGCCGAATTC          1592
```

FIG. 10

```
CTCGAGATGCATTAAAGCTTTGNTGCAGAAGGATCCGAGTGTGTCCTGTG   50
TGTGTGTCCTCACTGGCGAGACCCTTTATCACACAGGGACACCCCTTAGG  100
TTGGAGTTTTCCTTGTAATGTCCACTATACGTCTGCTTTATACAATAATA  150
TTGNTTAAATTTGNCTCTATCATGAAATACCTCACTTTCCTTATCTGTAT  200
TGATTGAAAGTTTTGGTGGATGTAATAGTTTGGGCTTGGATCTGAAGTCT  250
TTTAGAGTTTATTGGACATGTGCCTNGATTCATTGGNTTNAAAATCNTCC  300
ACNACTTGGGGGTGTAAAGGTTACCCACNCNATTANTGGAGGTTCTTCTG  350
AGTTCAGAGANAANGANTGAGCCACCNGGAATTCT...........      400

 CCCTAAACACACTTTGATCATTTCCTGCCTAACCCTGCAGAGGAAATAT 1550
TAATACCCTGTAGTACCAAAGGAAACAAATAAGAAGGAAGACTGNTCTCT 1600
CATGTCTGGAGGAAGTTTGGTGAAGGAGTCTTCTGTTTGCTCACATAGGA 1650
GAGATCTAATACAGCCACTATCCATAATTAAAAATCTCTGTGAGAGAGGC 1700
ATGACGAGGTTCTCCCAGTCTGTCAAGGATGTGAATATGTGTTNCCCTG 1750
```

FIG. 11

```
GAATTCNGCNTTGGGGTACATGGACCNGGAGAGCTTGGNTACATGGCCTG   50
GAGAGCTGGNTACATGGCCCGGNGAGCTGGTTTNATAAACCTGGGGANGT  100
TGGGTTNAATGGCCCCGGGGANGTNGGTTNAATANACCNGGGGAGG....  146
.........................TGTCTGAAAANAGTGGNCACGTACT  200
GTTCTCAGACCCAGNGGAAGNCATCAGAGTCCCCTGGGGTTGGAATTAAA  250
GATGTTTGTGAGTCNCTGCGTGTATCCTGGACTTCAAACCCGGGTCTTCT  300
TCAAGAGCAGCCAGTGCTCTTAACCACTGAGGGATCTCTCCAGCCTCATC  350
GCTGATTTAGGAAGGACTTTTACTGATTTGGAGTANCTGTAGCCAATNCA  400
GTCTATGACGATTTCCTTTTAGCAGTTCTTGTTTCTTTTCTTAATGATAG  450
CCATACTGATTGCTGAGATTTACAGCAGCACTAGCAAGCTGGAACTCGAG  500
```

FIG. 12

```
CTCGAGNTTTTTTTTTTTTTTTTTTTTTTTTTTTTTTTTTTTTTTTTTTT    50
TTTTTTTTTTTTTTTTNNNNNAANAAANTTTTAAAGTTTTTTTTTTTTTAT   100
NAAAANNTTTCCAAGGGGGGGANGGGTTAGAAGANAGCCANAGCCTGGNC   150
CCCCCTGCCAGAAAAAACCAGAGGGGGGTTGATGTCCCCAAGTCCAGTTG   200
TCACCCTGAAGAAGTTCCCCACGATTTCCCTGGTGGCCCCCCGGGAGTAC   250
GTCCAGAGTGTCACCCTTTCCATTTGGGAGCTGTGGGAAGGGNGTGGGNT   300
CCCTCCCAGNGGGGCCCCAAACCCTTCTCCTGAACAGNTCCTGATTTCTG   350
aCCATCTTTCCAATTCCACGGATTCAAAGAGCATGACCCTAGGTAAGCAA   400
GCCAGGTCAAGAGCATTGCTTGtCTGNAGGAAAAGGAAGGGTCCCTCCTG   450
GcCTCGTGCCGAATTCC                                    467
```

•EMBRYONIC LIVER FODRIN OR BETA SPECTRIN, *elf* 1,2 & 3

•SPECTRINS ESTABLISH AND MAINTAIN EPITHELIAL MEMBRANE SKELETON, CELL POLARITY, SPECIALIZED-CELL DOMAINS: AE2

GRAPHIC REPRESENTATION OF KNOWN ALTERNATIVELY SPLICED PATTERNS FOUND AMONG *elf* TRANSCRIPTS

ELF LABELING IN PRIMARY BILLARY CIRRHOSIS

ELF LABELING IN PRIMARY BILLARY CIRRHOSIS

ELF LABELING IN PRIMARY BILLARY CIRRHOSIS

ELF LABELING IN PRIMARY BILLARY CIRRHOSIS

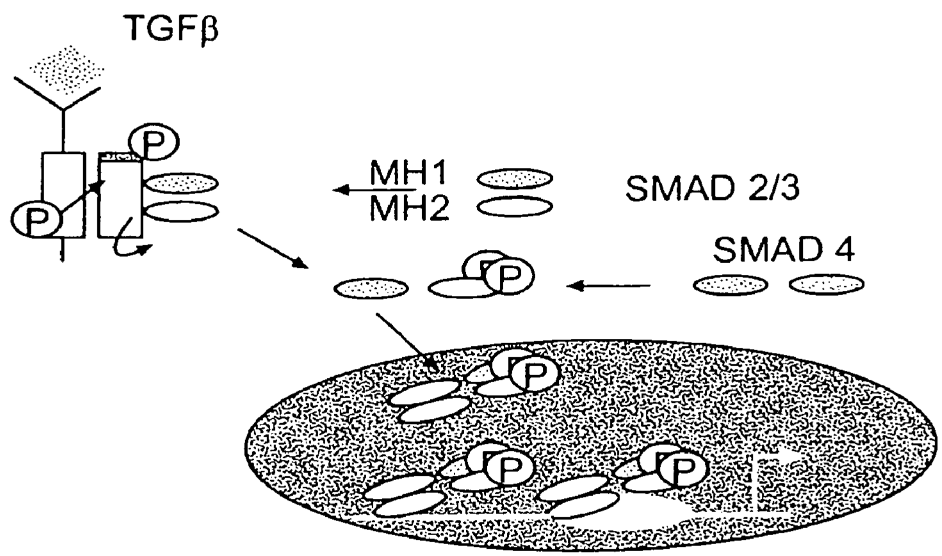
FIG. 16
α=FETO PROTEIN LABELING CELLS OF HEPATOCYTIC LINEAGE IN WILD TYPE VS. SMAD2$^{+/-}$/ SMAD3$^{+/-}$
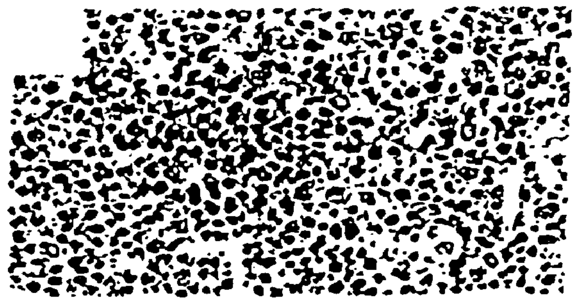
FIG. 17A
α=FETO PROTEIN LABELING CELLS OF HEPATOCYTIC LINEAGE IN WILD TYPE VS. SMAD2$^{+/-}$/ SMAD3$^{+/-}$
FIG. 17B SMAD 2 & SMAD 3 MUTANT EXPLANTS SHOWED INCREASED APOPTOSIS AND VERY FEW VIABLE HEPATIC TISSUE SMAD 2 & SMAD 3 MUTANT EXPLANTS SHOWED INCREASED APOPTOSIS AND VERY FEW VIABLE HEPATIC TISSUE HGF TREATMENT RESCUES PHENOTYPE OF MUTANT LIVER EXPLANTS AS SHOWN BY CYTOKERATIN LABELING

HB
PBD
H

HGF TREATMENT RESCUES PHENOTYPE OF MUTANT LIVER EXPLANTS AS SHOWN BY CYTOKERATIN LABELING

A
HB
H

HGF TREATMENT RESCUES PHENOTYPE OF MUTANT LIVER EXPLANTS AS SHOWN BY CYTOKERATIN LABELING

PEPTIDES AND PROTEINS FOR EARLY LIVER DEVELOPMENT AND ANTIBODIES THERETO

CROSS REFERENCE TO RELATED APPLICATIONS

This application is a divisional application of U.S. patent application Ser. No. 10/695,994, filed Oct. 30, 2003 now U.S. Pat. No. 7,202,347, which was a divisional application of U.S. patent application Ser. No. 09/431,184, filed Nov. 1, 1999 now U.S. Pat. No. 6,642,362, which was a continuation-in-part of PCT application PCT/US98/08656 filed Apr. 30, 1998, which was a continuation-in-part of U.S. patent application Ser. No. 08/841,349, filed Apr. 30, 1997 now U.S. Pat. No. 5,955,594, all of said applications incorporated herein by reference.

FIELD OF THE INVENTION

This invention relates to peptides and proteins isolated during early liver development, genes coding for these peptides and proteins, and antibodies which recognize these proteins, and to methods for their use in diagnosing and treating liver disease and other disorders.

BACKGROUND OF THE INVENTION

In the United States and other countries, end stage liver disease due to infection, genetic defects or alcoholic consumption is a major cause of widespread morbidity and mortality, causing great potential hardship and economic loss to millions of people throughout the world. In addition, numerous other diseases, including biliary problems and blood disorders, are associated with disruptions in the many functions carried out by the liver, including iron transport, hepatocyte formation and hematopoiesis. In general, severe problems associated with a breakdown of liver function are practically untreatable, and require a liver transplant as the only cure. However, in light of the great disparity between the number of patients needing liver transplants and the number of donors, thousands upon thousands of people are denied this operation, and transplantation is at the present time not a practical approach to the problem.

At the same time, the precise nature of liver development and the role of early developing liver proteins has not been and the role of early developing liver proteins has not been well understood. To date, no growth factors specific to the liver have been identified or isolated, and the precise molecular mechanisms behind hepatocyte (liver cell) formation remain to be elucidated. There thus has been a long felt need to identify and understand the changes in gene regulation and expression in the developing liver, including the determination as to which genes are switched on and off as a hepatocyte forms and a liver develops. Accordingly, isolating and identifying the genes and proteins which play critical roles in early liver development would be beneficial in understanding the effect of gene regulation and expression in the differentiating liver, and in diagnosing and treating many diseases states involving the liver and liver functions.

SUMMARY OF THE INVENTION

Accordingly, it is thus an object of the present invention to provide genes comprising the nucleic acid sequences encoding early liver developmental proteins, including the liver proteins known as elf 1-3, liyor-1 (145), pk, protein 106, and praja-1.

It is further an object to provide isolated and purified early developing liver proteins encoding by the above genes.

It is still further an object to provide proteins which are characteristic of early liver development and peptides from said proteins and peptides, and to raise antibodies from said proteins and peptides which will be useful as markers, and will be useful in methods of identifying such peptides and proteins, tracing hepatocyte lineage, and treating liver disease.

It is still further an object to use the early developing liver proteins of the present invention to provide liver-specific growth factors for application in diagnosis and treatment of liver disorders.

It is still further an object to provide methods of diagnosing and treating end stage liver disease using the early developing liver proteins of the present invention.

It is even further an object to provide methods of diagnosing and treating other liver disorders and other diseases, including carcinoma, degenerative neurological disorders, anemia, and ataxia, using the early developing liver proteins of the present invention.

These and other objects are achieved by virtue of the present invention which provides genes coding for various proteins which are involved in the differentiation of the developing fetal liver, including the proteins known as elf 1-3, liyor-1 (145), pk, protein 106, praja-1, and a number of other stage-specific genes coding for early-developing liver proteins, and methods for their use in diagnosis and treatment of a variety of liver diseases and other disorders.

BRIEF DESCRIPTION OF THE DRAWINGS

The present invention will now be described in detail with respect to preferred embodiments thereof, which are to be taken together with the accompanying drawings, wherein:

FIGS. 1A-1B represent the nucleic acid sequence encoding the liyor-1 (145) protein in accordance with the present invention.

FIGS. 2A-2E represent the nucleic acid sequence encoding the elf-1 protein in accordance with the present invention.

FIGS. 2F-2I represent the nucleic acid sequence encoding the elf-2 protein in accordance with the present invention.

FIG. 2J represents the nucleic acid sequence encoding the elf-3 protein in accordance with the present invention.

FIGS. 3A-3B represent the nucleic acid sequence encoding the praja-1 protein in accordance with the present invention.

FIG. 4A-4B represent the nucleic acid sequence encoding the pk protein in accordance with the present invention.

FIG. 5 represents the nucleic acid sequence encoding the 106 protein in accordance with the present invention.

FIGS. 6A-6B represent the nucleic acid sequence encoding gene 20 in accordance with the present invention.

FIG. 7 represents the nucleic acid sequence encoding gene 36 in accordance with the present invention.

FIG. 8 represents the nucleic acid sequence encoding gene 41 in accordance with the present invention.

FIG. 9 represents the nucleic acid sequence encoding gene 112 in accordance with the present invention.

FIG. 10 represents the nucleic acid sequence encoding gene 114 in accordance with the present invention.

FIG. 11 represents the nucleic acid sequence encoding gene 118 in accordance with the present invention.

FIG. 12 represents the nucleic acid sequence encoding gene 129 in accordance with the present invention.

FIG. 16 is a schematic view of the role of SMAD proteins as intracellular mediators of TGF-β and activins.

FIG. 17 depicts α-feto protein labeling cells of hepatocytic lineage in wild type vs. $smad2^{+/-}/smad3^{+/-}$.

DETAILED DESCRIPTION OF THE PREFERRED EMBODIMENTS

Figure 13:
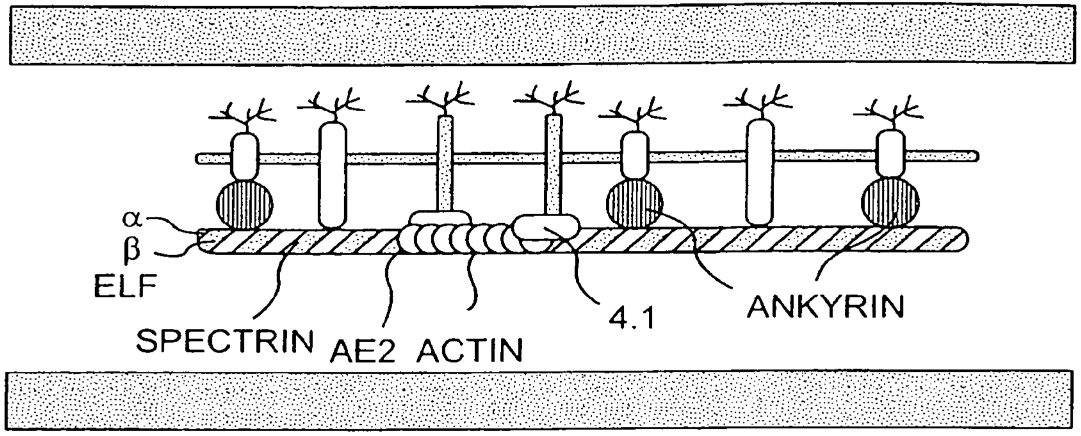
FIG. 13 is a depiction of the membrane skeleton of the ELF protein of the present invention.

In accordance with the present invention, early developing liver proteins and the genes coding for them have been isolated and sequenced, and these genes and proteins can be utilized to diagnose and/or treat a wide variety of liver disorders and other ailments. In general, the present invention arose from the investigation of liver formation during embryogenesis when the liver and other organs are in transition from an undifferentiated state to a differentiated one. This setting captures the phases of liver formation beginning with ordinary sets of endodermal cells. In addition, the early steps in tissue differentiation are closely related to the process of oncogenesis and tissue repair, and thus the isolated early developing liver proteins obtained in accordance with the present invention should have implications for diagnosis and treatment of a range of diseases from end stage cirrhosis to hepatocellular carcinoma and many other disease conditions.

In the identification and isolation of the liver proteins of the present invention which are useful in early hepatocyte formation, the first step that was taken was to “capture” and analyze gene expression at different stages of early liver formation, particularly at those stages that emerge in the range of about days 9 through 14.5 in the mouse. In this regard, four embryonic liver cDNA libraries were constructed, such as at days 10.0, 11.5, 12.5 and 14.5 post coitus, and after subtractive hybridization, isolation of a group of stage-specific, liver restricted clones were isolated. As will be set forth in more detail below, sequence analysis has revealed that these clones encode a series of early developing liver proteins, which are generally “stage specific”, i.e., they appear only at specific stages of development and not other stages, including elf proteins 1-3, liyor-1 (145), pk, protein 106, proteins coded for by genes 20, 36, 41, 112, 114, 118 and 129, and praja-1, as will be described further herein.

The initial project to identify and isolate developing liver proteins had four main objectives: (1) to construct early embryonic liver libraries; (2) to screen and characterize these early embryonic liver libraries with a group of probes comprising known growth factors (IGF-I, IGF-II, and IGFBP-2) and transcriptional activators (C/EBP and LFB1), known to be expressed in the developing liver; (3) to carry out subtractive hybridization utilizing these cDNA libraries and analyze subsequent subtracted clones for stage specificity by southern blot hybridization, sequence, transcript size, abundance, and tissue distribution; and (4) to develop a functional assay for these subtracted genes using embryonic liver explant cultures.

With regard to the main objectives of the invention, it was decided to focus on the four stages of liver development, particularly around days e10, e11, e12 and e14 (embryonic days post coitus) in developing mice. These four stages are defined developmental time points representing phases of liver development from undifferentiated mesodermal/endodermal cells to a well developed and differentiated fetal liver. These stages have generally been categorized as follows: (1) at around e9-10, a change in cell polarity occurs; (2) at around e10.5-11, invasion and migration of endodermal cells into surrounding mesenchyme occurs; (3) at around e11.5-12, pseudolobule formation, cords of hepatocytes form together with early sinusoids; and (4) at around e12.5-e14.5, the liver is marked by hematopoietic foci and fully differentiated fetal hepatocytes. cDNA libraries representing these stages would therefore represent “captured” mRNA species expressed in greater abundance during critical time periods for hepatocyte formation, enabling their isolation and providing a method for analyzing the changing pattern of gene expression during liver development.

Another aspect of the present invention is the development of useful methods of diagnosis and treatment of liver disorders and other diseases made possible by the identification and isolation of the genes for early developing liver proteins of the invention and the expression of those genes. In accordance with the investigations made regarding these early developing liver proteins, it is clear that the different genes and proteins identified are important for different aspects of liver development and can thus be utilized in treatments of the appropriate disease. During embryogenesis, the liver generally develops from a foregut diverticulum, and comprises four main cell types: the first is the hepatocyte, or endodermal lineage; the second are biliary tree canalicular cells or bile duct cells, the third are hematopoietic cells, and the fourth are the Kupffer cell/Ito cells. As will be set forth below, of the early developing proteins isolated and obtained in accordance with the present invention, it is believed that the elf proteins are important for the formation of the biliary tree, as shown by antisense experiments; praja-1 appears to be important for iron transport and essential for hepatocyte formation as well as hematopoiesis; liyor-1 (145) and pk appear to be important in Ito cell formation and fibrosis.

Accordingly, in accordance with the invention, it is contemplated that elf proteins 1-3 will be useful in the treatment of disorders such as cholestasis, biliary stones, hepatic obstruction, stricture, primary biliary cirrhosis and primary sclerosing cholangitis. In addition, the proteins praja-1, liyor-1 (145) and pk will be useful in treating end stage liver disease, anhidrotic ectoderm dysplasia, hepatocellular carcinoma, as well as anemia, such as sideroblastic anemia, ataxia, e.g., spinocerebellar ataxia, degenerative neurological disorders, anhidrotic ectoderm dysplasia, and hemochromatosis.

Even further, it has also been discovered that the protein praja-1 has been identified in cancerous colon tissue, which normally does not produce this protein. Accordingly, it is contemplated that in accordance with the present invention, a method of detecting and diagnosing colon cancer is provided wherein colon cells or tissues are taken from a patient being tested, and these cells or tissues are screened to determine the presence or absence of the praja-1 protein. Identification of praja-1 in the colon cells or tissues will allow for a determination of whether the cells are cancerous since praja-1 will generally not be detectable in non-cancerous colon cells.

In the preparation of cDNA libraries in conjunction with this invention, it was necessary to utilize the four developmental stages discussed above in order to isolate key early developing liver proteins that affect the formation of hepatocytes and the liver. Although these studies were performed on mice, the relevance of the stages of liver formation to human development is shown in the following summary of these investigations:

(1) Day 10 Post Coitus (e10, 34-39 Somites) (Human Day 27):

In the mouse, the primary liver diverticulum appears during the 10th day of gestation. It develops from a foregut indentation in the endoderm which arises at e7, at the boundary between the embryonic and extraembryonic region, anterior to the developing heart rudiment. At this stage, although the cells are committed to the formation of fetal hepatocytes, they are still epithelial in nature and the liver diverticulum is not viable in the absence of the surrounding heart mesenchyme. As this is the earliest stage possible when hepatocytes are undifferentiated, it was considered to be of great importance: some cells are poised to differentiate into hematopoietic cells and others into hepatocytes. Accordingly, a day 10.0 library was constructed in lambda Unizap, and no prior group had ever constructed a cDNA liver library at this stage.

(2) Day 11.5 Post Coitus (e11.5, 40-44 Somites) (Human Day 32):

This stage is characterized by rapid growth of the liver. Soon after the formation of the hepatic bud, the endodermal cells proliferate, disrupting the membrane separating the epithelium from the septum transversum, with the epithelial cells migrating into the mesenchyme. The liver at e11.5 consists of broad hepatic cords separated by large sinusoids containing nucleated erythrocytes. Hematopoietic foci are found intermingled with the hepatic cords. A cDNA library was constructed in lambda gt10 and lambda Zap from embryonic livers obtained at this stage, since although cells are proliferating rapidly, they still have not attained a fully differentiated fetal state.

(3) Days 12.5-13.0 Post Coitus (e12.5, Human Days 35-45) (Embryo Size: 7-9 mm):

This stage is easily recognized by early signs of finger development as well as by the anterior indentation of the footplate. At this stage, the liver is well developed, all lobes being clearly visible; it contains many megakaryocytes as well as cells with erythropoietic activity. A CDNA library at e12.5 was constructed in lambda gt10 and lambda Zap as this was the earliest stage where fully differentiated fetal hepatocytes are seen.

(4) Day 14.5 Post Coitus (e14.5, Human Days 51-57) (Embryo Size: 20-32 mm):

At this stage, individual, separated forefoot fingers can be seen; hair follicles in the skin can be recognized and the umbilical hernia is very conspicuous. This stage represents a well differentiated fetal liver containing scattered blood-forming foci. A CDNA library of this stage was constructed in lambda Unizap in order to facilitate subtraction with the day 10 library which was also constructed in lambda Unizap (Stratagene).

(5) Adult Mouse Liver:

At birth, day 19, there is a major "switch" in the expression of a large number of genes. From now until the stage at which adult liver is formed, enzyme synthesis of the urea cycle and gluconeogenesis are upregulated. Adult liver is no longer a center for hemopoietic activity except in pathological situations and hepatocytes do not enter de-differentiated states, though the liver still has regenerative capacity as seen in partial hepatectomy.

In conjunction with each of these stages of development, RNA was recovered from each stage, and the quality of the RNA obtained following dissection was assessed by Northern blot analysis using mouse Beta Actin from the Chiba Cancer Center Research Institute, Chiba, Japan. Table 1 shows the RNA yields obtained. The cDNA library construction at days e11.5 and e12.5 of the embryonic liver was carried out by conventional techniques, and the libraries of the day e10.0 and adult mouse liver were obtained using the Stratagene Unizap cDNA library kit. The cDNA inserts for e10.5, e11.5, e12.5, e14.5 post coitus stage mice and the adult mouse liver were size selected on a Biogel A150 column (>500 bp) prior to ligation to the vector.

Qualitative analysis of cDNA libraries utilizing known developmentally regulated cDNAs were carried out in order to establish developmental profiles of important "early" genes that are significant in development, and these libraries were then screened with a specific number of probes. The following probes were obtained and used for screening these libraries, including: Insulin like growth factor I (IGF I), obtained from Dr. Derek le Roith (NIH); Insulin like growth factor II (IGF II) and IGF II binding protein-2(BP-2) both obtained from Dr. Matt Rechler of NIH; LFB 1 obtained from Drs. Monaci, Nicosia and Cortese of EMBL in Heidelberg, and the C/EBP probe from Dr. Darnell of the Rockefeller University in New York, N.Y.

The data shows that IGF I was not detected in any of the embryonic libraries, while IGF II was detected in increasing clone frequency from e6.5 to 8.5 (8 at e6.5, 8 at e7.5 and 38 at e8.5—data not shown) and was also detected in the e10.0 and e12.5 libraries (3 at e10.0 and 4 at e12.5—see Table 3). IGF II was not detected in the adult liver library. Interestingly, BP2 clone frequencies are similar to IGF II in the early e6.5, e7.5 and e8.5 libraries (data not shown), but in the liver cDNA libraries the clone frequencies differed, for BP2 only one clone per 100,000 being detected at e10.0 and e11.5, while 7 were detected in the Adult Liver Library compared to the greater numbers for IGF 11. This implied that its temporal and spatial expression in the embryo and fetus is different from IGF 11 and this was subsequently confirmed by in situ studies. LFB I was detected in the e12.5 library, but at one clone per 100,000 screened, which implied that it is not present in mitogenic cells, but that its level was regulated and increased from birth onwards. C/EBP was not present in the e6.5, e7.5, e8.5 or e10.0 libraries (data not shown) but was suddenly detected at day e11.5 and e12.5 in low abundance (about 2 clones/100,000 at e11.5 and 5 at e12.5), implying that while it is expressed, its level also may be regulated, albeit downward, in embryonic stages. Lastly, Beta Actin was used as a reference: all seven libraries had similar Beta Actin frequencies from 120-300/100,000 clones which is considered representative of such embryonic libraries.

Next, identification of stage specific clones by subtractive methods was carried out, and two subtracted libraries were then constructed. Two rounds of subtraction were carried out, and the resulting subtracted libraries comprised 64 clones (e11.5-12.5), and 174 clones (e10.5-14.5). Further characterization of these clones was carried out as follows: (1) Southern hybridization; (2) sequencing; (3) Northern analysis; (4) Zoo blot analysis; and (5) In vitro translation of protein.

In the Southern blotting of these clones, thirty-four clones were shown to be stage specific and not containing mitochondrial, ribosomal and globin sequences. DNA sequencing of these thirty-four stage specific clones was carried out in order to identify clones bearing homology to known developmental genes (such as cell polarity genes, homeobox genes, etc.), and the first 400 base pairs of each clone were sequenced. A detailed analysis was then carried out with respect to some of the clones which form a part of the present invention, including liyor-1 (145), protein 106, pk, and praja-1, since these clones exhibit true stage specificity and appear to belong to a set of genes encoding signal transduction proteins, which are of great interest in development currently, due to studies demonstrating their importance in cell lineage. Other stage-specific proteins which are coded for by genes in accordance with the invention are discussed further below. Studies carried out with regard to proteins such as praja-1 and elf, as well as other early developing liver proteins, have elucidated the sequence of these proteins, as will be set forth in more detail below.

As an example of the tests used to elucidate the developmental expression of these liver proteins, the protein liyor-1 (145) was tested to determine whether these transcripts are differentially expressed during development, specific for mesoderm or endoderm derived tissues, or are expressed in adult mouse and human organs. Accordingly, tissues from mid-gestational embryos were analyzed to determine the role of 145 in liver development. In these tests, tissues were dissected from day 11 onwards, as it was at this stage that discrete hepatic, cardiac and other tissues could be dissected with ease, with subsequent RNA isolated being of good quality.

RNA hybridization with liyor-1 (145) DNA in different mouse tissues was studied by using polyA RNA obtained at various developmental stages using a 32P-labeled 1.1 Kb insert representing protein 145. The specificity of the developmental changes in the steady state levels of 145 was evaluated by also measuring the relative levels of Actin. This revealed a 2.4 Kb transcript at high stringency washes. Scanning densitometry of the respective bands revealed that maximal expression of 145 occurred in liver and heart, less so in other tissues, but specifically on day 11 and in decreasing abundance at days 12.5 and 14.5 (when Northerns were developed 1-2 months later).

Further characterization of the distribution of protein 145 RNA in adult tissues and its conservation in evolution has involved RNA analysis of adult mouse and human tissues. The protein 145 hybridizes to adult liver, kidney and testis as a 2.4 Kb transcript in liver and kidney and a 2.6 Kb transcript in adult testis, in very low abundance: both blots were developed after being exposed to film for over a month at −70° C. Similar tests conducted with regard to the elf protein and the nucleic acid coding for it showed that elf DNA is generally conserved across many different species, including human, monkey, rat, mouse, dog, cow, chicken and yeast, and is represented in all species studied except rabbit.

Finally, in accordance with the invention, a functional assay was established for subtracted genes with the goal to establish mouse embryonic liver explant cultures in the laboratory, as this is usually considered the major hurdle for antisense experiments due to the need to dissect extremely small tissue sections at day 9.5 when the liver bud is 0.2 mm. In this regard, the interactions of the neighboring cardiac mesoderm and foregut endoderm were studied and the subsequent changes in cell type specific gene expression were characterized, particularly with respect to alpha-fetoprotein and albumin expression, and partially with respect to epithelial basement membrane components. Methods of culturing liver explants in accordance with the invention are described below. The results obtained in these tests have shown that when cultured in the complete absence of mesodermal derivatives, hepatic endoderm deteriorates rapidly. Only 2 out of 15 such liver explants survived. Hematoxylin and eosin staining showed a necrotic endoderm with no apparent signs of hepatic differentiation. When associated with the surrounding mesoderm particularly cardiac mesoderm (en bloc dissections), the endodermal cells had proliferated and invaded the mesodermal strands. Hepatocytes were seen to be organized in cords separated by sinusoids with pseudo-lobule formation. All 15 out of 15 cultures from en bloc dissections were completely viable. These studies confirm prior explant studies demonstrating the necessity of surrounding mesoderm for liver formation.

Accordingly, cDNA libraries have been constructed for the four main stages of liver development, e10, e11.5, e12.5, e14.5 and for adult liver in the mouse. These have been shown to be truly representative of their respective mRNA species, by meticulous analysis utilizing initial RNA blot analysis, size fractionation, quantitative, and qualitative analysis. Northern analysis confirmed the stage specificity, and restricted expression of their transcripts: for 145 this comprised a 1.35, and 2.37 Kb transcript restricted to midgestational brain and liver tissue, and adult mouse and human Northern blot analysis revealed 145 transcripts in extremely low abundance in liver, kidney, testis. Further tests with regard to protein 145 reveals its sequence identity of 53% (20 S.D.'s) to rat Phospholipase C-γ (PLC-γ), and amino acid alignment of conserved section of 145 to PLC-γ identifies a split pleckstrin homology (PH) domain. Protein 145 (liyor-1) bears 99% identity at the amino acid level to the PH domain at the amino terminus of PLC-γ. The PH domain is an area of 100 amino acids that has been found in a number of proteins including serine/threonine kinases, GTPase activating proteins, phospholipases and cytoskeletal proteins, and is thought to be involved in signal transduction. Nuclear magnetic resonance spectroscopy has revealed that the PH domain of P-fodrin is an electrostatically polarized molecule containing a pocket which may be involved in binding of a ligand. Of immense interest is the fact that this pocket is related to the peptidyl-prolyl-cis-trans-isomerase FKBP in which this pocket is involved in the binding of the macrocyclic compound FK506. Accordingly, it is contemplated that protein 145 may indeed bear a pocket for 'natural' ligand similar to FK506 and thus appears to be a potential factor for hepatocyte differentiation.

PLC-γ is regulated by a combination of SH2-domain dependent complex formation with tyrosine phosphorylated receptor tyrosine kinases, and its subsequent phosphorylation on tyrosine residues. An unique feature of PLC-γ and protein 145 is that both contain a split PH domain, which in the case of the PLC fills the gaps between the SH2-SH2-SH3 region and the surrounding X and Y catalytic domains. The SH2 domains mediate the high affinity interaction of PLC-γ with activated growth factor receptors such as epidermal growth factor (EGF) or platelet derived growth factor (PDGF) receptor. The PH domain similarly may be utilized as a specialized noncatalytic domain directing complex formation between protein kinases and their presumptive targets during liver development. In addition, the area of complete identity and split PH domain in 145 and PLC-γ is conserved in a number of other proteins through to TOR2, an essential yeast PI 3 kinase, and to v-abl. A parallel can be drawn to the SH2 domain: that proteins associating with activated growth factor receptors have quite distinct enzymatic properties, are structurally unrelated within their catalytic domains, yet contain a similar noncatalytic domain of approx 100 amino acids, called the src homology (SH) region 2. The SH2 domain was first identified in non receptor protein tyrosine kinase like Src and Fps, by its apparent ability to interact with the kinase domain and phosphorylated substrates. It is believed that during the evolution of cellular signaling mechanisms, the acquisition of SH2 domains conferred on PLC-γ and GAP the capacity to interact with transmembrane tyrosine kinases and therefore couple growth factor stimulation to PI turnover and the kinase pathway. PH domains are similarly conserved and may be utilized in the same way that SH2 domains are.

As indicated above, the protein liyor-1 (145) appears to be important in Ito cell formation and fibrosis, and is thus thought to be useful in treating end stage liver disease as well as other conditions including hepatocellular carcinoma, anemia, ataxia, and hemochromatosis. It is contemplated that the use of the protein Liyor-1 will be by administering to a suitable patient an amount of this liver protein effective to treat the specific condition of that patient, and this would be carried out using conventional means and regimens well known to one skilled in this art. The sequence of Liyor-1 which was determined using the cDNA libraries of the present invention is shown in FIGS. 1A-1B, and suitable amounts of the liyor-1 (145) protein may be prepared in a conventional manner by expressing by recombinant or other means the nucleic acid coding for the 145 protein, after which the protein can be isolated and/or prepared into substantially pure form as needed. In addition, the 145 protein may be administered with any other suitable compound normally utilized for administration into a patient, such as a suitable pharmaceutically acceptable carrier.

As indicated hereinbelow in the examples, other genes for early developing liver proteins in accordance with the present invention have been isolated and sequenced, including the genes coding for the elf proteins, praja-1, pk protein, protein 106, and genes 20, 36, 41, 112, 114, 118 and 129. With regard to the elf proteins, these proteins were studied by analyzing mRNA from tissues from mid-gestation embryos. Tissues were dissected from day 11 onwards, as it was at this stage that discrete hepatic, cardiac and other tissues could be dissected with ease, and the subsequent RNA that was isolated was of good quality. RNA hybridization with elf DNA in different mouse tissues was studied by using polyA RNA obtained at various developmental stages using a $^{32}$P-labeled 1.1 Kb insert representing elf. The specificity of the developmental changes in the steady state levels of elf was evaluated by also measuring the relative levels of Actin. This revealed a 2.4 Kb transcript at high stringency washes. Scanning densitometry of the respective bands revealed that maximal expression of elf occurred in liver and heart, less so in other tissues, but specifically on day 11, and in e12.5 and e14.5 in decreasing abundance (when Northerns were developed 1-2 months later).

In situ hybridization was then used to confirm elf expression in 11.5 heart and liver as well as to determine its expression pattern during earlier liver development, as will be set forth below in the Examples. The liver bud, which originates from foregut endodermal cells, grows into the septum transversum at the 9th day of gestation (13-20 somite stage). Between days 10.5 to 11.0 post coitus, a considerable degree of differentiation occurs: The liver enlarges substantially over this period, this increase in volume being due to the invasion of the mesenchyme of the septum transversum by the hepatic cords, and the initiation of hematopoietic activity in the liver. At day 9.5, a strong labeling of elf becomes apparent in the heart, and the pattern appears to be trabecular, including the wall of the cardiac anlage. A section of the sino-atrial chamber wall also shows a high intensity of elf expression. The surrounding tissue, particularly the caudal liver bud region does not show the presence of silver grains.

At the next stage, day 10.5, silver grains clearly highlight the developing liver, which appears as a horizontal structure (L) in this section. At this stage, the signalling is weakening in the developing heart tissue. The surrounding tissues are remarkable for the absence of silver grains. At day 11.5, a strong labeling of elf becomes apparent in the liver, which is larger in size. The heart at this stage only shows a weak signal posteriorly. As a control, in addition to sense probes, a riboprobe to alpha fetoprotein outlines the developing embryonic liver at days 11-12.

A comparison of the day 9.5 and 10.5 embryos, demonstrates a temporal and spatial expression of elf: the temporal gradient of a rise and fall of elf expression in the heart can be inferred from the strong staining in the developing heart at day 9.5 followed by a weaker staining at the next stage (day 10.5). Simultaneously, liver expression increases. The spatial gradient is apparent where silver grains increase in density on moving from the developing heart to the liver: at day 10.5, antisense RNA probes from elf cDNA hybridized specifically to day 9.5 cardiac mesenchymal tissue; expression at day 10.5 being restricted to cardiac and hepatic tissue, with elf expression finally being restricted to the liver in later 11.5 day embryos. Of note, elf expression was seen in embryonic livers at later stages (days 12.5, 14.5 p.c.), but only in decreasing abundance: the message being detected in these later stages when Northerns and in situs were developed a considerable time later. Sense probes to elf did not hybridize to any tissues. This indicates that ELF expression is not a sudden "on" "off" phenomenon, but more of a gradient pattern: consistent with the expression pattern of brain beta spectrin.

Alpha fetoprotein antisense RNA probes hybridized specifically to 11.5, 12.5, 14.5 embryonic mouse liver tissue, which is in agreement with previous studies of mRNA isolated from embryonic liver samples. The earliest stage that we were able to detect alpha-fetoprotein mRNA by in situ hybridization was at 10.5-11.0 days of gestation. Similar experiments with albumin mRNA have shown it to be expressed at day 9.5 in clusters of cells arising from foregut epithelium and in cords of cells seen to be invading the septum transversum. In experiments with alpha-fetoprotein, the liver was labeled at all subsequent stages (day 11 onwards), and, upon histological examination appeared to occur primarily in the endothelial cells. Hematopoietic cells appeared retractile but did not contain the hybridization grains that were visible over the alpha-fetoprotein positive cells. These experiments show that elf mRNA is localized to early embryonic heart, and then moving to e11 liver.

Next, it was determined that elf was a marker for the mesodermal component of liver formation. As Northern analysis had revealed elf expression to occur in day 11.5 heart and liver tissue, in situ localization was performed to investigate whether elf expression was restricted specifically to mesodermal tissue from the heart and the liver and was then compared to the endothelial expression of alpha fetoprotein. The main regions of mesoderm in the developing embryo are dorsal (somitic), intermediate, and lateral. Specifically, lateral plate mesoderm comprises somatic tissues (pleura, pericardium, peritoneum and limb bud), and splanchnic tissues (heart, epicardium, myocardium, connective tissue and smooth muscles of viscera and blood vessels, hemangioblastic tissue, adrenal cortex and spleen). The developing heart, at day 9 (13-20 somites), appears to be only region within the embryo where the endothelial elements of the circulation are surrounded by a vessel wall. The walls of the common ventricular and atrial chambers show an increasing degree of trabeculation. The space between the endothelial and myocardial elements is filled with loose mesenchyme called cardiac jelly. In situ hybridization of days 9 and 10 embryonic heart tissue using elf antisense riboprobes showed high levels of labeling to both the atrial and ventricular regions, highlighting the trabeculation.

Hepatic mesenchyme also originates from lateral plate mesoderm. The septum transversum part of the hepatic mesenchyme originates from the splanchnic mesoderm of the precardiac area and this is considered to be responsible for the subsequent differentiation of hepatocytes. However, tissue explant experiments have demonstrated that all derivatives of the lateral plate can replace hepatic mesenchyme for these later events. The initial experiments have shown that migrating endoderm must interact with mesenchyme for the former to differentiate into hepatocytes and recent studies investigating albumin mRNA expression, an indicator of hepatocyte differentiation, have confirmed these features; Initial expression of albumin mRNA occurs during the invasion of the septum transversum, when foregut endodermal cells clearly contact cardiac mesenchymal tissue. Similarly, primer extension analysis of albumin transcription has shown that the start site of transcription to occur at day 10.5 with a 15-20 fold increase in albumin mRNA upon liver organ formation by day 12.5. In our experiments using alpha fetoprotein as a marker for differentiated hepatocytes, it was obvious that while alpha fetoprotein expression is restricted to the later endodermal component of liver development, elf expression seems to occur in the loosely organized, lighter staining mesenchymal cells, initially cardiac mesenchyme (at day 9.5), then in both cardiac and hepatic tissue (at day 10.5) and then restricted to liver tissue (day 11.5 onwards); elf expression then decreases in abundance upon full embryonic liver formation. Examination of later histological sections (days 11 onwards) demonstrated a diffuse distribution of grains, and the hybridization signal with elf appeared to be localized in the perisinusoidal cells, but not in the hepatocytes.

That elf is expressed in early cardiac mesoderm, with subsequent expression being limited to hepatic mesoderm, indicates that this is a novel marker for the mesodermal component of liver development. Molecular markers have been invaluable in the dissection of inductive events in embryological studies. For instance, in *Xenopus*, vg-1, a member of the TGF-Beta family, now considered to be the strongest candidate for dorsal mesoderm induction, was in fact originally isolated by differential screening of mRNAs localized in the vegetal hemisphere of developing *Xenopus* eggs. Activins and other genes belonging to the TGF-Beta family such as vg-1, as well as wnt and BFGF families, represent components of the cascade leading to the commitment to particular mesodermal fate and all are strong candidates as mesoderm-inducing factors. Yet of these, only vg-1 has been demonstrated to be localized to the vegetal cells, the blastomeres responsible for mesoderm induction in vivo. Specific localization of vg-1 was vital and responsible for the persistence required in investigating its role as the inductive agent in mesoderm formation. Similarly, in isolating putative inductive agents required for liver formation, a key step is the localization of a new mRNA isolated from the embryonic livers. Accordingly, it is contemplated that elf and its associated regulatory genes will be of enormous potential benefit as a liver growth factor.

Further characterization of elf has involved RNA analysis of adult mouse and human tissues, and it was determined that elf hybridizes to adult liver, kidney and testis as a 2.4 Kb transcript in liver and kidney and a 2.6 Kb transcript in adult testis, in very low abundance: both blots were developed after being exposed to film for over a month at −70° C. Genomic DNA analysis of elf expression in DNA (genomic) from human, monkey, rat, mouse, dog, cow, rabbit, chicken and yeast indicates that elf is conserved across the species, being represented in all except rabbit DNA.

In vitro transcription and translation of elf, the latter using nuclease-treated rabbit reticulocyte lysate (promega) has revealed a 34 Kd protein, which is as predicted by the elf insert size and indicating that this insert is in frame for the coding sequence for a specific protein. These studies have established the principle that specific mesodermal mRNAs are localized in a way that guarantees their subsequent segregation to specific mesodermal tissue, in this case the presumed mesodermal component of the liver as shown by embryonic explant studies.

The elf protein has been sequenced, and it has been determined that at least three specific elf protein genes can be identified during early liver development. The sequences for these genes, known as elf-1, elf-2, and elf-3, are shown in the FIGS. 2A-2E, 2F-2I and 2J, respectively. As indicated above, it appears that the elf proteins 1-3 are probably important for the formation of the biliary tree during early liver development. Accordingly, it is contemplated that in accordance with the present invention, the elf proteins will be useful in treating various disorders associated with liver function, including cholestasis, biliary stones, obstruction, stricture, primary biliary cirrhosis, and primary sclerosing cholangitis. As would be readily apparent to one skilled in the art, methods of treatment using the elf proteins would comprise administration of an amount of an isolated elf protein that is effective to treat the specific disease condition described above. As also would be apparent, the elf proteins themselves can be prepared in a number of suitable ways by expression from the nucleic acid sequences indicated at FIGS. 2A-2J, including recombinant methods of producing these proteins, followed by separation, isolation and/or substantially purifying the elf proteins. The elf proteins once obtained in this manner can be put into any suitable form that is acceptable for use with patients. In addition, any of these three elf proteins may be administered with any other suitable compound normally utilized for administration into a patient, such as a suitable pharmaceutically acceptable carrier.

Another protein that has been identified and isolated in accordance with the present invention and which is contemplated to be used in a variety of therapeutic methods is known as praja-1. Praja-1 has now been studied in conjunction with the examination of early developing liver proteins, and an analysis of the amino acid translation revealed the presence of a COOH-terminal RING-H2 motif, which is a zinc finger variant. Additionally, Northern blot analysis of RNA from adult mouse showed expression of 3.1, 2.6, and 2.1 kb transcripts in liver, brain, and kidney, and an additional 2.3 kb transcript in testis. Expression of praja-I is also apparent in a colon cancer cell line, SW 480, and as set forth below, it is also contemplated that the praja-1 protein will be a useful marker in early detection of colon cancer.

It has also been learned that praja-1 maps to chromosome X, at about the 36 cM position. Other genes mapping to this general region include moesin (Msn), androgen receptor (Ar), interleukin-2 receptor gamma (IL-2rg), X-linked zinc finger protein (Zfx), and tabby (Ta). The syntony and conserved gene order between mouse and human X chromosomes allows comparison with human disease genes in the region. Human diseases in this region with mesodermal involvement include anhidrotic ectoderm dysplasia (eda) and sideroblastic anemia with spinocerebellar ataxia (asat), and it is thus contemplated that in accordance with the present invention, praja-1 will be useful in treating these disease conditions, as well as degenerative neurological disorders.

In vitro expression of praja-1 has shown that the translational product, which ran as two closely spaced bands of Mr=55.6 and 56.9 kD, is larger than the predicted ORF size of 47.4 kD. One possible explanation is that the expression product is very acidic, and acidic proteins such as granins are known to give anomalously high Mr on SDS-PAGE. The presence of two products suggests translation initiation at a second, internal ATG codon, such as at Met-19.

In addition, antisense studies to praja-I demonstrated that praja-I is essential for liver architecture formation. Preliminary antisense studies were performed at 1.25, 2.5 and 5 mfn concentrations, utilizing two different ODNs to praja-1. In these tests, liver and block explants were treated with these antisense ODNs compared with control (scrambled, sense or no ODNS). The results showed that control livers were generally larger than the antisense-treated livers, and control blocks showed early hepatocyte growth, cartilage growth, and very preserved bile ducts. Both livers and blocks treated with either antisense ODN to praja-1, showed minimal hepatocyte growth, cell necrosis, yet preservation of cartilaginous tissue, in a dose dependent manner.

In praja-1, aside from the RING-H2 finger, the stretch of thirty-four COOH-terminal amino acids just past this motif is especially rich in proline residues (17.6%); and, as stated, the protein in general is very acidic. Proline-rich domains are found in several mammalian transcription factors, such as that at the COOH-terminus of transcription factor CTF. Proline-rich regions and also acidic regions are likely to function in contacting other proteins. When considering the praja-I sequence as a whole, the rat Neurodap1 gene has the highest similarity. Neurodap1 is expressed abundantly in rat brain, with much smaller amounts in heart and skeletal muscle. Though praja-I likewise shows expression in brain, unlike Neurodap1 (which is a larger 4.8 Kb transcript), it also expresses in liver and kidney. The subcellular localization of Neurodap1 was shown to be concentrated around the endoplasmic reticulum (ER) and golgi of the cerebral cortex and facial nucleus, and especially in the postsynaptic density region of axosomatic synapses. Based on its subcellular localization, plus the presence of the RING-H2 finger, Neurodap I is probably linked to the secretory or protein sorting. This similarity to Neurodap1 indicates that praja-I is most likely involved in protein-protein interactions, possibly in a protein sorting or secretary pathway involved during hepatocyte formation.

The gene coding the praja-1 protein has been sequenced, and this nucleic acid sequence is shown in FIGS. 3A-3B. As indicated above, it appears that the praja-1 protein is probably important for iron transport, and essential for hepatocyte formation as well as hematopoiesis. Accordingly, in accordance with the present invention, praja-1 can be used in methods of diagnosing and treating diseases such as end stage liver disease, iron storage disorders, hepatocellular carcinoma, as well as anemia, such as sideroblastic anemia, ataxia, such as spinocerebellar ataxia, and hemochromatosis. As would be recognized by one skilled in the art, these methods of treatment would involve administering of an effective amount of the praja-1 protein to the patient afflicted with one of the disease conditions set forth above. In addition, the isolation of the praja-1 protein could be obtained by expression of the nucleic acid sequence indicated at FIGS. 3A-3B which codes for the praja-1 protein, and this protein can be produced from its nucleic acid sequence in any suitable manner well known in the art such as recombinant means. Once isolated in this manner, the praja-1 protein can be obtained in a desired form, such as in substantially purified condition, and can be incorporated into any suitable mode of treatment that would be compatible with the patient in need of such treatment. In addition, the praja-1 protein may be administered with any other suitable compound normally utilized for administration into a patient, such as a suitable pharmaceutically acceptable carrier.

Even further, as indicated above, it has also been discovered that the protein praja-1 has been identified in cancerous colon tissue, such as in colon cancer cell line SW 480, which normally does not produce this protein. Accordingly, it is contemplated that in accordance with the present invention, a method of detecting and diagnosing colon cancer is provided wherein colon cells or tissues are taken from a patient being tested, and these cells or tissues are screened in any suitable manner which would identify the presence or absence of the praja-1 protein in the tested cells or tissues. In this manner, the identification of praja-1 in the colon cells or tissues from the patient will be indicative of a cancerous condition in the colon cells or tissues, and thus the present invention will provide a simple and effective method for determining at an early stage, when the disease is still in a treatable condition, if the patient appears to have contracted colon cancer. Conversely, the absence of praja-1 will generally be indicative of a non-cancerous state in tested colon cells.

Still other genes coding for early developing liver proteins in accordance with the present invention have been identified and sequenced, and these proteins will also be useful in various methods of diagnosis and treatment of disease conditions associated with the liver or liver function. Included in these additional genes are those nucleic acids coding for a protein identified as pk, as depicted in FIGS. 4A-4B, nucleic acids coding for a protein identified as protein 106, as shown in FIG. 5, and genes 20, 36, 41, 112, 114, 118 and 129, as shown in FIGS. 6-12. These proteins also appear to useful in hepatocyte formation and in treating liver diseases in a similar manner to many of the proteins discussed above, and in a manner similar to known growth factors should be useful in treating a variety of conditions. For example, protein pk appears to be important in Ito cell formation and fibrosis and thus appears to be useful in the same manner as protein liyor-1 (145). Accordingly, the protein pk, as prepared from the nucleic acid sequence indicated at FIG. 4, will likely be useful in treating end-stage liver disease, hepatocellular carcinoma, as well as other disease conditions including anemia, ataxia, and hemochromatosis. As in the above cases, these early developing liver proteins may be administered with any other suitable compound normally used for administration to patients, such as suitable pharmaceutically acceptable carriers.

Another aspect of the present invention will comprise raising antibodies to the early developing proteins identified above, or to peptides or fusion proteins such as the pk protein (also known as itih-4) derived from these proteins. As would be recognized by one of ordinary skill in the art, antibodies to these proteins or to selected peptides or fusion proteins derived from these proteins may be prepared in any suitable conventional manner currently known, including raising antibodies in such animals as rabbits, sheep, goats, or guinea pigs. In the preferred embodiment, the following antibodies have been raised in rabbits:

(1) Peptides (13-mer) at aa 2-14 of mouse elf gene N-terminus having the sequence 5-ELQRTSSVSGPLS-3.

(2) Peptides (14-mer) at aa 2140-2154 of mouse elf gene C-terminus having the sequence 5-FNSRRTASDH-SWSG- (3) Peptides (13-mer) at aa 144-156 of mouse praja1 gene middle portion having the sequence 5-LR-RKYRSREQPQS-3.

In addition, the invention also comprises antibodies to the following peptides:

(1) 145peptide-A (18-mer) which was designed from the C-terminus of gene 145 (Cded) and has the sequence 5-SAQSLVVTLGRVEGGIRV-3 OR 5-CSAQSLVVTLGRVEGGIRV-3.

(2) 145peptide-B (17-mer) which was designed from the middle part of gene 145 (Cded) and has the sequence 5-KIEGSSKCAPLRPASRL-3 or 5-CAPLRPASRLPASQTLG-3.

(3) g59peptide-A (16-mer) which was designed from the N-terminus of gene G59 (Praja1) and has the sequence 5-PPREYRASGSRRGMAY-3 or 5-PPREYRASGSRRGMAYC-3; and (4) g59peptide-B (15-mer) which was designed from the middle part of gene 59 (Praja1) and which has the sequence 5-CKVPRRRRTMADPDFW-3.

The invention also comprises antibodies to a fusion protein such as a 40 kD pk/itih-4 fusion protein which covers the two EF-hands motifs of itih-4 (about 400-bp 14 kD).

The invention further comprises the use of the elf proteins of the present invention in interactions with TGF-β signaling molecules such as Smad2 and Smad3 so as to prevent or treat liver diseases such as primary biliary cirrhosis (PBC) and other diseases involving bile ducts. Evidence has shown that SMAD2 and SMAD3 insufficiency leads to a loss of bile ducts, and thus that TGFβ treatment of normal livers results in an increase in bile duct formation via the activation of SMAD2 and SMAD3. SMAD2/3 activity may be mediated by ELF, a Beta Spectrin. Loss of ELF function results in T lymphocytic proliferation and absent intrahepatic bile ducts. Livers deficient in SMAD2 and SMAD3 exhibit perturbations in ELF localization. This phenotype is seen in Primary Biliary Cirrhosis (PBC), a cholestatic disease with a progressive loss of intrahepatic bile ducts. Perturbations in ELF are correlated with a lack of SMAD2 and SMAD3 in this disease. Immunoprecipitation studies show that ELF binds SMAD2 and SMAD3, and that this binding is increased in PBC.

Previously, it was observed that compound haplo-insufficiency at the smad2 and smad3 loci resulted in a failure to form intrahepatic bile ducts, and that HGF could rescue this phenotype in a SMAD-independent pathway. It was noted that TGFβ could rescue the bile duct insufficiency in the mutant livers, although it did not completely rescue the hepatocytic defects seen. The effect of TGFβ on the wild-type explants was also quite interesting. Treatment of fetal livers with exogenous TGFβ in vitro resulted in a marked increase in the number of intrahepatic bile ducts. Moreover, the morphology of the bile ducts formed underwent a dramatic change. The bile ducts increased to twice their normal size, and were less regularly organized than those found in untreated liver explants.

In addition, it has also been previously shown that HGF was able to direct the formation of bile ducts while bypassing SMAD activation. The question of whether SMAD2 and SMAD3, the pathway specific SMAD proteins downstream of TGFβ and activins, were activated in the livers in the presence of TGFβ was also examined by looking at the subcellular localization of these SMAD proteins by immunofluorescence and confocal microscopy in explant livers from smad2+/−; smad3+/− mutants cultured in the presence of TGF Beta. It was determined that a narrow expression domain of SMAD2 is found just adjacent to the developing bile ducts, in which some SMAD2 appears to be nuclear, suggesting that it is activated and is transducing the TGFβ signal. SMAD3 was also expressed adjacent to the forming bile ducts, although its expression domain was much wider that seen for SMAD2. SMAD3 could also be found in the nuclei of some cells, suggesting it too was activated in response to the TGFβ. Therefore, diminution of SMAD activity through genetic haploinsufficiency ablates bile duct formation, while exogenous activation of SMAD2 and SMAD3 can augment bile duct development, suggesting a central role of TGFβ and SMAD2 and 3 in bile duct formation.

The phenotype of the smad2+/−; smad3+/− embryos was reminiscent of what was seen when ELF3 was inhibited by antisense oligonucleotides in liver explants (Mishra, Oncogene, 1999). Specifically, bile ducts failed to develop, and the hepatocytic architecture was highly deranged. ELF3 is a β-spectrin protein in accordance with the present invention, which we have shown is expressed in the membrane of hepatocytes. Indeed, recent confocal experiments have pinpointed a focused concentration of ELF3 protein at the apical, canalicular surface of the hepatocytes, which led to an examination of the effect of smad2/3 ablation on ELF localization. The evidence regarding the association of smad2 and 3 and the ELF proteins of the present invention is discussed in more detail in Example 3.

It is thus submitted that the foregoing embodiments are only illustrative of the claimed invention, and alternative embodiments well known or obvious to one skilled in the art not specifically set forth above also fall within the claimed scope.

In addition, the following examples are presented as illustrative of the claimed invention, and are not deemed to be limiting of the scope of the invention, as defined by the claims appended hereto, in any manner.

EXAMPLE 1

In accordance with the cloning strategy of the present invention to identify genes involved in early mouse liver development, we have isolated Praja-1, a gene with similar sequences to the *Drosophila melanogaster* gene goliath (gl), and which is involved in the fate of mesodermal cells ultimately forming gut musculatures, fat body, and the heart. Praja-1 is a 2.1 kb gene encoding a putative 423 amino acid ORF and includes a COOH-terminal RING-H2 domain. Using the Jackson Laboratory BSS panel, we have localized praja-1 on chromosome X at 36 cM, near the X inactivation center gene, Xist. Northern blot analysis demonstrated three transcripts (3.1, 2.6 and 2.1 kb) in mRNA from adult mouse tissues brain, liver, and kidney as well as in mRNA from developing mouse embryos (days 7, 11, and 17 post coitus, or p.c.). In vitro transcription/translation yielded two products with a Mr of 55.6 and 56.9 kD. The presence of the RING-H2 domain, a proline-rich region at the COOH-end, and regions rich in acidic amino acids, leads to the hypothesis that the Praja-1 product is involved in mediating protein-protein interactions, possibly as part of a protein sorting or transport pathway. This is strengthened by the similarity of praja-1 to rat Neurodap1, whose product has been shown to localize to the endoplasmic reticulum and golgi in brain.

The molecular mechanisms underlying hepatocyte differentiation are not well understood, and thus identifying the genes underlying the control of liver development will provide powerful tools for understanding liver function and development, and will allow the use of inducing liver differentiation for therapeutic purposes. As part of a strategy to clone such genes, we isolated a new RING-H2 finger gene, praja-1. RING-H2 fingers, a type of zinc finger, are similar to RING fingers except that Cys4 is replaced by His (see Freemont, *Ann. N.Y. Acad. Sci.* 684:174-192 (1993); Lovering et al., *P.N.A.S.* 90:2112-2116 (1993)). Here we show that praja-1 possesses a RING-H2 motif near the COOH terminal.

The RING-H2 motif is similar to that of the *Drosophila melanogaster* gl gene (Bouchard et al., *Gene* 125:205-209, 1993), and to the rat Neurodap1 gene (Nakayama et al., *J. Neurosci.* 15:5238-5248, 1995). Praja-1, which localizes to chromosome X, is expressed in mouse brain, liver, and kidney. The presence of the RING-H2 motif, plus the acidic, hydrophilic nature of the translation product, leads to the hypothesis that praja-1 plays a role in protein transport.

Materials and Methods cDNA preparation and 3'-RACE PCR: RNA was isolated from livers of day 11 p.c. embryonic mice (ICR, Harlan Sprague-Dawley) using guanidine thiocyanate (Chomczynski et al., *Ann. Biochem.* 162:156-159, 1987). Poly(A)+ mRNA was isolated from total RNA using Dynabeads, as per manufacturer's instructions. First strand cDNA was made from poly(A)+ mRNA using the Promega Reverse Transcriptase System and the 3'-RACE primer 5'-GACTCGAGTCGACATCGA-T17 (Frohman, In: M. A. Innis et al. (eds.), *PCR protocols: a guide to methods and applications*, Academic Press, San Diego, pp. 28-38., 1990). The 3'-RACE primer was also used as the reverse primer in the PCR reaction. The forward PCR primer, originally designed to amplify a conserved region of a clone 145/PH (pleckstrin homology) domain, was 5'-CTCAAGCAGGTCCTGGCACA. The PCR reaction mix contained cDNA from about 10 ng of poly(A)+ mRNA, 25 pmol of each primer, 1 mM dNTP mix, and 2.5 units of AmpliTaq DNA polymerase (Perkin-Elmer) all in 10 mM Tris, 1.5 mM $MgCl_2$, and 75 mM KCl, pH 9.2 in a final volume of 50 ml. The temperature program comprised 35 cycles of denaturation (94° C., 1 min), annealing (55° C., 1 min), and extension (72° C., 3 min), followed by an additional 8 minute extension. One of the resulting PCR products (CH7) comprised a 725 bp fragment, which was cloned into vector PCRII using the Invitrogen TA Cloning Kit for sequencing, and found by sequence analysis to possess a RING-H2 finger. The portion of the final cDNA clones which correspond to CH7 is indicated in FIG. 3.

Library screening: The PCR product CH7 was labeled with [a-32P]-dCTP (3000 Ci/mmol, Amersham) via primer extension using the reverse PCR primer plus AmpliTaq polymerase at 72° C. in PCR buffer (Konat et al., in *PCR Technology: Current Innovations* (H. G. Griffin and A. M. Griffin, Eds.), CRC Press, Boca Raton, pp. 37-42, 1994). The resulting antisense probe was used to screen plaque lifts of a whole embryonic mouse (day 11 p.c.) cDNA library in vector λZap (Stratagene). Positive plaques were picked and purified, and DNA was isolated from lysates using standard procedures (Silhavy et al., *Experiments with gene fusions*, Cold Spring Harbor Laboratory Press, Cold Spring Harbor, N.Y., 1984). Inserts were excised from λZap DNA using EcoRI, and were subcloned into pGEM3Zf(−) (Promega) for sequencing and subsequent manipulations.

DNA sequence analysis: DNA sequence comparisons to existing sequences were performed utilizing BLAST searches in Genbank. Alignments were performed using the GCG program PILEUP.

Chromosomal mapping: Southern blot analysis of genomic DNA from C57BL/6J (B6) and Mus spretus (SPRET/Ei) using [32P]-labeled CH7 as a probe revealed a restriction fragment length polymorphism for the enzyme TaqI. This polymorphism was used to follow the inheritance of the praja-1 gene using the (B6 X SPRET/Ei) X SPRET/Ei backcross panels (BSS) from The Jackson Laboratory Backcross DNA Panel Map Service (Rowe et al., *Mammalian Genome* 5:253-274, 1994). Linkage and order relative to other markers was determined by minimizing the number of multiple recombinants within each haplotype.

Northern blot analysis of Praja-1 expression: Northern blots containing 2 micrograms of poly(A)+ mRNA from mouse tissues (Clontech) were probed with [32P]labeled CH7 antisense strand using Express Hyb hybridization solution (Clontech) at 68° C., washed according to manufacturer's instructions, and subjected to autoradiography. A [32P]-labeled b-actin probe supplied with the Northern blots was used as a control to normalize RNA levels in each lane.

In Vitro Transcription/Translation:

A transcription/translation-coupled rabbit reticulocyte lysate system (Promega) was used, as per manufacturer's instructions for [35S]methionine labeling. Clones of praja-1 in pGEM3Zf(−) plus a luciferase control clone were used with T7-RNA polymerase (sense direction). Each reaction comprised 12.5 ml rabbit reticulocyte lysate, 1 ml reaction buffer, 0.5 ml 1 mM amino acid mix minus methionine, 0.5 ml T7-RNA polymerase, and 20 units RNasin, all in 25 ml final volume. After a 90 min incubation at 300° C., products were lysed in SDS/mercaptoethanol treatment buffer and separated on a 10% SDS-polyacrylamide gel according to Laemmli, *Nature* 227:680-685 (1970). Proteins were electroblotted onto a BAS-NC membrane (Schleicher & Schuell) using a BioRad Trans-Blot apparatus according to manufacturer's instructions. Labeled products were visualized by autoradiography.

Results:

Isolation and Sequence Analysis of the Novel Gene, Praja-1:

As part of the analysis of genes involved in liver development and function, we amplified the 3' end of a previously undescribed gene, CH7. We used the CH7 probe to screen a mouse embryonic cDNA library and isolated two overlapping clones, praja-1-5 and praja-1-6. Sequence analysis of the consensus overlap region revealed an open reading frame (ORF) of 424 amino acids, with a predicted size of 47.4 kD. Hydropathy analysis (Kyte et al. *J. Mol. Biol.* 157:105-132, 1982; not shown) shows that the translation product is highly hydrophilic, with no hydrophobic leader or membrane-spanning regions. The translation is also very acidic, with a pI of 4.6 and containing 17.7% acidic residues (Asp plus Glu). The putative ATG start codon indicated in FIG. 3 was selected because it is the upstream-most ATG that is in-frame with the ORF, and is preceded 21 bp upstream by a TAG stop codon. The context of this ATG, however, is only a weak fit to the consensus Kozak recognition sequence GCCACCatgG in that it does not have a purine at −3 nor a G at +4 (reviewed by Kozak, *Genome* 7:563-574, 1996). Sequence analysis of the amino acid translation revealed the presence of a COOH-terminal RING-H2 motif, which is a zinc finger variant (Freemont, supra). FIG. 13 shows an alignment of the RING-H2 motif of praja-1 with those of several other RING-H2 containing proteins.

Figure 14:
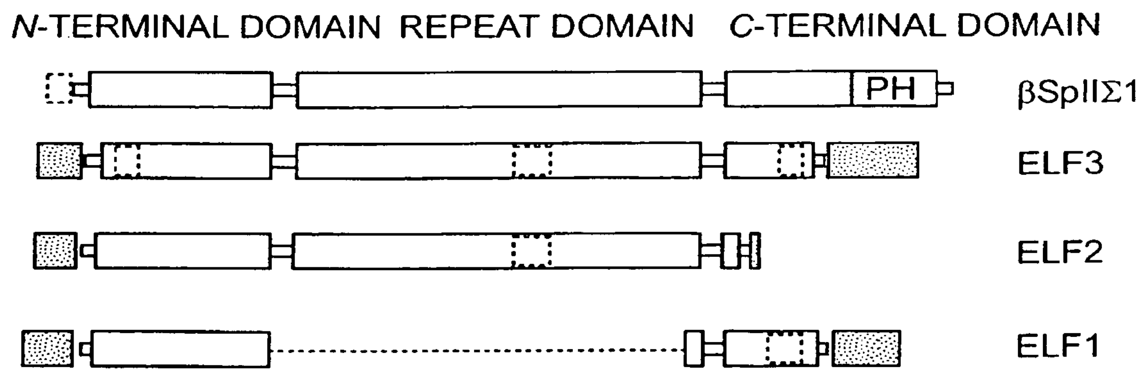
FIG. 14 is a graphic representation of known alternatively spliced patterns found among elf transcripts.

Linkage Analysis Places Praja-1 on Mouse Chromosome X:

A restriction fragment length polymorphism for praja-1 was identified using CH7 as a probe on a Southern blot containing DNA from the two parental strains digested with several restriction enzymes (TaqI, BglII, EcoRI, EcoRV, HindIII, HincII, KpnI, PstI). For every enzyme used, C57B16/J had only a single restriction fragment, while two fragments were always observed within the SPRET/Ei lane. A polymorphism obtained using TaqI was used to type the inheritance of the C57B1/6J allele in the BSS panel. There are two Spretus bands S1 and S2 and one C57B1/6J band B1. After comparison of the praja-1 genotypes to other genes typed within the database, it was determined that praja-1 maps to mouse chromosome X at about the 36 cM position (FIG. 14). The Si band is the praja-1 allele on X chromosome of SPRET/Ei. The S2 TaqI fragment appears in every backcross animal. Since all males from the backcross contain this allele, it is not localized to the X chromosome. Since females also have the S2 band, it is not Y-linked. Therefore S2 is an autosomal locus that contains sequence homology to the praja-1 probe sequence. Other genes mapping to this general region include moesin (Msn), androgen receptor (Ar), interleukin-2 receptor gamma (Il2rg), X-linked zinc finger protein (Zfx), and tabby (Ta). This area is also 1.1+/−1.1 cM from the Xist locus. Further studies are needed to determine if praja-1 is not expressed on inactivated X-chromosomes and if it plays a role in X-inactivation. The syntony and conserved gene order between mouse and human X chromosomes (Herman et al., *Genome* 6:S317-S330, 1996) allows comparison with human disease genes in the region. Human diseases in this region with mesodermal involvement include anhidrotic ectoderm dysplasia (eda) and sideroblastic anemia with spinocerebellar ataxia (asat).

In vitro expression produces a protein product larger than the predicted size. An autoradiogram of the in vitro transcription/translation products of clones praja-1-5 and praja-1-6 showed that only praja-1-5 produced a significant product. The product, which ran as two closely spaced bands of Mr=55.6 and 56.9 kD, is larger than the predicted ORF size of 47.4 kD. One possible explanation is that the expression product is very acidic, and acidic proteins such as granins are known to give anomalously high Mr on SDS-PAGE (Huttner et al., *Trends Biol. Sci.* 16:27-30, 1991). The presence of two products suggests translation initiation at a second, internal ATG codon, such as at Met-19 (FIG. 3).

Praja-1 transcripts are present in embryonic and in mouse tissues. Northern blot analysis of RNA from adult mouse showed expression of 3.1, 2.6, and 2.1 kb transcripts in liver, brain, and kidney, and an additional 2.3 kb transcript in testis. The praja-1 protein is unlikely to be a membrane receptor, since it lacks a hydrophobic transmembrane domain. The uniform hydrophilicity suggests a soluble protein. The praja-1 RING-H2 motif is shown aligned with those from several other proteins in FIG. 13. RING fingers are generally thought to function in protein-protein interactions (Borden et al., *Curr. Opinion Struct. Biol.* 6:395-401, 1996; Saurin et al., *Trends Biochem. Sci.* 96:208-214, 1996). To cite a specific example, if either of the two cysteines that comprise the Zn++ binding site of the RING finger of acute promyelocytic leukemia protooncoprotein PML are mutagenized, then the nuclear multiprotein complex, or so-called nuclear bodies, fail to occur (Borden et al., *EMBO J.* 14:1532-1541, 1995). The authors conclude that the PNM RING domain, and probably other RING finger domains, are involved in protein-protein interactions.

In praja-1, aside from the RING-H2 finger, the stretch of thirty-four COOH-terminal amino acids just past this motif (FIG. 3) is especially rich in proline residues (17.6%); and, as stated, the protein in general is very acidic. Proline-rich domains are found in several mammalian transcription factors, such as that at the COOH-terminus of transcription factor CTF, and proline-rich regions and also acidic regions are likely to function in contacting other proteins (Mitchell et al., *Science* 245:371-378, 1989). A BLAST search of the proline-rich COOH-terminus revealed no significant matches to any protein in the available databases, however, when considering the praja-1 sequence as a whole, the rat Neurodap1 gene has the highest similarity; the alignment is presented in FIG. 15.

Figures 15A, 15B, 15C, 15D:
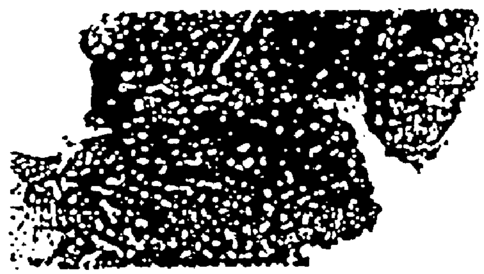
FIG. 15 represents ELF expression in primary biliary cirrhosis.

Neurodap1 is expressed abundantly in rat brain, with much smaller amounts in heart and skeletal muscle. Though praja-1 likewise shows greatest expression in brain, unlike Neurodap1 it also expresses in liver and kidney. The subcellular localization of Neurodap1 was shown to be concentrated around the endoplasmic reticulum (ER) and golgi of the cerebral cortex and facial nucleus, and especially in the postsynaptic density region of axosomatic synapses (Nakayama et al., supra). Based on its subcellular localization, plus the presence of the RING-H2 finger, the authors concluded that Neurodap1 is probably linked to the secretory or protein sorting. Praja-1 does differ from Neurodap1 in several respects, however. In addition to being expressed in some different tissues than Neurodap1, praja-1 encodes for a product that is smaller (47.4 kD, based on the composite of the clones in FIG. 3) vs. 77.9 kD for Neurodap1. The difference in size is at the N-terminus of the proteins (FIG. 15). The largest transcript we observed for praja-1 was 3.1 kb, whereas Neurodap1 exists as a single 4.8 kb transcript on Northern blots of rat brain mRNA.

In light of the fact that BRCA1, which possesses a RING finger, has an acidic pI, and is a secretory protein, also has properties of the granin family of proteins (Jensen et al., *Nature Genet.* 12:303-308, 1996), we examined praja-1 for a granin signature. We found no region in the praja-1 translation that gave a perfect match to the consensus E[N/S]LX[A/D]X[D/E]XEL, though two regions matched five of the seven conserved residues. We were also unable to demonstrate the presence of clear coiled-coils, which are present in BRCA1 and proteins with the previously-mentioned tripartite structures. In these respects, praja-1 is more similar to Neurodap1 than to proteins such as BRCA1. Also, though the RING-H2 finger in praja-1 shows much similarity to that from the *D. melanogaster* goliath (gl) protein (FIG. 13), the goliath protein possesses an alkaline pI (8.9) and no sequence similarity to praja-1 outside of the RING-H2 finger. The RING-H2 motif plus acidic and proline-rich regions, and similarity to Neurodap1, leads to the conclusion that praja-1 is involved in protein-protein interactions, possibly in a protein sorting or secretory pathway.

EXAMPLE 2

In accordance with the present invention, investigations were made with regard to the induction of differentiation in liver tissues in order to isolate and identify early developing liver proteins for use in therapies involving the liver and liver functions. In the developing fetus, inductive interactions, intercellular communication and the establishment of cell polarity are critical for growth and patterning during development. However, the precise mechanisms by which these effect hepatocyte differentiation or liver development have not previously been elucidated. Mammalian liver development was first recognized to be established through a specific sequence of interactions between mesenchymal and endodermal embryonic tissues. At 9.5 days of mouse gestation, upon signaling from the cardiac mesenchyme, endodermal cells from the liver diverticulum proliferate and migrate into the surrounding septum transversum. This specific area of loose mesenchyme in turn differentiates into hepatic mesenchyme and a liver bud is finally recognizable microscopically at about 10.5 days of gestation. This hepatic mesenchyme is continually responsible for the hepatocyte proliferation which then proceeds throughout embryonic life (Le Douarin,

*Med. Biol.* 53:427-455, 1975). Albumin transcription can be detected as early as at day 9.5 (Cascio et al., *Development* 113:217-225, 1991), implying that hepatocyte differentiation begins when hepatic endoderm comes into contact with cardiac mesoderm. As a first step towards the analyses of signal transduction pathways regulating such a restricted pattern of gene expression, molecular markers as well as regulatory genes are required to identify the interactions required for liver development.

The dissection of gene regulatory pathways in the liver has led to the identification and characterization of transcriptional activators, C/EBP, DBP, LFB 1/HNF 1, 3 and 4 (Johnson, *Cell Growth Differ.* 1:47-52, 1990; Kuo et al., *Development* 109: 473-481, 1990; Frain et al., *Cell* 59:145-157, 1989), of liver specific genes, such as α-fetoprotein and albumin (Tilghman, *Oxford Surveys on Eukaryotic Genes*, Oxford University Press, 1985). Yet, with the exception of HNF4, 3 α and β (Ang et al. *Development* 119:1301-1315 (1991) and *Cell* 78:561-574, 1994), none of the above have been found to play a definitive role in determining cell-lineage and regional specification of the developing liver. The small volume of liver buds (approximately $4\times10^{-2}$ mm$^3$) yields even smaller quantities of proteins, DNA and messenger RNA thus making the molecular analysis of liver development difficult. Therefore, the construction of early embryonic liver cDNA libraries, and performing subtractive hybridization still remains the most plausible and comprehensive method of obtaining an unbiased catalogue of genes required during early mouse liver development (see Harrison et al, *Development* 121:2479-2489, 1995).

The isolation of markers would provide further insight into identifying transcriptional activators and growth factors involved in such a restricted pattern of gene expression, and eventually provide an approach to identifying signal transduction pathways involved in hepatocyte differentiation. In some cases, these pathways have been characters as in patterning and axis formation of the vertebrate head and body (Oliver et al., *Development* 121:693-705, 1995; Kessel et al., *Science* 249:374-379, 1990). For example, in *Xenopus*, a network involving brachyury, activin and wnt-related genes, is responsible for mesoderm induction, somitogenesis, myogenic and sclerotomal differentiation (see, e.g., Wilkinson et al., *Nature* 343:657-659 (1990); Herrmann et al., *Development* 113:913-917 (1991); Green et al., *Trends Genet.* 7:245-250 (1991); Sokol et al., *Cell* 67:741-752 (1991); Smith et al., *Cell* 67:753-767 (1991), and dorsal ventral axis formation results from Xgsk-3 (the *Xenopus* homologue of *Drosophila* zw3/shaggy) phosphorylating its *Xenopus* homologue of armadillo, β catenin thus regulating the level of β catenin available for dorsal axis formation. However, there are no available molecular markers nor pathways which chamctedw either earlier liver development, nor its crucial mesodermal component.

In accordance with the present invention, it has been possible to identify and characterize such molecular markers and possible inductive transcripts for liver development. As set forth below, the characterization of the elf protein is described, and the expression of this protein may mark the separate components of liver development. The "bottom up" approach with regard to this characterization in general has led to the identification of a totally unexpected group of genes, and in particular, this is described with regard to the elf protein, which is probably involved in playing a role in establishing cell polarity by interactions at the surface membrane.

Characterization of cDNA Libraries:

The four stages in liver development (e10, e11, e12, and e14, where e=embryonic) are defined developmental time points from undifferentiated mesodermal/endodermal cells to a well developed and differentiated fetal liver. A change in cell polarity occurs at e9-10. At e10.5-11, invasion and migration of endodermal cells into surrounding mesenchyme occurs; at e11.5-12, pseudolobule formation, cords of hepatocytes form together with early sinusoids. cDNA libraries representing these stages would therefore, represent "captured" mRNA species expressed in greater abundance during crucial time periods for hepatocyte formation, enabling their isolation and providing a method for analyzing the changing pattern of gene expression during liver development.

Libraries containing $5.0\times10^6$–$4.1\times10^7$ independent clones were generated from the largest cDNA fractions. Current estimates demonstrate that a library containing $5.0\times10^5$ clones (Sambrook et al, *Molecular cloning, a laboratory manual*, Cold Spring Harbor Laboratory Press, Cold Spring Harbor, 1989) is a representative library with a 99% probability that rare transcripts (less than ten copies per cell) are present. Our libraries are therefore likely to be truly representative of their respective mRNA species for that stage.

Qualitative and Developmental Profiles of the Libraries:

These were obtained, utilizing genes, such as IGF-II, IGFBP-2, IGF1, C/EBP, HNF/LFBI known to be expressed at different time points in developing liver. The data in Table 2 below demonstrate that IGF-I was not detected in any of the embryonic libraries, while IGF-H was detected in the e10.0 and e12.5 libraries (3 at e10.0 and 4 at e 12.5). IGF-II was not detected in the adult liver library. Interestingly, BP-2 clone frequencies are similar to IGF-II in the early e6.5, e7.5 and e8.5 libraries (data not shown), but in the liver cDNA libraries the clone frequencies differed, for BP-2 only one clone per 100,000 being detected at e10.0 and e11.5, while 7 were detected in the adult liver cDNA library compared to the greater numbers for IGF-II. This implied that its temporal and spatial expression in the embryo and fetus is different from IGF-II and this was subsequently confirmed by in situ studies. HNF1/LFB I detected in the e12.5 library was suddenly detected at day 11.5 and 12.5 in low abundance (2 clones/100,000 at e11.5 and 5 at e12.5), confirming that while it is expressed, its level also may be regulated, albeit downward, in embryonic stages. Lastly, mouse β-Actin was used as a reference: all seven libraries had similar β-Actin frequencies from 120-300/100,000 clones which is considered representative of such embryonic libraries.

Identification of Stage Specific Clones by Subtractive Methods:

Two subtracted libraries were then constructed as previously described, comprising 64 clones (e11.5-12.5), and 174 clones (e10.5-11.5). Further characterization of these clones was carried out by Southern hybridization, sequencing, Northern blot analysis, Zoo blot analysis, and in vitro fertilization of protein. Using Southern blotting, thirty-four clones were shown to be stage specific and not containing mitochondrial, ribosomal and globin sequences, and further analysis was carried out on elf.

Identification and Developmental Regulation of Elf Transcripts:

Elf mRNA in tissues from mid-gestational embryos were analyzed, and tissues were dissected from day 11 onwards since it was at this stage that discrete hepatic, cardiac and other tissues could be dissected with ease, and the subsequent RNA isolated was of good quality. Using a 32P-labeled 1.1

Kb insert representing elf, the specificity of the developmental changes in the steady state levels of elf was evaluated by also measuring the relative levels of β-Actin. This revealed a 2.1 Kb transcript at high stringency washes. Scanning densitometry of the respective bands revealed that maximal expression of elf occurred in liver and heart, less so in other tissues but specifically on day 11, and in 12.5, 14.5 in decreasing abundance (when Northerns were developed 1-2 months later).

Sequence Analysis of Elf:

After subtraction hybridization, one stage specific clone was analyzed in detail: sc32. The initial libraries were then screened at high stringency (0.2×SSC, 60°), to obtain overlapping clones for sc32. Positives were picked, and after in vivo excision (Stratagene) into Bluescript, these were sequenced using the dideoxy chain termination method using oligonucleotides corresponding to previously determined sequence. Of the seven clones picked, three were found to be overlapping to sc32 and included sequence encoding elf (FIGS. 16*a* and 16*b*). Confirmation of the identity of the clones and elf was carried out by Northern blot analysis of mouse embryonic tissues. In the case of elf, this gave rise to the same initial 2.1 Kb transcript with sc32 as a probe. A start codon was not present suggesting that we had not cloned the 5' end of the cDNA. However, the northern blot showed a 2.1 Kb transcript, thus suggesting that we had cloned complete elf and this probably represented a spliced form of β-fodrin. The authenticity of the 3' end of the elf sequence was confirmed by the comparison of the elf sequence with the expressed sequence tags (EST) database. Although no mouse ESTs for elf sequence were found, three different human EST clones were found to span the region of unique last 100 nt and the 5' adjacent sequence, suggesting the existence of elf homolog in human cells (see FIGS. 16*a* and 16*b*).

Prior sequence analysis has shown elf to bear 80% identity to β-fodrin, a non erythroid β-spectrin. Our sequence to elf is located between domains II and III of the β-spectrins. Domain II comprises 17 repeats of a 106 amino-acid motif and an ankyrin binding domain (FIG. 16*a*). The ankyrin binding domain is required for the correct subcellular localization of adducin, ankyrin and the Na+, K+ ATPase, without which cell morphology is disrupted. Domain II comprises a C terminal domain which contains varying numbers of residues (52-265) in alternatively spliced forms giving rise to tissue specific expression (Hu et al., *J. Biol. Chem.* 267:18715-18722, 1992), as well as the PH domain.

In Situ Localization of Elf:

In situ hybridization confirmed elf expression in 11.5 heart and liver and determined its expression pattern during earlier liver development, using elf sense probes and alpha fetoprotein antisense probes as controls. The hepatic diverticulum, which originates at the foregut-midgut junction, begins to grow into the septum transversum at the 9th day of gestation (13-20 somite stage). Between days 10.5 to 11.0 p.c., a considerable degree of differentiation is seen in this primitive liver. The liver enlarges substantially over this period: the increase in the overall volume being due to the invasion of the mesenchyme of the septum transversum by the hepatic cords, and the initiation of hematopoietic activity in this organ. At day 9.5, a strong labeling of elf becomes apparent in the cardiac silhouette: the pattern appears to be trabecular, including the wall of the cardiac anlage. A section of the cephalad chamber (sino-atrial chamber) wall also bears a high intensity of elf expression. The surrounding tissue, particularly the caudal liver bud region does not show the presence of silver grains. At the next stage, day 10.5, silver grains clearly highlight the developing liver, which appears as a horizontal oriented structure (L) in this section. At this stage, the signaling is weakening in the developing heart tissue. The surrounding tissues are remarkable for the absence of silver grains. At day 11.5, a strong labeling becomes apparent in the liver, which is larger in size. The heart shows an extremely weak signal: silver grains being visible in only a single streak posteriorly. At this stage, elf expression also appears in the umbilical cord. As a control, in addition to sense probes, a riboprobe to α-fetoprotein outlines the developing embryonic liver at day 11-12.

A comparison of the day 9.5 and 10.5 embryos demonstrates a clear temporal and spatial gradient of maximal tissue staining with silver grains representing elf riboprobe: the temporal gradient of a rise and fall of elf expression in the heart may be inferred from the strong staining in the developing heart at day 9.5 followed by a weaker staining at the next stage (day 10.5). Simultaneously, liver expression increases. The spatial gradient is apparent from the developed patterns of these tissues which showed that silver grains increase in density as one moves from the developing heart to the liver: at day 10.5, antisense RNA probes from elf cDNA hybridized specifically to 9.5 day cardiac mesenchymal tissue; expression at day 10.5 being restricted to cardiac and hepatic tissue; elf expression finally being restricted to the liver in later 11.5 day embryos. Of note, elf expression was seen in embryonic livers at later stages (days 12.5, 14.5 p.c.), but only in decreasing abundance: message being detected in these later stages when Northerns and in-situs were developed a considerable time later. Elf sense probes did not hybridize to any tissues.

Alpha fetoprotein antisense RNA probes hybridized specifically to 11.5, 12.5, 14.5 embryonic mouse liver tissue, in agreement with previous studies of mRNA isolated from embryonic liver samples (Tilghman et al., *P.N.A.S.* 79-5254-5257, 1982). The earliest stage of detection of α-fetoprotein mRNA by in situ hybridization was at 10.5-11.0 days of gestation. Similar experiments with albumin mRNA (Cascio et al., *Development* 113:217-225, 1991) have shown it to be expressed at 9.5d in clusters of cers arising from foregut epithelium and in cords of cells beginning to invade the septum transversum. In the experiments with α-fetoprotein, the liver was labeled at all subsequent stages (day 11 onwards), and, upon histological examination appeared to occur primarily in the endothelial cells. Hematopoietic cells appeared refractile but did not contain the hybridization grains that were visible over the α-fetoprotein positive cells.

ELF mRNA Distribution in Mesodermal Tissues Versus Alpha Fetoprotein mRNA in Endodermal Tissue:

Since Northern analysis revealed elf expression to occur in day 11.5 heart and liver tissue, we investigated whether elf expression was restricted specifically to mesodermal tissue from the heart and the liver and compared this to the endothelial expression of α-fetoprotein. Three main regions of mesoderm can be discriminated in the developing embryo: dorsal (somitic), intermediate, and lateral. Lateral plate mesoderm comprises somatic (pleura, pericardium, peritoneum and limb bud), and splanchnic (heart-epicardium, myocardium, connective tissue and smooth muscles of viscera and blood vessels, hemangioblastic tissue, adrenal cortex and spleen). Regarding the developing heart, at day 9 (13-20 somites), this is seen to beat regularly and strongly. At this stage, the heart appears to be the only region within the embryo where the endothelial elements of the circulation are surrounded by a vessel wall. The walls of the common ventricular chamber as well as the common atrial chamber show an increasing degree of trabeculation. Of note, the space between the endothelial and myocardial elements is filled with loose mesenchyme called cardiac jelly. In situ hybridization of days 9 and 10 embryonic heart tissue using elf antisense riboprobes demonstrated high levels of labeling to both the atrial and ventricular regions.

Hepatic mesenchyme also originates from lateral plate mesoderm. The septum transversum part of the hepatic mesenchyme originates from the splanchnic mesoderm of the precardiac area and this is thought to be responsible for the subsequent differentiation of hepatocytes. However, tissue explant experiments have shown that all derivatives of the lateral plate can replace hepatic mesenchyme for these later events. While these initial experiments have demonstrated migrating endoderm must interact with mesenchyme for the former to differentiate into hepatocytes (Le Douarin, 1975; Houssaint, *Cell Differ.* 9:269-279, 1980), more recent studies investigating albumin mRNA expression as an indicator of hepatocyte differentiation, have confirmed these features: initial expression of albumin mRNA occurs during the invasion of the septum transversum, when the hepatic precursor cells clearly contact cardiac mesenchymal tissue. Similarly, primer extension analysis of albumin transcription has revealed the start site of transcription to occur at day 10.5 with a 15-20 fold increase in albumin mRNA upon liver organ formation by day 12.5. In our experiments using α-fetoprotein as a marker for differentiated hepatocytes, it was clear under high magnification, that while α-fetoprotein expression is restricted to the later endodermal component of liver development, elf expression seems to occur in the loosely organized, lighter staining mesenchymal cells—initially cardiac mesenchyme (at day 9.5), then in both cardiac and hepatic tissue (at day 10.5) and then restricted to liver tissue (day 11.5 onwards; elf expression then decreasing upon liver formation. Examination of the later histological sections (days 11 onwards) showed a diffuse distribution of grains. The resolution that was attained did not allow one to draw a firm conclusion about the identity of the hybridizing cells, although it seemed that the hybridization signal with elf was localized in the perisunusoidal cells, but not in the hepatocytes.

Distribution of Elf RNA in Adult Tissues, Conservation in Evolution:

Further characterization of elf has involved RNA analysis of adult mouse tissues. Elf hybridizes to adult liver, kidney and testis as a 2.1 Kb transcript in liver and kidney and a 2.6 Kb transcript in adult testis, in very low abundance. Genomic analysis of elf DNA from human, monkey, rat, mouse, dog, cow, rabbit, chicken and yeast indicates that elf is conserved across the species, being represented in all except rabbit DNA (FIG. 18).

In vitro transcription and translation of elf, the latter using nuclease-treated rabbit reticulocyte lysate (promega), has revealed a 34 Kd protein, which is as predicted by the elf insert size and indicating that this insert is in frame for the coding sequence for a specific protein (FIG. 17).

Embryonic Liver Explants Cultures:

One of the goals of the investigations in conjunction with the present invention was to establish a functional assay for determining the developmental roles of elf and ss3 in liver formation. Mouse embryonic liver explants were cultured in our laboratory, in order to overcome the dissection and analysis of extremely small tissue sections at day 10-10.5 when the liver bud is 0.2 mm. When cultured in the complete absence of mesodermal derivatives, hepatic endoderm deteriorates rapidly. Only 2 out of 15 such liver explants survived. Hematoxylin and eosin staining showed a necrotic endoderm with no apparent signs of hepatic differentiation. When associated with the surrounding mesoderm particularly cardiac mesoderm (en bloc dissections), the endodermal cells had proliferated and invaded the mesoderm strands. Hepatocytes were seen to be organized in cords separated by sinusoids with pseudo-lobule formation. All 15 out of 15 cultures from en bloc dissections were completely viable. These studies confirm prior explant studies demonstrating the necessity of surrounding mesoderm for liver formation. Semi-quantitative RT-PCR analyses of elf, other clones ss3, 145, HNF 3β with GAPDH and α-fetoprotein as controls demonstrate increased expression during mesodermal-endodermal interactions.

Early experiments in chick embryos (Douarin, 1975, supra) have demonstrated that at the primitive streak stage, the prospective hepatic area is localized in the middle and in the lateral areas anterior to Hensen's node. At the head process stage, prospective liver areas coincide with cardiac areas, being concentrated in bilateral areas extending from the tip of the head process to an area slightly behind the primitive pit.

Potential liver areas were tested by transplantation of pieces of tissue on the chorioallantoic membrane; liver differentiation in such explants was dependent upon the presence of cardiac tissue: no liver tissue was found without cardiac cells in the vicinity, whereas some grafts contained heart tissue without liver. After gastrulation is completed, it is during the somitic stage that the liver and heart segregate partially—the presumptive cardiac mesenchyme migrates anteriorly and venally into the cardiac fold, the prospective myocardial cells becoming incorporated in the heart anlage. Another series of experiments using carbon particle labeling, radiodestruction and coelomic transplantation of pieces of blastoderm showed liver endodermal and mesodermal areas which am superimposed during the early embryonic stages evolve differently later on.

Tissue explant studies have revealed that in normal liver development, hepatocyte differentiation and the formation of liver lobes is entirely dependent upon the mesodermal component which then becomes progressively colonized by the growing endoderm hepatic cords (see Douarin, 1975, supra). These stimulating properties of the cardiac, and then, hepatic mesenchyme have been demonstrated to begin at the 5 somite stage and last throughout embryonic life. The findings set forth herein show that elf is expressed in early cardiac mesoderm, with subsequent expression being limited to hepatic mesoderm, revealing this to be a novel marker for the mesodermal component of liver development. Of note, in normal development, pure liver mesenchyme is never observed. That these explant studies have demonstrated expression of elf, indicates that elf protein will be useful in identifying and studying interactions between mesoderm and foregut endoderm.

Summary of Events During Hepatocyte Formation Indicating a Role for Elf:

Sequence analysis has shown elf to bear 80% identity to β-fodrin, a non erythroid β-spectrin. β-spectrins have been implicated in numerous functions including the maintenance of cell surface polarity of cells (Nelson et al., *J. Cell. Biol.* 108:893-902, 1989); the maintenance of cell-cell junctions (Thomas et al., *Development* 120:2039-2050, 1994, Luna et al., *Science* 258:955-964, 1992); β-spectrins contain binding sites for other proteins, such as ankyrin and actin (Hu et al., *J. Biol. Chem.* 267:18715-18722, 1992; Speicher et al., *Nature* 311:177-180, 1984). Smaller isoforms β-spectrins have been well described. For instance, a 4.0 Kb muscle tissue transcript is thought to encode a previously reported β-spectrin from clustered acetylcholine receptors. Similarly for elf, the missing domains may be replaced through alternate exon usage to generate proteins with unique functions. A function for elf thus appears to be in the assembly and maintenance of specific domains on the cell surface—towards establishing hepatocyte polarity and thus differentiation.

Spectrins have also been shown to be conserved throughout evolution and am developmentally regulated. These results demonstrate that in keeping with brain β-spectrin (β-G spectrin), elf is also expressed in a tissue and stage specific manner and is conserved throughout evolution (Hu et al., *J. Biol. Chem.* 267:18715-18722, 1992; Zimmer et al., *Brain Res.* 594-75-88, 1992; Leto et al, *Mol. Cell Biol.* 8:1-9, 1988). Elf expression occurs in a gradient-like manner and close examination of Brain β-G spectrin has demonstrated similar gradient patterns, suggesting that a sudden on-off phenomenon at specific time points is simplistic. That elf is maximally expressed at day 10-11 suggests that it has an important function at this time, which continues, although to a lesser extent, with the later stages. For instance, it is conceivable that elf by conferring cell polarity mark the first overt sign of hepatocyte differentiation. Therefore, like Drosophila β-H spectrin, elf may play a role in facilitating a "velcro-like" joining of neighboring cell membranes as they extend (Thomas et al., *Development* 120:2039-2050, 1994). In this way elf may mark the polarization of the surrounding mesodermal cells, enabling foregut endodermal cells to invade this area and differentiate into hepatocytes. Molecular markers have been invaluable in the dissection of inductive events in embryological studies (New et al., *Curr. Opin. Genet. Dev.* 1:196-203, 1991; Sive, *Genes Dev.* 7:1-12, 1993). For instance, in *Xenopus*, Epi 1, an antibody specific for epidermis, has been used to elucidate the role of the blastopore lip in the neural induction process (Savage et al., *Dev. Biol.* 133: 157-168, 1989). Similarly activins (regulating keratin) (Asashima et al., *P.N.A.S.* 88:6511-6514, 1991), vg-1 (Thomsen et al., *Cell* 63:485-493, 1990) and other genes belonging to the TGF-β family, as well as wnt and bFGF families represent components of the cascade leading to the commitment to particular mesodermal fate. For instance, vg-1, originally isolated by differential screening is to cells inducing embryonic mesoderm, the posttranslational processing of Vg-I precursor protein on the future side of the embryo being a key step in generating dorsal mesoderm and body axis in *Xenopus* (Thomsen et al., *Cell* 74:433-441, 1993). Similarly, in isolating putative inductive agents required for liver formation, a key step is the identification of mRNAs localized to cardiac/liver mesenchyme: elf and its regulatory genes will help to elucidate this area.

More recently, cell-cell interactions have been shown to be important for several cell fate decisions. In *C. elegans* for instance, lin-12 and glp-1 have been shown to encode transmembrane proteins mediating intracellular communication, and are required for the specification of several anterior fates. In *Drosophila*, the establishment of secondary epithelia which are the result of a mesenchymal-epithelial transition, is thought to be dependent upon two separate adhesions systems: direct interactions between the developing midgut endoderm and the visceral mesoderm on one hand and, adhesive interactions between the epithelial cells themselves on the other. While the latter cell-cell interaction is thought to be controlled by shotgun, control of apicobasal polarity is thought to be caused by genes such as cnanbs and stardust (Tepass et al, *Cell* 61:787-799, 1990). Although it is known that the biogenesis of cell surface polarity in hepatocyte formation is an early event, implying that the mechanisms for sorting plasma membrane molecules are functional at an early point, genes involved in cell signaling leading to cell fate in liver development have not been defined to date. The identification of such genes would give tremendous insight into the cell-cell interactions involved in foregut endodermal cell migration and subsequent morphogenesis of the liver as an organ. These studies establish the principle that specific mesoderm mRNAs are localized in a way that guarantees their subsequent segregation to specific mesodermal tissue, in this case the presumed mesodermal component of the liver as demonstrated by embryonic explant studies (Le Douarin, 1975).

Cloning and Sequencing of Elf:

All embryonic liver was obtained from matings of randombred ICR mice (Harlan). The plug date was designated as Day 0 and embryos collected at days 10.0, 11.5 and 12.5 p.c.; these were staged by morphological criteria (Theiler, *The House Mouse*, New York: Springer-Verlag, 1989). The livers were dissected, pooled and lysed. To prepare cDNA libraries, RNA was isolated (Chomczynski et al., *Analyt. Biochem.* 162:156-159, 1987) and poly(A)+RNA selected using oligo(dT)-cellulose (Collaborative Research Type 3). 1 to 5 mg of poly(A)+ RNA were used in the preparation of oligo(dT)-primed cDNA libraries. cDNA library construction of days 11.5 and 12.5 embryonic liver was carried out by conventional techniques (Gubler et al., *Gene* 25:263-269, 1983), and the day 10.0 and adult mouse liver using the Stratagene Unizap cDNA library kit. Two subtracted libraries were then constructed (Schweinfest et al., *Genet. Anal. Tech. Appl.* 7:64-70, 1990). The resulting subtracted libraries comprised 64 clones (11.5-12.5), and 110 clones (10.5-11.5). The process involved: (a) Biotinylation: fifty micrograms of cDNA from day 12.5 liver library at 10 mg/ml were biotinylated in HE buffer (10 mM Hepes, pH 7.5, 1 mM EDTA, Clontech Labs.); (b) Subtraction was then done by the streptavidin-phenol extraction: the streptavidin-biotin hybrid duplexes represent common gene products which selectively partition into the phenol interface, leaving the unique, subtracted single stranded cDNA in the aqueous phase. After synthesis of second strand DNA and overnight precipitation, one tenth of the DNA was used to transform competent XL Blue cells. Transformation using all the subtracted DNA led to the identification of 174 recombinant colonies. Purification of bacteriophages, preparation of DNA were carried out by the stratagene in vivo excision protocol. Plasmid DNA was sequenced using 77 DNA polymerase (Sanger et al., *J. Mol. Biol.* 143:161-178, 1980).

Sequence Analysis:

The NCBI non-redundant (nr) and EST databases were searched using the blastp2 and blastn2 programs, which permit gapped alignments (Altschul et al., *Methods in Enzymology* 256:460-480, 1996), with the default parameters and elf protein or nucleotide sequences as queries.

RNA Preparation and Analysis:

Embryos were collected at day 10.0, 11.5 and 12.5 p.c. Embryonic livers were dissected in Dulbecco's modified Eagle's medium (high glucose) and 20 mM Hepes pH 7.3. The livers for the specific stages were pooled and total RNA isolated (Chomczynski et al., supra). 10 micrograms of RNA were electrophoresed on a 1% formaldehyde gel and transferred onto Hi-bond nylon membrane (Amersham) using standard procedures (Sambrook et al., 1989, supra). Radioactive, $^{32}$P-labeled probes were synthesized by random primer methods (Feinberg et al., *Analyt. Biochem.* 137:266-267, 1984) and hybridized to the Nylon filters. Filters were washed at high stringency with a final wash in 0.2×SSC (30 mM NaCl, 3 mM sodium citrate, pH 7.4) 0.5% Sodium Dodecyl Sulfate at 65° C. for 60 minutes. Filters for each probe were stripped and rehybridized with other probes to confirm that no cross hybridization signals were obtained under initial screening conditions. These filters were then autoradiographed with intensifying screens at −70° C.

In Situ Analysis:

In situ analysis was performed for elf (Cox et al., *Dev. Bio.* 100:197-206, 1989). The RNA probes were synthesized and labeled with $^{35}$S-UTP (400 Ci/mmole) via the T7 or SP6 promoter for RNA polymerase. Sense or antisense probes were added to the appropriate sections, mounted, sealed with rubber cement and incubated at 50° C. overnight. After incubation, sections were washed with 50% formamide/5×SSC/10 mM DTT (50° C.; 2×30 min.) followed by 4×SSC/TE, incubated with RNase A (20 mg/ml) and RNase TI (500 U/ml; 37° C. 30 min), rinsed again with 4×SSC/TE (37° C., 30 min), twice 2×SSC (25° C., 15 min), twice in 0.1×SSC (25° C., 15 min), dehydrated with an ethanol series (containing 0.3 M ammonium acetate) and air dried. For autoradiography, slides were dipped in NTB 2 emulsion diluted 1:1 with 2% glycerol in water and dried. Exposure times were from @ weeks to four months. The emulsion was developed according to manufacturer's directions.

In Vitro Translation of Elf:

Bluescript containing elf was transcribed with T7 RNA polymerase using the in Vitro Eukaryotic Translation kit and MCAP mRNA Capping kit (Stratagene). The RNA transcript was translated in vitro into protein for 90 minutes in the presence of [$^{35}$S]methionine using nuclease-treated rabbit reticulocyte lysate (Promega) and run on 4% denaturing polyacrylamide gels.

Liver Explant Cultures:

Mouse embryos were obtained from Harlan ICR mice. The age of the embryos was determined by days post appearance of the vaginal plug (day 0). The embryos were further characterized by the number of somites. Isolation of mouse hepatic endoderm, liver buds and mesoderm (en bloc dissection) was as follows: during the 10th day of gestation, the liver bud becomes evident as a thickening of the ventral wall of the foregut, near the origin of the yolk stalk. This ventral endoderm was then either taken alone and cultured, or alternatively with the surrounding mesoderm: the portion of the embryo between the otocyst and the umbilical region. Organ culture: Embryos were placed into nucleopore filters in a humid chamber as described (Houssaint, 1980, supra) and cultured for 48 hours or 96 hours. Microscopy: The explants were fixed as in the in situ hybridization protocols, and RNA isolated as described above. 7 mm sections were stained with hematoxylin, eosin and periodic acid schiff (PAS) for glycogen, an indicator of differentiated hepatocytes. For RNA analysis, semiquantitative RT-PCR was performed as described in FIGS. 19 and 20. The invention contemplates the use of such liver explant culture for tissue engineered composites as a form of liver restoration therapy.

Immunohistochemical Characterization:

Antibody to a peptide corresponding to amino acids 145-157 (CLRRKYRSREQPQS) of praja1 (COVANCE), was used for immunohistochemical localization in liver explant cultures. Embryos were fixed and embedded into paraffin, sectioned and immunostained using indirect immunohistochemistry according to protocols routinely used (Schevach, *Current protocols in immunology*, Green Publishing Associates and Wiley Interscience, 1991). 8 μm sections were deparaffinized in xylene, the tissue rehydrated in graded alcohols, and rinsed in PBS. The sections were initially treated with a protease (0.1% Trypsin in 0.05 M PBS) and incubated at 37° C. for 30 min. Endogenous peroxide was then removed using 3% hydrogen peroxide. Sections were blocked in PBS containing 5% goat serum for 30 min. at room temperature. Sections were then incubated overnight at 4° C. in a Humidor with diluted rabbit anti-mouse antibody directed against the PRAJA1 peptide. all further steps were done at room temperature. Six 5 min. rinses with PBS-S were performed after each successive step. After incubation in the primary antisera, slides were washed six times for 5 min. in 1×PBS at room temperature. Sections were incubated with a second antibody (diluted in 0.05 M PBS in 1% serum) for 30 min. at room temperature.

After rinses the substrate was added as follows: Insoluble Peroxidase substrate DAB (Sigma Fast). 100-150 microliter substrate solution was added to cover the entire tissue on the slide. Color development was monitored under microscope. After rinsing in distilled water for 5 min, staining was performed with Harris hematoxylin solution modified (Sigma) for 1 min., followed by a rinse in distilled water for 5 min. Sections were dehydrated by passage through distilled water, then graded alcohol concentrations and finally xylene. Coverslips were mounted using DPX (Fluka labs) or Permount (Fischer scientific), before observation. For the negative controls only the primary antibody diluting solution was added, without any antibody.

Generation of Antibodies:

Peptide-specific rabbit anti-mouse polyclonal antibodies to sequences in the N-terminal and C-terminal of ELF3 were generated as described in Porter et al., *J. Cell. Biol.* 117:997-1005 (1992). The sequences of the synthetic peptides were ELQRT SSVSG PLS (residues 2 to 14 at N-terminus) for the preparation of EL-1, and FNSRR TASDH SWSGM (residues 2140 to 2154 at C-terminus) for the preparation of EL-2. IgG was isolated from antisera by Protein A/G column (Pharmacia), and applied to affinity columns to which the appropriate synthetic peptides had been covalently linked (Pharmacia). The columns were washed with several volumes of buffered saline and then eluted with Elution buffer (pH 2.8, Pharmacia). The eluted fractions were collected into tubes containing sufficient 1 M Tris-HCl, pH 8.0, to bring their pH to 7.2. Affinity-purified antibodies and the antibody fractions that failed to bind to the affinity column were dialyzed against buffered saline containing 10 mM $NaN_3$ and stored at 4° C.

The specificity of the antibodies was assesses by enzyme-linked immunosorbant assays (ELISA), following the method of Engvall (*Methods Enzymol.* 70:419-439, 1980), and by immunoblotting of the synthetic peptides separated by SDS-PAGE. The results from ELISA confirmed the specificity of the antibodies for their corresponding antigens, as did the immunoblotting.

EXAMPLE 3

In accordance with the present invention, genes such as the ones discussed above which are involved in growth and differentiation of hepatocytes will also be involved in liver repair. This is important because cirrhosis or end stage liver disease is: (1) the fourth most common cause of death in the U.S; (2) related to fibrosis and nodular hyperplasia; (3) an important risk factor for hepatocellular carcinoma; and (4) currently has no suitable medical treatment.

One such mode of treatment will be the use of the elf protein, such as the three isoforms elf 1-3 as set forth above. In FIG. 13, the ELF spectrin membrane skeleton is shown. Spectrins are rod shaped, alpha and beta subunits. Helix linked by short actin filaments at junctional complexes that include AE2, protein 4.1, myosin. This membrane skeleton attaches to the plasma membrane at 2 sites, by ankyrin and the beta subunit of spectrin.

In FIG. 14, a comparison of ELF3 and 1 to Beta general spectrin is shown. Spectrins have three domains: Domain I binds Actin; Domain II binds to ankyrin; and Domain III dimerizes spectrin and gives tissue specificity. Sharp differences occur at the amino and C terminal ends. ELF1 differs from ELF3 in that it does not have an ankyrin binding domain.

Further studies have shown that the functional role of ELF may be associated with the ankyrin binding domain. Through antisense oligonucleotides to the ankyrin binding domain, ANK1 inhibits membrane associated ELF3. In addition, the inhibition of the ANK binding domain of ELF3 may result in the loss of intrahepatic bile ducts. This has a phenotype similar to Primary Biliary Cirrhosis (PBC): a disease of unknown etiology resulting in the destruction of Small and Medium sized intrahepatic Bile Ducts.

ELF has a distinct pattern of ELF expression in primary biliary cirrhosis, such as shown in FIG. 15. In panel A—a decrease in membrane labeling of ELF in early PBC is shown. In panels B and D—moderately advanced PBC is shown along with an absence of membrane labeling with a concomitant increase in cytoplasmic labeling of ELF. Panel C shows the absence in ELF labeling in fibrotic cirrhotic PBC tissue, lacking hepatocytes.

Accordingly, the evidence shows that ELF1 and 3 are Beta Spectrins expressed in bile duct epithelial cells and hepatocytes. In addition, ELF3 (membrane spectrin) inhibition leads to loss of intrahepatic bile ducts in explant cultures, with increased presence of lymphocytes. Decreased membrane labeling of ELF and marked increase in cytoplasmic labeling characterize PBC.

Further, antisense studies appear to show a primary role for ELF in PBC. Antibody studies in PBC support the role of ELF in its pathogenesis. Abnormal distribution of ELF may affect intracellular trafficking and may explain changes in AE2 expression and the resulting cholestasis seen in PBC.

Since the above reflects the mechanism by which ELF disruption results in primary biliary cirrhosis, investigations were made as to whether there were other pivotal protein interactions involved. Recent studies in smad2/3 mutants suggested the involvement of the TGF Beta pathway in PBC and the ultimate use of the elf proteins of the present invention in treating or preventing PBC and other liver diseases.

Transforming growth factor-β (TGF-β) is the major cytokine involved in organ fibrosis. It inhibits growth of hepatocytes and some hepatocellular carcinomas (HCC). The SMAD proteins serve as intracellular mediators of TGF-β and activins. TGF-Beta receptor activation involves phosphorylation of SMAD2 and SMAD3 and heteromeric complexes with SMAD4, such as shown in FIG. 16. Complexes translocate to the nucleus to control expression of target genes.

Studies that shown that animals lacking smad2 die before 8.5 days of development (E8.5), and thus smad2 is required for gastrulation and mesoderm induction. Animals lacking smad3 are viable but suffer mucosal immunodeficiency.

To investigate potential genetic cooperactivity in the smad gene family, we intercrossed strains lacking smad2 and smad3. These studies showed that (1) Mice doubly heterozygous for disruptions of the smad2 and smad3 genes display novel phenotypes not present in either single heterozygous; (2) Mutants die at E14 with marked liver hypoplasia; (3) 1-2% of smad2+/− smad3+/− animals survived to weaning; and (4) Mutant livers occur in 30-40% of the wild type.

Immunohistochemical analysis was conducted of hypoplastic liver sections using antibody to alpha-fetoprotein, and the results are shown in FIG. 17. In FIG. 17, Panel A shows wild type liver sections, cords of well organized and differentiated embryonic hepatocytes. Early primitive bile ducts are seen. On the other hand, Panel B of FIG. 17 shows smad2/3 mutant embryos, where hepatocytes are present, but normal cell architecture is lost. In addition, there is an absence of cell plates, and only primitive bile ducts.

Figures 18A, 18B:
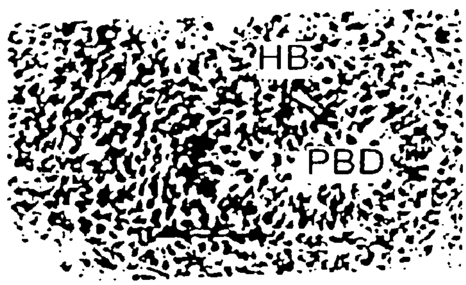
FIG. 18 depicts apoptosis in smad2 and smad3 mutants.

Explant embryonic liver from mutants were cultured with HGF in an attempt to rescue the mutant embryos. When mutant embryonic livers were cultured in the presence of cardiac mesoderm, severe apoptosis occurred as seen in FIG. 18*b*, compared to wild type cultures in FIGS. 18*a* and 19*a* with good hepatic growth.

Figures 19A, 19B, 19C:
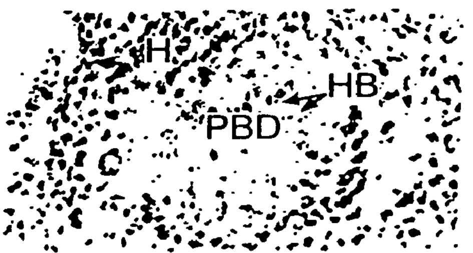
FIG. 19 depicts rescue of the hepatic phenotype by culturing in the presence of HGF.

Mutants cultured in the presence of HGF (5/50 ng/mL) show a rescue of the hepatic phenotype, with the formation of well differentiated hepatocytes, as well as primitive bile ducts as seen in FIG. 19*c*.

These tests also showed that smad2/smad3 mutant embryos die at day 14 with profound anemia and liver hypoplasia, and hepatic stem cell proliferation in the smad mutants is dramatically reduced. Hepatocyte and erythrocyte differentiation in the smad mutants is reduced by 10%, and HGF can rescue the hepatic phenotype in explant cultures.

Accordingly, it appears that Smad 2 and 3 are essential for hematopoisis and growth of developing liver. Gut and hepatic lineage are not altered in smad mutant mice. Smad 2 and 3 thus appear to be required for hepatic stem cell proliferation and cytoskeletal organization.

Moreover, ELF inhibition results in a phenotype with features suggestive of primary biliary cirrhosis (PBC). ELF expression is identical in smad2/3 mutants and PBC. It thus appears that smad2/3 is involved in the pathogenesis of PBC. Evidence for this includes the suppression of smad3 in PBC; Smad2 nuclear localization absent in PBC; Smad2 and 3 bind to ELF in PBC tissue; Smad2/3 mutants have a severe but similar phenotype seen in primary biliary cirrhosis; and cytoskeletal protein interactions with ELF spectrins play a pivotal role in the pathogenesis of primary biliary cirrhosis.

It thus appears that genes such as the elf 1,3 proteins of the present invention and smads 2,3 which are involved in growth and differentiation of hepatocytes will be involved in liver repair seen in diseases such as primary biliary cirrhosis.

In summary, transforming growth factor-β (TGF-β) is a major cytokine involved in multiple cellular processes including differentiation, proliferation, migration, fibrosis and apoptosis, and SMAD proteins serve as intracellular signaling molecules of TGF-β and activins. In novel phenotypes with smad2/3 intercrosses, almost all mutants died at E14 with marked liver hypoplasia and loss of primitive bile ducts. The smad2/3 mutants were notable for a marked fall in the expression of elf3, a β-spectrin in accordance with the present invention. Antisense studies to elf3 and studies in tissue from patients with primary biliary cirrhosis suggest that a crucial role for ELF in this disorder and intrahepatic bile duct formation. In addition, smad2/3 mutants have a severe but similar phenotype seen in primary biliary cirrhosis. SMAD2, and SMAD3 bind to ELF3. These results taken together suggest that elf gene is an important player in intrahepatic bile duct formation and cirrhosis, and this process involves Smad2 and Smad3.

In short, ELF interactions with TGF Beta signaling molecules Smad2 and 3 are crucial for bile duct formation, as well as cirrhotic conditions such as PBC.

EXAMPLE 4

In our search for genes that are involved in liver repair, we utilized a specific cloning strategy of subtractive hybridization with embryonic liver cDNA libraries, and identified two novel Beta Spectrins termed elf(4), such as disclosed above. Antisense studies utilizing cultured liver explants show a vital role of elf3 in hepatocyte differentiation and intrahepatic bile duct formation, and to be a marker in cirrhosis. A similar loss of intrahepatic bile ducts is noted in smad2/3 knockouts. Notably ELF expression is diminished in these knockouts. Furthermore, we have shown that ELF binds directly and specifically to TGF Beta signaling molecules Smad2 and Smad3. Together, these results suggest a model in which ELF interactions with Smad2 and Smad3 are pivotal for bile duct formation.

These results suggest that ELF interactions with TGF Beta signaling molecules Smad2 and 3 are crucial for bile duct formation, as well as cirrhotic conditions such as PBC. Experiments performed on these molecules have given initial information of the mechanisms associated with cirrhosis and repair and how ELF and the TGF Beta signaling pathway activate these regulatory mechanisms.

These results demonstrate that elf is expressed as four transcripts in the liver, a 9.0 Kb primary transcript and three secondary transcripts (5 Kb, 4.0 Kb and 2.4 Kb). In addition, studies have shown an interaction between endogenous ELF and Smad2. For this, ELF was immunoprecipitated from liver lysates and HepG2 cells using an affinity-purified anti-ELF polyclonal antibody, and Smad2 and 3 were visualized by immunoblotting with anti-Smad2 and anti-Smad3 antibody. In immunoprecipitates prepared with preimmune antisera, no Smad2 was detectable. However, in the anti-ELF immunoprecipitates, we could clearly detect Smad2 and 3 coprecipitating with ELF. Together, these results demonstrate that ELF is a specific partner for receptor-regulared Smads 2 and 3 in the TGFβ/activin signaling pathway. Our biochemical analyses of ELF/Smad2 and Smad3 interactions suggest that ELF functions upstream in the pathway and might control the subcellular localization of Smad2 and Smad3.

Other important information of relevance to the usefulness of the elf proteins of the present invention relates to the following compounds or factors:

Transforming Growth Factor-Beta (TGF-Beta)

Transforming growth factor-Beta (TGF-Beta) represents an extensive family of growth and differentiation factors including activin/inhibins and bone morphogenetic proteins (BMPs) (Heldin et al., 1997), that mobilize a complex signaling network to control cell fate by regulating proliferation, differentiation, motility, adhesion, and apoptosis. TGF-Beta promotes the assembly of a cell surface receptor complex composed of type I (TbRI) and type II (TbRII) receptor serine/threonine kineses. In response to TGF-Beta binding, TbRII recruits and activates TbRI through phosphorylation of the regulatory GS-domain. Activated TbRI then initiates cytoplasmic signaling pathways to produce cellular responses. SMAD proteins together comprise a unique signaling pathway with key roles in signal transduction by TGF-Beta and related factors. The founding member of the SMAD family, Mothers against dpp (Mad) was identified as a dominant enhancer of weakly mutant alleles of decapentaplegic, a BMP homologue in *Drosophila melanogaster* (Raftery et al., 1995; Sekelsky et al., 1995). Genetic screens in *Caenorhabditis elegans* for mutant phenotypes like those observed for Ser/Thr kinase receptors daf-1 and daf-4 revealed three genes, sma-2, sma-3 and sma-4, with homology to Mad (Savage et al., 1996). At present, nine vertebrate SMADs have been identified (Attisano and Wrana, 1998). They are characterized by homologous regions at their N- and C-termini known as Mad homology (MH)-1 and MH-2 domains, respectively.

Three classes of Smads with distinct functions have been defined: the receptor-regulated Smads, which include Smad1, 2, 3, 5, and 8; the common mediator Smad, Smad4; and the antagonistic Smads, which include Smad6 and 7 (Heldin et al., 1997; Attisano and Wrana, 1998; Kretzschmar and Massague, 1998). Receptor-regulated Smads (R-Smads) act as direct substrates of specific type I receptors, and the proteins are phosphorylated on the last two serines at the carboxyl terminus within a highly conserved SSXS motif (Macias-Silva et al., 1996; Abdollah et al., 1997; Kretzschmar et al., 1997; Liu et al., 1997b; Souchelnytskyi et al., 1997). Regulation of R-Smads by the receptor kinase provides an important level of specificity in this system. Thus, Smad2 and Smad3 are substrates of TGFβ or activin receptors and mediate signaling by these ligands (Macias-Silva et al., 1996; Liu et al., 1997b; Nakao et al., 1997), whereas Smad1, 5 and 8 are targets of BMP receptors and propagate BMP signals (Hoodless et al., 1996; Chen et al., 1997b; Kretzschmar et al., 1997; Nishimura et al., 1998). Once phosphorylated, R-Smads associate with the common Smad, Smad4 (Lagna et al., 1996; Zhang et al., 1997), and mediate nuclear translocation of the heteromeric complex. In the nucleus, Smad complexes then activate specific genes through cooperative interactions with DNA and other DNA-binding proteins such as FAST1, FAST2, and Fos/Jun (Chen et al., 1996, 1997a; Labbe et al., 1998, Zhang et al., 1998; Zhou et al., 1998). In contrast to R-Smads and Smad4, the antagonistic Smads, Smad6 and 7, appear to function by blocking ligand-dependent signaling (reviewed in Heldin et al., 1997).

Genetic analysis in *Drosophila melanogaster* and *Caenorhabditis elegans*, as well as TbRII and SMAD mutations in human tumors, emphasizes their importance in TGF-Beta signaling. Collectively, these factors constitute a communication network exploited by TGF-Beta family members to regulate gene expression, and suggest a paradigm in which signaling pathways activated by ligand binding and operating in parallel, converge at target promoters to produce ligand specific responses.

Receptor Interacting Proteins

Proximal signaling events coupling TGF-Beta receptor activation to biological responses involves proteins, such as FKBP12, Drosophila inhibitor of apoptosis (DIAP)-1 and -2 (Oeda et al., 1998), and TbRI associated protein (TRAP)-1 and -2 (Charng et al., 1998). The WD-domain protein TRIP-1 and TbRII (Chen et al., 1995), that directly bind the receptor complex, FKBP12, a binding protein for the macrolide immunosuppressant FK506, interacts with a Leu-Pro motif in the GS-domain of TbRI and other type I receptors (Wang et al., 1996, Chen et al., 1997). (Wang et al. 1996). Phosphorylation of R-Smads by the type I receptor is essential for activating the TGFβ signaling pathway (Heldin et al., 1997; Attisano and Wranga, 1998; Kretzschmar and Massague, 1998). However, little is known of how Smad interaction with receptors is controlled. Recently, a novel Smad2/Smad3 interacting protein that contains a double zinc finger, or FYVE domain, and has been identified called SARA. SARA recruits Smad2 into distinct subcellular domans and that SARA colocalizes and interacts with TGFβ receptors. TGFβ signaling induces dissociation of Smad 2 from SARA with concomitant formation of Smad2/Smad4 complexes and nuclear translocation. Moreover, deletion of the FYVE domain in SARA causes mislocalization of Smad2 and inhibits TGFβ-dependent transcriptional responses. Thus, SARA defines a component of TGFβ signaling that functions to recruit Smad2 to the receptor by controlling the subcellular localization of Smad.

SMAD Domain Functions and Regulation by Intrinsic and Extrinsic Mechanisms

The MH2 region of pathway-restricted SMADs is involved in protein-protein interactions, particularly with other transactivating factors, such as interaction between Smad2 and the winged-helix transcription factor FAST-1 (Chen et al., 1996). Similarly, between Smad3 and the transcriptional coactivator CBP/p300 (Fen et al., 1998; Janknect et al., 1998). Additionally, the MH2 domains are responsible for homomeric and heteromeric interactions between SMADs (Zhang et al., 1997).

SMAD proteins reside in the cytoplasm, and upon stimulation translocate to the nucleus as part of an oligomeric complex (Attisano and Wrana, 1998). The observation that MH1 domain deletion from Smad2 results in constitutive nuclear localization (Baker and Harland, 1996) suggests an intrinsic inhibitory role for the MHI domain in signaling by pathway-restricted SMADs. Intrinsic inhibition of SMAD function mediated by the MH1 domain is relieved by agonist induced phosphorylation of the -SSXS motif, which presumably antagonizes the intramolecular MH1-MH2 interaction (Eppert et al., 1996; Schutte et al., 1996).

The MH1 domain is also involved in direct DNA binding. The MH1 domain Mad is necessary and sufficient for binding to the "quadrant" enhancer of the vestigal (vg) wing patterning gene in *D. melanogaster* (Kim et al., 1997). Similarly, Mad binds to the Dpp response element in the Ultrabithorax (ubx) promoter via its MH1 domain. Direct interaction of Smad3 and Smad4 with a CAGA-box, a DNA element repeated three times in the TGF-Beta responsive regions of the plasminogen activator inhibitor (PAI)-1 promoter has also been shown. This interaction requires the MHI domain of both Smads. Smad3 additional requires either agonist stimulation or MH2 domain deletion. In a basal state, MH1 and MH2 domains provide intrinsic, reciprocal inhibition that is liberated by receptor activation and -SSXS phosphorylation.

Involvent of extrinic regulatory pathways such as the ERK MAP kinase pathway also contribute to SMAD regulation. In response to mitogenic growth factors such as epidermal growth factor (EGF) that signal through receptor tyrosine kinases (Denhardt, 1996), ERK-mediated phosphorylation of target transcriptional regulators contributes to the mitogenic influence of these factors. Recently, multiple serine residues in the linker region of Smad1 were shown to be phosphorylated by ERK, both in vitro and in vivo in response to EGF (Kretzschmar et al., 1997b). While phosphorylation of Smad1 by ERK was independent of -SSXS phosphorylation and did not effect association with Smad4, it did antagonize nuclear translocation of the SMAD oligomeric complex in response to BMP stimulation. ERK mitogenesis may involve simultaneous potentiation of growth promoting pathways and attenuation of growth inhibitory pathways.

In addition, Ca2+ dependent interaction between calmodulin (CaM) and several SMAD family members has been described (Zimmerman et al., 1998). CaM bound the N-terminal half of Smad2 between residues 76 and 208. Both CaM coexpression and a CaM-specific antagonist suggested a negative regulatory role for CaM in both activin and TGF-Beta signaling in a transient assay. Given the wide array of factors regulated by CaM either directly via protein-protein interaction or indirectly by CaM-dependent kineses, it is attractive to speculate that CaM influences SMAD protein function in response to agents that regulate intracellular Ca2+ flux.

Finally, other groups of proteins in which mammalian homologues may be important in liver formation due to interactions with the ELF proteins of the present invention are the family of growth factors produced by the fat body and which are active on *Drosophila* imaginal disc cells, such as disclosed in Kawamura et al., *Development* 126:211-219 (1999), incorporated herein by reference.

What is claimed is:

1. An isolated antibody wherein the peptide recognized by the antibody is selected from the group consisting of the peptide consisting of the amino acid sequence set forth in SEQ ID NO:21, the peptide consisting of the amino acid sequence set forth in SEQ ID NO:22, the peptide consisting of the amino acid sequence set forth in SEQ ID NO:23, the peptide consisting of the amino acid sequence set forth in SEQ ID NO:24, the peptide consisting of the amino acid sequence set forth in SEQ ID NO:25, the peptide consisting of the amino acid sequence set forth in SEQ ID NO:26, the peptide consisting of the amino acid sequence set forth in SEQ ID NO:27, and the peptide consisting of the amino acid sequence set forth in SEQ ID NO:28.

* * * * *

SEQUENCE LISTING

```
<160> NUMBER OF SEQ ID NOS: 28

<210> SEQ ID NO 1
<211> LENGTH: 5434
<212> TYPE: DNA
<213> ORGANISM: Mus musculus
<220> FEATURE:
<221> NAME/KEY: misc_feature
<222> LOCATION:
<223> OTHER INFORMATION: n=a or c or t or g
<220> FEATURE:
<221> NAME/KEY: CDS
<222> LOCATION: (1674)..(2069)

<400> SEQUENCE: 1

tcgggaaang attgatttgg ccncctcggn aaggcntttt attttgcnnc aaggagggcc      60

cggggggttt ccaaccnaaa taaaattttt tttcggatcc cgggggtttc ctcagggagt     120

tggggaattt tactttgaaa gcagatnttt cngagntccg ggtagctntc caataactnt     180

ttgtcatcat tgccagacgg cagatcaagg atgccttcgg tttacccgtg ctgttcagag     240
```

-continued

```
aacggctttt ggaagattga ttttaagtta tttaacagtc acagacaggt gtcatntntg    300

gagaatagag gcaagtccgc ggtgagggat gaagcaggag agattagggg aaggcagaca    360

ggactgctgg gccaaggaag ctgtgctgat ttgagcacag tgggaattca cgtacgcaat    420

ttcaaaggct ttagtggtaa attctgaagc tcagatgcag gcaagaccca agaggatagt    480

gtacacagag agaagagggt cntcaggatc gtgcgtagag tggagagagc cccaaaggca    540

ggagggaaga gcctcagtga ttacttaggg atgagggaga gaagaaaaaa ggttcttgca    600

aggtgtgggg tcttccaaat tcaggagttc actgccatat agagaaggtg tagcgggtga    660

aaggggccat gtgatgagga tggcaagcaa ggctgtggcg cagatgacga gatgcctggg    720

tcgggaggtc aggggagacc caggattggg gtcacctgtg tctgcgcaga ggggaagcca    780

ccctgcaact ggcccagcac tgagtccaga ggaaaatgag gcagaggaca aaccagagct    840

tcggagacta agtgcaggta gggcgcgggc ggagcgtgag gagggcagcg gaccacgcga    900

gaggcctcga aggccaccgg acccgcgtcc gagagtctga gggccctgcc cacacctgcg    960

tggccccctc cccagaggcc acactccaag gccaccctag aacccgtctg tctgctcaag   1020

cccttgcaaa agacgtctgc gcagaggggg cgtggcaggc gtgctgtcac tcacggcctg   1080

ttagccaatc cacgagtgcg cccctccccg gagagggtgc gcggagggcc cgcccccgcc   1140

gccaccgcgg gtgtgaggag gccaggctgg cgcggctccc tccgcccggc agccttgcca   1200

ggtaaccggg ttcggcggga gggctggggg tcgcgcagcc ccctcgctcc ctgggaggcg   1260

tgcacactgc cgcggcgggt cccgtgtggg ccggaggccc gtgcgcgcgt cggaccgacg   1320

ggccgcagcc tgtgggcggg gttgcgtgcg tgacgggcgg ccgtgccccg cgttgtgtca   1380

ggcctgcgcg gggaaagctc ggccgaaccg aggtgtccag gtccgcccgc tgcggcctgc   1440

cccgggttgc ggggcgcagg cgcggcggtg ggcgggggtc gtccccagga gcgtctttgt   1500

tcccggcgcg ctgagggcgg agcctcaccc cgccccgccc ccgcgctcag tccccgcccc   1560

gcgtccgccc gcaggagctg ccaccgggtc ccgctggcct ccccggccgc cgccaccgcc   1620

tccgcctccg ccgctccggg cccgccggct tgcgtcgccg aggtcgctgc agc atg      1676
                                                           Met
                                                             1

gcg ggc gtc gcg acc ccc tgc gcc aac ggc tgc ggg cct ggc gca ccc      1724
Ala Gly Val Ala Thr Pro Cys Ala Asn Gly Cys Gly Pro Gly Ala Pro
            5                   10                  15

tcc gaa gcc gag gtg ctg cac ctc tgc cgc agc ctc gag gtg ggc acc      1772
Ser Glu Ala Glu Val Leu His Leu Cys Arg Ser Leu Glu Val Gly Thr
        20                  25                  30

gtc atg act ttg ttc tac tcc aag aag tcg cag cgg cca gaa cgg aag      1820
Val Met Thr Leu Phe Tyr Ser Lys Lys Ser Gln Arg Pro Glu Arg Lys
    35                  40                  45

acc ttc cag gtc aag ttg gag acg cgc cag atc aca tgg agc cgc ggc      1868
Thr Phe Gln Val Lys Leu Glu Thr Arg Gln Ile Thr Trp Ser Arg Gly
50                  55                  60                  65

gcg gac aaa atc gag ggg tcc agt aag tgc gcc cca ctc cgg cct gcc      1916
Ala Asp Lys Ile Glu Gly Ser Ser Lys Cys Ala Pro Leu Arg Pro Ala
                70                  75                  80

tcg cgc ctg ccc gcc tcc caa aca ctt ggg caa act ttc ggg cct cgc      1964
Ser Arg Leu Pro Ala Ser Gln Thr Leu Gly Gln Thr Phe Gly Pro Arg
            85                  90                  95

gcc tgg cgc ccc gtc tcc gcc cag tcc ctg gtg gtc act ctg ggg cgg      2012
Ala Trp Arg Pro Val Ser Ala Gln Ser Leu Val Val Thr Leu Gly Arg
        100                 105                 110

gtg gag ggg ggc atc cgg gtc ttg gat cac ctg ata gga cac ccc ctc      2060
```

-continued

```
Val Glu Gly Gly Ile Arg Val Leu Asp His Leu Ile Gly His Pro Leu
    115                 120                 125

ccc cag tag ggggggagtg ttccaggcac tttgccctga ggcctaagag            2109
Pro Gln
130

tcctcactgg ttggacaagt ggagtgggat tccggccctt agcatcgggc ggctgtcagt   2169

ggctgtgagg ggaagccaag acagggaccc cctcatccaa cctgagaacc tggggaaccg   2229

acaagatctt cctgcccact gccatttctc cagagtgtgc tgtctgtgaa aactcctaag   2289

agctccggga tgggcttatt ggcgcaagaa cctttggaat cctcatgtag aacttaggca   2349

gatgttgggg tagggctggt tgtgaagcag agccctactc atctcccctc ttctttggga   2409

ggatggggta tgaaagctaa aaccgtgact gcttcccccct cccatgtccc gtggatgggt   2469

ttttttttt ttttttttg ccccagatct gaattttgga ggtccatggt gctaggcagc   2529

catccaaagc tagagccatg gctcctttgc ccttgcagca tataacaagg agcttgcatt   2589

cagaaaggtt ccctggcctt gggttttggg gtccagccct ttgtgttgga tgttctcgtg   2649

accacagggt agcccagagt tgctcctctg gtttcctgtc gtacccttcc caaacctgag   2709

tgtggtgggt ttacacacaa gtctctggtg ggagaagtaa gtcaggagtt ttgagaaacc   2769

tcggctcttt ctgatagtca ttttcctcgg tgtgaggcag gatgaggagt ctttgcaact   2829

ccaggctttg agatgtttct tacaagaacc cccaaagagt ctatggttga agggacctag   2889

cctaagagcc aggtctgtgt tagagaaggg ggggtggtgt caggaagtaa caacggagag   2949

aaggtcccac agatcttcct ggggatggtg tacatgtgtg tcgatgggtg aggagatgag   3009

gaggaaggaa ggtttctgtg gtaagacagc catcctcaac tacaaacttc aggtctgaca   3069

gaattggccc ttaaccatca ccagtgccca tcagccctgg cctccgctgg aagaacattt   3129

cagtgatttt cagtgttggg ggatggaact gcagacagtt ccggtagtcc tgagacatca   3189

ctcagacatc aggttgcagg catggcattt tacgtttgta gtatttcctg tgtttaagtg   3249

gtggcattag ttccccggta gctagctctt ggtaacagct gcactgtaaa ccgtgtgtgt   3309

agcccagtag tggaagatag ctatggtatt tgaagccagt gtgttagctg tacgtcaccc   3369

agccaggtgc tttccctctc ggagcctcgg ttcctctgta agttagcaga agtatattta   3429

ctataaatgg tcacttttgg aagtgagata gttggtgtaa agtaagcaaa ctaaatatgt   3489

aatagatgcg agcagagacg ttacagaagt ttaagaacca gttattagta gcagtagcta   3549

tggtagatgc ttgtcctcct agaccctggg atggggcttc tgagggaggt ctaatgtggc   3609

tgttagaaaa agaaagggct ctgagggagg agggccgaga gagggtcccg ttctccttaa   3669

ttgcattacc caggataaaa gaggaaactc ttgttttgcc gtacatcgtt tacccttctg   3729

ttcacctgtc atgtaagatg agtttctatg tttggaattt tgtacattgg atgccattgt   3789

gagttggggc ctggacagaa agaagggact tagagacaga accatccagt ccgttttgtc   3849

tcacttgggt ctttgaggat gggtggcagg aatacagagg acgtcacctt tccagaccca   3909

caaaagtcac ccagagatat gcatgttttc attgggcccg accctgtgat ttttggggtc   3969

cagaatgaag gctgcagact agcctgtgtg gacttcatac cttgtaaatg gagcccacca   4029

ccgaagccct gccccacttc tgctggaatg cacctcactg cctttgtggg ttcccaaacc   4089

tgcagcctcc tgcagattgt gaaaaggatt gagttgccag ctgggtccct actgtctggt   4149

ctcttgttca gatgcctcag gtatttgact ttttgctgat aaccttatcc ctacctgaag   4209

ccaggccaga gagaaagact gccgctgtct gccctcaggg tgctcacgga acacaacgac   4269
```

-continued

```
aggctgactg ccatttccta aatcttgagt tctctcactg tgacacctgt gaaactagtt   4329

agcaccttct gatgtctaag gcagcggtct acttgagaag tgctttggtg ctgtttggtt   4389

gtgtgactga agtcaggctg gtgtctggca tttatgttgc agaatttagt gagttaaaag   4449

cagccataga cttcctgccc agtgctaaac agacttttca ctctgctgca ggctagtcct   4509

cagaggactc tgctcccagg ttgtgttggt ggtaggcctt ggtctcctgt tttctgtagc   4569

ctttgttgcc ccttgtgaag agaaacctcc atgtttaggt ggtatttaca ggcagagacc   4629

tccatcttca tcaaagacgc cttcctaggc tttccatatg taatgcctgt agtgagatgg   4689

ctcagaccta ttcttcgtga ggttgtccag ttaaggacca ctgttggcat agtagctcca   4749

gtagagactc taaagctatg ttgttattgt ggtgaggatt gcagtaccaa ggggctggct   4809

ctgagagtag gtccgtggca cctaagaatt gtctgcacat gtccctcaag gattcctttt   4869

ngctggccca cagtgagaga gcagcagaaa gcatgcgcct ggatctaaga aaggttaatg   4929

aaaccatggt acctatggga gctttacaac ctgggcttct gtctccggta gccatttcta   4989

aaaganatta tgaaattgtg gtagattgaa agatgttcct tactattcct ttacatcctg   5049

aggatcacga aagatttgct ttcagtattc ctactattaa ttttaaagaa cctatgaaaa   5109

gatatcaatg gacagttctt ccacaaggca tggctaataa tcctacctta tgtcaaantt   5169

gtggcacaac cattcacctg tgagacacaa tgactatgac tactcntcnt gatgatgatg   5229

angatgatga gatgatgatg atgatgatga tgacacacan gatagagatg attctaangc   5289

ggaaanatcc cgactgcttt ncttaaaatt accnncctnc gaaaagatta aacccgaaag   5349

gtcaccgatc tatatttngt ttaantnata ccgtttccca aaattttncg gacctnaant   5409

ttnatcaatt ttgtntatgn tcccc                                         5434
```

```
<210> SEQ ID NO 2
<211> LENGTH: 131
<212> TYPE: PRT
<213> ORGANISM: Mus musculus

<400> SEQUENCE: 2

Met Ala Gly Val Ala Thr Pro Cys Ala Asn Gly Cys Gly Pro Gly Ala
  1               5                  10                  15

Pro Ser Glu Ala Glu Val Leu His Leu Cys Arg Ser Leu Glu Val Gly
             20                  25                  30

Thr Val Met Thr Leu Phe Tyr Ser Lys Lys Ser Gln Arg Pro Glu Arg
         35                  40                  45

Lys Thr Phe Gln Val Lys Leu Glu Thr Arg Gln Ile Thr Trp Ser Arg
     50                  55                  60

Gly Ala Asp Lys Ile Glu Gly Ser Ser Lys Cys Ala Pro Leu Arg Pro
 65                  70                  75                  80

Ala Ser Arg Leu Pro Ala Ser Gln Thr Leu Gly Gln Thr Phe Gly Pro
                 85                  90                  95

Arg Ala Trp Arg Pro Val Ser Ala Gln Ser Leu Val Val Thr Leu Gly
            100                 105                 110

Arg Val Glu Gly Gly Ile Arg Val Leu Asp His Leu Ile Gly His Pro
        115                 120                 125

Leu Pro Gln
    130


<210> SEQ ID NO 3
<211> LENGTH: 6960
<212> TYPE: DNA
```

```
<213> ORGANISM: Mus musculus
<220> FEATURE:
<221> NAME/KEY: CDS
<222> LOCATION: (333)..(6794)

<400> SEQUENCE: 3

cctgcgtcct tcctcctttt cctccttccc tcctccctcc cgggtaattt atttctagct      60

tccaggcaag ggccacacaa ggaaggaaat ccacagggga ttagatgccg gggtggtaac     120

tccaccaggc taggttggac tctgcagcca acttcctatc agatcaccct gcacctattt     180

ccgacccgac cggaatgcga ctggcttgag gtccagccct ttcgcctggg cgggagcaga     240

gccgcggaag ctgcttggag ttggatgggg gtaggaaggg gctggagcgg gaatcctacg     300

atgcaactgg cctgggccta aggttgggca ta atg gag ttg cag agg aca tcc      353
                                    Met Glu Leu Gln Arg Thr Ser
                                     1               5

agc gtt tca ggg ccg ctg tcg ccg gcc tac acc ggg cag gtg cct tac      401
Ser Val Ser Gly Pro Leu Ser Pro Ala Tyr Thr Gly Gln Val Pro Tyr
        10                  15                  20

aac tac aac caa ctg gag gga aga ttc aaa cag ctc caa gat gag cgt      449
Asn Tyr Asn Gln Leu Glu Gly Arg Phe Lys Gln Leu Gln Asp Glu Arg
    25                  30                  35

gaa gct gta cag aag aag acc ttc acc aag tgg gtc aat tcc cac ctt      497
Glu Ala Val Gln Lys Lys Thr Phe Thr Lys Trp Val Asn Ser His Leu
40                  45                  50                  55

gca aga gtg tcc tgc cga atc aca gac ctg tac acg gac ctt cga gat      545
Ala Arg Val Ser Cys Arg Ile Thr Asp Leu Tyr Thr Asp Leu Arg Asp
                60                  65                  70

gga cgg atg ctc atc aag cta ctg gag gtc ctc tct gga gag agg ctg      593
Gly Arg Met Leu Ile Lys Leu Leu Glu Val Leu Ser Gly Glu Arg Leu
            75                  80                  85

cct aaa ccc act aag gga cgg atg cgg atc cac tgt ctg gag aat gtc      641
Pro Lys Pro Thr Lys Gly Arg Met Arg Ile His Cys Leu Glu Asn Val
        90                  95                  100

gac aag gct ctt caa ttc ctg aaa gag cag aga gtc cat ctt gag aac      689
Asp Lys Ala Leu Gln Phe Leu Lys Glu Gln Arg Val His Leu Glu Asn
    105                 110                 115

atg ggc tcc cat gac att gtg gat gga aac cac cgg ctg acc ctc ggc      737
Met Gly Ser His Asp Ile Val Asp Gly Asn His Arg Leu Thr Leu Gly
120                 125                 130                 135

ctc atc tgg aca att att ctg cgc ttc cag atc cag gat att agt gtg      785
Leu Ile Trp Thr Ile Ile Leu Arg Phe Gln Ile Gln Asp Ile Ser Val
                140                 145                 150

gag act gaa gat aac aaa gag aaa aag tct gct aag gat gca ttg ctg      833
Glu Thr Glu Asp Asn Lys Glu Lys Lys Ser Ala Lys Asp Ala Leu Leu
            155                 160                 165

ctg tgg tgc cag atg aag aca gct ggg tac ccc aat gtc aac att cac      881
Leu Trp Cys Gln Met Lys Thr Ala Gly Tyr Pro Asn Val Asn Ile His
        170                 175                 180

aat ttc acc act agc tgg agg gat ggc atg gcc ttc aat gca ctg ata      929
Asn Phe Thr Thr Ser Trp Arg Asp Gly Met Ala Phe Asn Ala Leu Ile
    185                 190                 195

cat aaa cat cgg cct gac ctg ata gat ttt gat aaa ctg aag aaa tct      977
His Lys His Arg Pro Asp Leu Ile Asp Phe Asp Lys Leu Lys Lys Ser
200                 205                 210                 215

aat gca cac tac aat ctg cag aat gca ttt aac ctg gca gag cag cac     1025
Asn Ala His Tyr Asn Leu Gln Asn Ala Phe Asn Leu Ala Glu Gln His
                220                 225                 230

ctt ggc ctc act aaa ctg tta gac cct gaa gat atc agt gtg gac cac     1073
Leu Gly Leu Thr Lys Leu Leu Asp Pro Glu Asp Ile Ser Val Asp His
```

-continued

```
            235                 240                 245

cct gat gag aag tct atc atc aca tac gtg gtg act tac tac cac tac     1121
Pro Asp Glu Lys Ser Ile Ile Thr Tyr Val Val Thr Tyr Tyr His Tyr
        250                 255                 260

ttc tcc aag atg aag gcc ttg gct gtc gaa gga aag cgc att gga aag     1169
Phe Ser Lys Met Lys Ala Leu Ala Val Glu Gly Lys Arg Ile Gly Lys
    265                 270                 275

gtg ctt gat aat gct ata gaa aca gag aaa atg att gag aag tac gag     1217
Val Leu Asp Asn Ala Ile Glu Thr Glu Lys Met Ile Glu Lys Tyr Glu
280                 285                 290                 295

aca ctt gct tct gac ctt ctg gag tgg att gaa caa acc atc atc atc     1265
Thr Leu Ala Ser Asp Leu Leu Glu Trp Ile Glu Gln Thr Ile Ile Ile
                300                 305                 310

cta aac aac cgc aaa ttt gct aat tca ctg gtt ggg gtc caa cag cag     1313
Leu Asn Asn Arg Lys Phe Ala Asn Ser Leu Val Gly Val Gln Gln Gln
            315                 320                 325

ctc caa gca ttc aac acg tac cgc aca gtg gag aaa cca cct aag ttt     1361
Leu Gln Ala Phe Asn Thr Tyr Arg Thr Val Glu Lys Pro Pro Lys Phe
        330                 335                 340

act gag aag ggg aat ttg gag gtg ctc ctt ttc gcg att cag agc aag     1409
Thr Glu Lys Gly Asn Leu Glu Val Leu Leu Phe Ala Ile Gln Ser Lys
    345                 350                 355

atg cga gcg aat aat cag aag gtc tac atg ccc cgc gag ggg aag ctc     1457
Met Arg Ala Asn Asn Gln Lys Val Tyr Met Pro Arg Glu Gly Lys Leu
360                 365                 370                 375

atc tct gac atc aac aag gcc tgg gaa aga ctg gaa aaa gca gaa cat     1505
Ile Ser Asp Ile Asn Lys Ala Trp Glu Arg Leu Glu Lys Ala Glu His
                380                 385                 390

gag aga gaa ctg gct ctg cgg aat gag ctc ata cgg cag gaa aaa ctg     1553
Glu Arg Glu Leu Ala Leu Arg Asn Glu Leu Ile Arg Gln Glu Lys Leu
            395                 400                 405

gaa caa ctc gcc cga aga ttt gat cgc aag gca gct atg agg gag aca     1601
Glu Gln Leu Ala Arg Arg Phe Asp Arg Lys Ala Ala Met Arg Glu Thr
        410                 415                 420

tgg ctg agt gaa aac cag cgt ctt gtg tct cag gac aac ttt gga ttt     1649
Trp Leu Ser Glu Asn Gln Arg Leu Val Ser Gln Asp Asn Phe Gly Phe
    425                 430                 435

gac ctt ccc gct gtt gag gct gct acc aaa aaa cac gag gcc att gag     1697
Asp Leu Pro Ala Val Glu Ala Ala Thr Lys Lys His Glu Ala Ile Glu
440                 445                 450                 455

aca gac atc gct gca tat gaa gaa cga gtt cag gcc gtg gtg gct gtg     1745
Thr Asp Ile Ala Ala Tyr Glu Glu Arg Val Gln Ala Val Val Ala Val
                460                 465                 470

gcc agg gaa ctt gaa gcc gag aac tac cat gac atc aag cgc atc aca     1793
Ala Arg Glu Leu Glu Ala Glu Asn Tyr His Asp Ile Lys Arg Ile Thr
            475                 480                 485

gcg agg aag gac aat gtc atc cgg ctc tgg gaa tac ttg ctg gaa ctg     1841
Ala Arg Lys Asp Asn Val Ile Arg Leu Trp Glu Tyr Leu Leu Glu Leu
        490                 495                 500

ctc agg gcc agg agg cag cgt ctt gag atg aac ctg gga ttg caa aag     1889
Leu Arg Ala Arg Arg Gln Arg Leu Glu Met Asn Leu Gly Leu Gln Lys
    505                 510                 515

ata ttc cag gaa atg ctt tat att atg gac tgg atg gat gaa atg aag     1937
Ile Phe Gln Glu Met Leu Tyr Ile Met Asp Trp Met Asp Glu Met Lys
520                 525                 530                 535

gtg cta ttg ctg tct caa gac tat ggc aaa cac tta ctt ggt gtt gaa     1985
Val Leu Leu Leu Ser Gln Asp Tyr Gly Lys His Leu Leu Gly Val Glu
                540                 545                 550

gac ctg tta cag aag cat gcc ctg gtt gaa gca gac att gca atc caa     2033
```

-continued

```
Asp Leu Leu Gln Lys His Ala Leu Val Glu Ala Asp Ile Ala Ile Gln
            555                 560                 565

gca gag cgt gta aga ggt gtg aat gcc tct gcc cag aag ttt gca aca      2081
Ala Glu Arg Val Arg Gly Val Asn Ala Ser Ala Gln Lys Phe Ala Thr
        570                 575                 580

gat ggg gaa ggc tac aag cca tgt gac ccc cag gta att cga gac cgt      2129
Asp Gly Glu Gly Tyr Lys Pro Cys Asp Pro Gln Val Ile Arg Asp Arg
    585                 590                 595

gtt gcc cac atg gag ttc tgc tat caa gag ctt tgt cag ctg gct gcc      2177
Val Ala His Met Glu Phe Cys Tyr Gln Glu Leu Cys Gln Leu Ala Ala
600                 605                 610                 615

gag cgt agg gct cgc ctg gaa gag tcc cgt cgc ctc tgg aag ttc ttc      2225
Glu Arg Arg Ala Arg Leu Glu Glu Ser Arg Arg Leu Trp Lys Phe Phe
                620                 625                 630

tgg gag atg gca gaa gag gaa ggc tgg ata cga gag aag gaa aag atc      2273
Trp Glu Met Ala Glu Glu Glu Gly Trp Ile Arg Glu Lys Glu Lys Ile
            635                 640                 645

ctg tcc tct gat gat tac ggg aaa gac ttg acc agt gtc atg cgc ctg      2321
Leu Ser Ser Asp Asp Tyr Gly Lys Asp Leu Thr Ser Val Met Arg Leu
        650                 655                 660

ctg agc aag cac cgg gca ttt gag gat gag atg agt ggc cgt agt ggc      2369
Leu Ser Lys His Arg Ala Phe Glu Asp Glu Met Ser Gly Arg Ser Gly
    665                 670                 675

cat ttt gag cag gcc att aaa gaa ggt gaa gac atg att gca gag gaa      2417
His Phe Glu Gln Ala Ile Lys Glu Gly Glu Asp Met Ile Ala Glu Glu
680                 685                 690                 695

cac ttt gga tcg gaa aag atc cgt gag aga atc att tat atc cgg gag      2465
His Phe Gly Ser Glu Lys Ile Arg Glu Arg Ile Ile Tyr Ile Arg Glu
                700                 705                 710

cag tgg gcc aac ctg gaa cag ctc tca gcc att agg aag aag cgc cta      2513
Gln Trp Ala Asn Leu Glu Gln Leu Ser Ala Ile Arg Lys Lys Arg Leu
            715                 720                 725

gag gaa gcc tca tta ctg cac cag ttc cag gct gat gct gat gat att      2561
Glu Glu Ala Ser Leu Leu His Gln Phe Gln Ala Asp Ala Asp Asp Ile
        730                 735                 740

gat gct tgg atg tta gat ata ctc aag att gtc tcc agc aat gat gtg      2609
Asp Ala Trp Met Leu Asp Ile Leu Lys Ile Val Ser Ser Asn Asp Val
    745                 750                 755

ggc cat gat gag tac tcc acg cag tct ctg gtc aag aag cat aaa gat      2657
Gly His Asp Glu Tyr Ser Thr Gln Ser Leu Val Lys Lys His Lys Asp
760                 765                 770                 775

gta gca gaa gag atc acc aac tgc agg ccc act att gac aca ctg cat      2705
Val Ala Glu Glu Ile Thr Asn Cys Arg Pro Thr Ile Asp Thr Leu His
                780                 785                 790

gag caa gcc agt gcc ctt cca caa gca cat gca gag tct cca gat gtg      2753
Glu Gln Ala Ser Ala Leu Pro Gln Ala His Ala Glu Ser Pro Asp Val
            795                 800                 805

aag ggc cgg ctg gca gga att gag gag cgc tgc aag gag atg gca gag      2801
Lys Gly Arg Leu Ala Gly Ile Glu Glu Arg Cys Lys Glu Met Ala Glu
        810                 815                 820

tta aca cgg cta agg aag cag gct ctg cag gac acc ctg gcc ctg tac      2849
Leu Thr Arg Leu Arg Lys Gln Ala Leu Gln Asp Thr Leu Ala Leu Tyr
    825                 830                 835

aag atg ttc agt gag gct gat gcc tgt gag ctc tgg att gac gag aag      2897
Lys Met Phe Ser Glu Ala Asp Ala Cys Glu Leu Trp Ile Asp Glu Lys
840                 845                 850                 855

gag cag tgg ctc aac aac atg cag atc cca gag aag ctg gag gac ctg      2945
Glu Gln Trp Leu Asn Asn Met Gln Ile Pro Glu Lys Leu Glu Asp Leu
                860                 865                 870
```

-continued

```
gaa gtc atc cag cac aga ttt gag agc cta gaa cca gaa atg aac aac      2993
Glu Val Ile Gln His Arg Phe Glu Ser Leu Glu Pro Glu Met Asn Asn
            875                 880                 885

cag gct tcc cgg gtt gct gtg gtg aac cag att gca cgg cag ctg atg      3041
Gln Ala Ser Arg Val Ala Val Val Asn Gln Ile Ala Arg Gln Leu Met
        890                 895                 900

cac aat ggc cac ccc agt gaa aag gaa atc aga gct cag caa gac aaa      3089
His Asn Gly His Pro Ser Glu Lys Glu Ile Arg Ala Gln Gln Asp Lys
    905                 910                 915

ctc aac acg agg tgg agt cag ttc aga gaa ctg gtg gac agg aaa aag      3137
Leu Asn Thr Arg Trp Ser Gln Phe Arg Glu Leu Val Asp Arg Lys Lys
920                 925                 930                 935

gat gct ctt ctg tct gcc ctg agc atc cag aac tac cac ctc gag tgc      3185
Asp Ala Leu Leu Ser Ala Leu Ser Ile Gln Asn Tyr His Leu Glu Cys
                940                 945                 950

aat gaa acc aaa tcc tgc atc cgg gag aag acc aag gtc atc gag tct      3233
Asn Glu Thr Lys Ser Cys Ile Arg Glu Lys Thr Lys Val Ile Glu Ser
            955                 960                 965

acc caa gac ctt ggc aat gac ctg gca ggt gtc atg gcc ctg cag tgc      3281
Thr Gln Asp Leu Gly Asn Asp Leu Ala Gly Val Met Ala Leu Gln Cys
        970                 975                 980

aag ctg act ggc atg gaa cga gac ttg gta gcc att gag gcg aag ctg      3329
Lys Leu Thr Gly Met Glu Arg Asp Leu Val Ala Ile Glu Ala Lys Leu
    985                 990                 995

agt gac ctg cag aaa gaa gct gag aag ctg gag tcc gag cac cct gac      3377
Ser Asp Leu Gln Lys Glu Ala Glu Lys Leu Glu Ser Glu His Pro Asp
1000                1005                1010                1015

cag gct caa gct atc ctg tct cgg ctg gcc gag atc agt gat gtg tgg      3425
Gln Ala Gln Ala Ile Leu Ser Arg Leu Ala Glu Ile Ser Asp Val Trp
               1020                1025                1030

gag gaa atg aag aca acc ctg aag aac cga gag gcc tcc ctg gga gag      3473
Glu Glu Met Lys Thr Thr Leu Lys Asn Arg Glu Ala Ser Leu Gly Glu
           1035                1040                1045

gcc agc aag ctg cag cag ttt ctg cgg gac ttg gac gac ttc cag tct      3521
Ala Ser Lys Leu Gln Gln Phe Leu Arg Asp Leu Asp Asp Phe Gln Ser
       1050                1055                1060

tgg ctc tcc agg acc cag act gct atc gcc tca gag gac atg ccc aat      3569
Trp Leu Ser Arg Thr Gln Thr Ala Ile Ala Ser Glu Asp Met Pro Asn
   1065                1070                1075

acc ctc act gag gca gag aag ctt ctc aca cag cac gag aat atc aaa      3617
Thr Leu Thr Glu Ala Glu Lys Leu Leu Thr Gln His Glu Asn Ile Lys
1080                1085                1090                1095

aat gag atc gac aat tat gag gaa gac tac cag aag atg cgg gac atg      3665
Asn Glu Ile Asp Asn Tyr Glu Glu Asp Tyr Gln Lys Met Arg Asp Met
               1100                1105                1110

ggc gag atg gtc acc cag ggg cag act gat gcc cag tat atg ttt ctg      3713
Gly Glu Met Val Thr Gln Gly Gln Thr Asp Ala Gln Tyr Met Phe Leu
           1115                1120                1125

cgg cag cgg ctg cag gcc tta gac act ggc tgg aat gag ctc cac aaa      3761
Arg Gln Arg Leu Gln Ala Leu Asp Thr Gly Trp Asn Glu Leu His Lys
       1130                1135                1140

atg tgg gag aac agg caa aac ctc ctc tcc cag tcc cat gcc tac cag      3809
Met Trp Glu Asn Arg Gln Asn Leu Leu Ser Gln Ser His Ala Tyr Gln
   1145                1150                1155

cag ttc ctt agg gac acc aaa caa gct gaa gct ttt ctt aat aac cag      3857
Gln Phe Leu Arg Asp Thr Lys Gln Ala Glu Ala Phe Leu Asn Asn Gln
1160                1165                1170                1175

gag tat gtt ttg gct cat act gaa atg ccc acc acc ctg gaa gga gct      3905
Glu Tyr Val Leu Ala His Thr Glu Met Pro Thr Thr Leu Glu Gly Ala
               1180                1185                1190
```

-continued

```
gaa gca gcc att aaa aag cag gag gac ttc atg acc acc atg gat gcc     3953
Glu Ala Ala Ile Lys Lys Gln Glu Asp Phe Met Thr Thr Met Asp Ala
            1195                1200                1205

aac gag gag aag atc aat gct gtt gtg gag act ggc cga aga ctg gtg     4001
Asn Glu Glu Lys Ile Asn Ala Val Val Glu Thr Gly Arg Arg Leu Val
        1210                1215                1220

agc gat ggg aac atc aac tcc gac cgc atc cag gag aag gtg gac tct     4049
Ser Asp Gly Asn Ile Asn Ser Asp Arg Ile Gln Glu Lys Val Asp Ser
    1225                1230                1235

att gac gac aga cac agg aag aat cga gaa gca gcc agt gaa ctt ctg     4097
Ile Asp Asp Arg His Arg Lys Asn Arg Glu Ala Ala Ser Glu Leu Leu
1240                1245                1250                1255

atg agg tta aag gac aac cgt gat cta cag aag ttc ctg caa gat tgt     4145
Met Arg Leu Lys Asp Asn Arg Asp Leu Gln Lys Phe Leu Gln Asp Cys
                1260                1265                1270

caa gag ctg tcc ctc tgg atc aat gaa aag atg ctt aca gct caa gac     4193
Gln Glu Leu Ser Leu Trp Ile Asn Glu Lys Met Leu Thr Ala Gln Asp
            1275                1280                1285

atg tct tat gat gaa gcc aga aat ctg cac agt aaa tgg tta aag cat     4241
Met Ser Tyr Asp Glu Ala Arg Asn Leu His Ser Lys Trp Leu Lys His
        1290                1295                1300

caa gca ttt atg gcg gaa ctt gca tcc aac aaa gaa tgg ctt gac aaa     4289
Gln Ala Phe Met Ala Glu Leu Ala Ser Asn Lys Glu Trp Leu Asp Lys
    1305                1310                1315

att gag aag gaa gga atg cag ctt att tca gaa aag cca gaa aca gaa     4337
Ile Glu Lys Glu Gly Met Gln Leu Ile Ser Glu Lys Pro Glu Thr Glu
1320                1325                1330                1335

gct gtg gta aag gaa aaa ctc act ggt tta cat aaa atg tgg gaa gtc     4385
Ala Val Val Lys Glu Lys Leu Thr Gly Leu His Lys Met Trp Glu Val
                1340                1345                1350

ctt gaa tcc aca acc cag acc aag gcc cag cgg ctc ttt gat gca aat     4433
Leu Glu Ser Thr Thr Gln Thr Lys Ala Gln Arg Leu Phe Asp Ala Asn
            1355                1360                1365

aag gct gag ctt ttc aca caa agc tgc gca gat ctt gac aaa tgg cta     4481
Lys Ala Glu Leu Phe Thr Gln Ser Cys Ala Asp Leu Asp Lys Trp Leu
        1370                1375                1380

cat ggc ctg gag agc cag att caa tct gac gac tat ggc aaa gac ctt     4529
His Gly Leu Glu Ser Gln Ile Gln Ser Asp Asp Tyr Gly Lys Asp Leu
    1385                1390                1395

acc agt gtc aat att ctt ctg aaa aag caa cag atg ctg gag aat cag     4577
Thr Ser Val Asn Ile Leu Leu Lys Lys Gln Gln Met Leu Glu Asn Gln
1400                1405                1410                1415

atg gaa gtt cgg aag aaa gag atc gag gaa ctg cag agc caa gcc cag     4625
Met Glu Val Arg Lys Lys Glu Ile Glu Glu Leu Gln Ser Gln Ala Gln
                1420                1425                1430

gcg ctg agt cag gag ggg aag agc aca gat gag gtg gac agc aaa cgc     4673
Ala Leu Ser Gln Glu Gly Lys Ser Thr Asp Glu Val Asp Ser Lys Arg
            1435                1440                1445

ctt act gtg cag acc aag ttc atg gag ctt ctg gag ccc ttg agt gag     4721
Leu Thr Val Gln Thr Lys Phe Met Glu Leu Leu Glu Pro Leu Ser Glu
        1450                1455                1460

agg aag cat aac ctg tta gct tcc aag gag atc cat cag ttc aac agg     4769
Arg Lys His Asn Leu Leu Ala Ser Lys Glu Ile His Gln Phe Asn Arg
    1465                1470                1475

gat gtg gag gac gaa atc cta tgg gtt ggc gag agg atg cct ttg gca     4817
Asp Val Glu Asp Glu Ile Leu Trp Val Gly Glu Arg Met Pro Leu Ala
1480                1485                1490                1495

act tcc aca gat cat ggc cat aac ctt caa act gtg cag ctg tta ata     4865
Thr Ser Thr Asp His Gly His Asn Leu Gln Thr Val Gln Leu Leu Ile
```

-continued

```
                1500                1505                1510

aag aaa aac cag acc ctc cag aaa gaa atc cag gga cac cag cct cgt     4913
Lys Lys Asn Gln Thr Leu Gln Lys Glu Ile Gln Gly His Gln Pro Arg
            1515                1520                1525

att gat gac atc ttt gag agg agt caa aac atc atc aca gat agc agc     4961
Ile Asp Asp Ile Phe Glu Arg Ser Gln Asn Ile Ile Thr Asp Ser Ser
        1530                1535                1540

agc ctc aat gcc gag gct atc agg cag agg ctc gct gac ctg aag cag     5009
Ser Leu Asn Ala Glu Ala Ile Arg Gln Arg Leu Ala Asp Leu Lys Gln
    1545                1550                1555

ctg tgg ggg ctc ctc att gag gaa act gag aaa cgc cat aga cgg ctg     5057
Leu Trp Gly Leu Leu Ile Glu Glu Thr Glu Lys Arg His Arg Arg Leu
1560                1565                1570                1575

gag gag gca cac aag gcg cag cag tac tac ttt gat gca gct gaa gcc     5105
Glu Glu Ala His Lys Ala Gln Gln Tyr Tyr Phe Asp Ala Ala Glu Ala
                1580                1585                1590

gag gca tgg atg agt gaa cag gag ttg tac atg atg tct gag gaa aag     5153
Glu Ala Trp Met Ser Glu Gln Glu Leu Tyr Met Met Ser Glu Glu Lys
            1595                1600                1605

gcc aag gat gag cag agt gct gtc tct atg ttg aaa aag cac cag att     5201
Ala Lys Asp Glu Gln Ser Ala Val Ser Met Leu Lys Lys His Gln Ile
        1610                1615                1620

tta gag caa gct gtt gag gac tat gca gag aca gta cac cag ctc tcc     5249
Leu Glu Gln Ala Val Glu Asp Tyr Ala Glu Thr Val His Gln Leu Ser
    1625                1630                1635

aag act agc cgg gcg ctg gtg gct gac agc cat ccc gaa agt gag cgt     5297
Lys Thr Ser Arg Ala Leu Val Ala Asp Ser His Pro Glu Ser Glu Arg
1640                1645                1650                1655

att agc atg cgg cag tca aag gtc gac aag ctg tat gct ggc ctg aag     5345
Ile Ser Met Arg Gln Ser Lys Val Asp Lys Leu Tyr Ala Gly Leu Lys
                1660                1665                1670

gac ctt gct gag gag agg aga gga aaa ctt gat gag agg cac agg ctg     5393
Asp Leu Ala Glu Glu Arg Arg Gly Lys Leu Asp Glu Arg His Arg Leu
            1675                1680                1685

ttc cag ctc aac aga gag gtg gat gac ctg gaa cag tgg atc gct gag     5441
Phe Gln Leu Asn Arg Glu Val Asp Asp Leu Glu Gln Trp Ile Ala Glu
        1690                1695                1700

agg gaa gtg gtc gca ggc tcc cat gag ttg gga cag gac tat gag cat     5489
Arg Glu Val Val Ala Gly Ser His Glu Leu Gly Gln Asp Tyr Glu His
    1705                1710                1715

gtc acg atg tta caa gaa cgg ttc cga gaa ttt gct cga gac aca gga     5537
Val Thr Met Leu Gln Glu Arg Phe Arg Glu Phe Ala Arg Asp Thr Gly
1720                1725                1730                1735

aac att ggg cag gag cgt gtg gat aca gtt aat aac atg gca gat gaa     5585
Asn Ile Gly Gln Glu Arg Val Asp Thr Val Asn Asn Met Ala Asp Glu
                1740                1745                1750

ctc atc aac tct gga cat tca gat gct gcc acc att gct gag tgg aaa     5633
Leu Ile Asn Ser Gly His Ser Asp Ala Ala Thr Ile Ala Glu Trp Lys
            1755                1760                1765

gat ggt ctc aat gaa gcc tgg gct gac ctc ctg gag ctc att gac aca     5681
Asp Gly Leu Asn Glu Ala Trp Ala Asp Leu Leu Glu Leu Ile Asp Thr
        1770                1775                1780

aga aca cag att ctt gct gcc tca tat gaa ctt cat aag ttt tac cat     5729
Arg Thr Gln Ile Leu Ala Ala Ser Tyr Glu Leu His Lys Phe Tyr His
    1785                1790                1795

gat gcc aag gag atc ttt ggc cga atc cag gac aaa cac aag aaa ctc     5777
Asp Ala Lys Glu Ile Phe Gly Arg Ile Gln Asp Lys His Lys Lys Leu
1800                1805                1810                1815

cct gag gag ctt gga aga gat caa aac act gtg gaa act tta cag aga     5825
```

-continued

```
Pro Glu Glu Leu Gly Arg Asp Gln Asn Thr Val Glu Thr Leu Gln Arg
               1820                1825                1830

atg cac acc acc ttt gag cac gac atc caa gct ctg ggc act cag gtg     5873
Met His Thr Thr Phe Glu His Asp Ile Gln Ala Leu Gly Thr Gln Val
           1835                1840                1845

agg cag ctg cag gag gat gca gct cgc ctc cag gca gcc tat gca ggg     5921
Arg Gln Leu Gln Glu Asp Ala Ala Arg Leu Gln Ala Ala Tyr Ala Gly
       1850                1855                1860

gac aag gct gat gac atc cag aag cgt gag aat gag gtc ctg gaa gcc     5969
Asp Lys Ala Asp Asp Ile Gln Lys Arg Glu Asn Glu Val Leu Glu Ala
   1865                1870                1875

tgg aag tcc ctg ctg gat gct tgt gag ggt cgc agg gtg cgg ctg gta     6017
Trp Lys Ser Leu Leu Asp Ala Cys Glu Gly Arg Arg Val Arg Leu Val
1880                1885                1890                1895

gac aca gga gac aag ttc cgc ttc ttc agc atg gtg cgt gac ctc atg     6065
Asp Thr Gly Asp Lys Phe Arg Phe Phe Ser Met Val Arg Asp Leu Met
               1900                1905                1910

ctc tgg atg gaa gat gtc atc cgg cag atc gag gcc cag gag aaa cca     6113
Leu Trp Met Glu Asp Val Ile Arg Gln Ile Glu Ala Gln Glu Lys Pro
           1915                1920                1925

cgg gat gtg tca tct gtt gaa ctg tta atg aat aat cat caa ggt atc     6161
Arg Asp Val Ser Ser Val Glu Leu Leu Met Asn Asn His Gln Gly Ile
       1930                1935                1940

aaa gct gaa att gat gct cgt aat gac agc ttt aca gcc tgc att gag     6209
Lys Ala Glu Ile Asp Ala Arg Asn Asp Ser Phe Thr Ala Cys Ile Glu
   1945                1950                1955

ctt ggg aaa tcc ctg ctg gca cgg aaa cac tat gct tct gag gag atc     6257
Leu Gly Lys Ser Leu Leu Ala Arg Lys His Tyr Ala Ser Glu Glu Ile
1960                1965                1970                1975

aag gaa aag tta ctg cag ctg aca gag aaa aga aaa gaa atg att gac     6305
Lys Glu Lys Leu Leu Gln Leu Thr Glu Lys Arg Lys Glu Met Ile Asp
               1980                1985                1990

aag tgg gaa gac cgg tgg gag tgg tta aga ctg att ttg gag gtc cat     6353
Lys Trp Glu Asp Arg Trp Glu Trp Leu Arg Leu Ile Leu Glu Val His
           1995                2000                2005

cag ttc tca agg gat gcc agt gtg gca gag gct tgg ctg ctt gga cag     6401
Gln Phe Ser Arg Asp Ala Ser Val Ala Glu Ala Trp Leu Leu Gly Gln
       2010                2015                2020

gaa cca tac cta tcc agc cgt gaa att ggc cag agt gta gac gaa gtg     6449
Glu Pro Tyr Leu Ser Ser Arg Glu Ile Gly Gln Ser Val Asp Glu Val
   2025                2030                2035

gag aag ctt att aag cgc cat gag gcg ttt gaa aag tct gca gcg acc     6497
Glu Lys Leu Ile Lys Arg His Glu Ala Phe Glu Lys Ser Ala Ala Thr
2040                2045                2050                2055

tgg gat gag aga ttc tct gct ctg gaa agg ctg aca acg ttg gag cta     6545
Trp Asp Glu Arg Phe Ser Ala Leu Glu Arg Leu Thr Thr Leu Glu Leu
               2060                2065                2070

ctg gaa gtg cgc aga cag caa gag gaa gaa gaa aga aag agg cgg cca     6593
Leu Glu Val Arg Arg Gln Gln Glu Glu Glu Glu Arg Lys Arg Arg Pro
           2075                2080                2085

cct tct ccg gac cca aac acg aag gtt tca gag gag gct gag tcc cag     6641
Pro Ser Pro Asp Pro Asn Thr Lys Val Ser Glu Glu Ala Glu Ser Gln
       2090                2095                2100

caa tgg gat act tca aaa gga gac caa gtt tcc cag aat ggt ttg ccg     6689
Gln Trp Asp Thr Ser Lys Gly Asp Gln Val Ser Gln Asn Gly Leu Pro
   2105                2110                2115

gct gag cag gga tct cca cgg gtt agt tac cgc tct caa acg tac caa     6737
Ala Glu Gln Gly Ser Pro Arg Val Ser Tyr Arg Ser Gln Thr Tyr Gln
2120                2125                2130                2135
```

-continued

```
aac tac aaa aac ttt aat agc aga cgg aca gcc agt gac cat tca tgg     6785
Asn Tyr Lys Asn Phe Asn Ser Arg Arg Thr Ala Ser Asp His Ser Trp
            2140                2145                2150

tct gga atg tgaagttcac taccatttgt caagaaccac tctgtccaca            6834
Ser Gly Met

tcctttgacc ttttggcttc cacgtcaccc agagtgttaa aatttttact taattcatag   6894

ctgtccttga tttcatattt gtttgcattt aatttatgtt tctttggatc ctcattgcct   6954

caaagc                                                              6960


<210> SEQ ID NO 4
<211> LENGTH: 2154
<212> TYPE: PRT
<213> ORGANISM: Mus musculus

<400> SEQUENCE: 4

Met Glu Leu Gln Arg Thr Ser Ser Val Ser Gly Pro Leu Ser Pro Ala
  1               5                  10                  15

Tyr Thr Gly Gln Val Pro Tyr Asn Tyr Asn Gln Leu Glu Gly Arg Phe
             20                  25                  30

Lys Gln Leu Gln Asp Glu Arg Glu Ala Val Gln Lys Lys Thr Phe Thr
         35                  40                  45

Lys Trp Val Asn Ser His Leu Ala Arg Val Ser Cys Arg Ile Thr Asp
     50                  55                  60

Leu Tyr Thr Asp Leu Arg Asp Gly Arg Met Leu Ile Lys Leu Leu Glu
 65                  70                  75                  80

Val Leu Ser Gly Glu Arg Leu Pro Lys Pro Thr Lys Gly Arg Met Arg
                 85                  90                  95

Ile His Cys Leu Glu Asn Val Asp Lys Ala Leu Gln Phe Leu Lys Glu
            100                 105                 110

Gln Arg Val His Leu Glu Asn Met Gly Ser His Asp Ile Val Asp Gly
        115                 120                 125

Asn His Arg Leu Thr Leu Gly Leu Ile Trp Thr Ile Ile Leu Arg Phe
    130                 135                 140

Gln Ile Gln Asp Ile Ser Val Glu Thr Glu Asp Asn Lys Glu Lys Lys
145                 150                 155                 160

Ser Ala Lys Asp Ala Leu Leu Leu Trp Cys Gln Met Lys Thr Ala Gly
                165                 170                 175

Tyr Pro Asn Val Asn Ile His Asn Phe Thr Thr Ser Trp Arg Asp Gly
            180                 185                 190

Met Ala Phe Asn Ala Leu Ile His Lys His Arg Pro Asp Leu Ile Asp
        195                 200                 205

Phe Asp Lys Leu Lys Lys Ser Asn Ala His Tyr Asn Leu Gln Asn Ala
    210                 215                 220

Phe Asn Leu Ala Glu Gln His Leu Gly Leu Thr Lys Leu Leu Asp Pro
225                 230                 235                 240

Glu Asp Ile Ser Val Asp His Pro Asp Glu Lys Ser Ile Ile Thr Tyr
                245                 250                 255

Val Val Thr Tyr Tyr His Tyr Phe Ser Lys Met Lys Ala Leu Ala Val
            260                 265                 270

Glu Gly Lys Arg Ile Gly Lys Val Leu Asp Asn Ala Ile Glu Thr Glu
        275                 280                 285

Lys Met Ile Glu Lys Tyr Glu Thr Leu Ala Ser Asp Leu Leu Glu Trp
    290                 295                 300

Ile Glu Gln Thr Ile Ile Ile Leu Asn Asn Arg Lys Phe Ala Asn Ser
```

-continued

```
305                 310                 315                 320

Leu Val Gly Val Gln Gln Gln Leu Gln Ala Phe Asn Thr Tyr Arg Thr
                325                 330                 335

Val Glu Lys Pro Pro Lys Phe Thr Glu Lys Gly Asn Leu Glu Val Leu
            340                 345                 350

Leu Phe Ala Ile Gln Ser Lys Met Arg Ala Asn Asn Gln Lys Val Tyr
        355                 360                 365

Met Pro Arg Glu Gly Lys Leu Ile Ser Asp Ile Asn Lys Ala Trp Glu
    370                 375                 380

Arg Leu Glu Lys Ala Glu His Glu Arg Glu Leu Ala Leu Arg Asn Glu
385                 390                 395                 400

Leu Ile Arg Gln Glu Lys Leu Glu Gln Leu Ala Arg Arg Phe Asp Arg
                405                 410                 415

Lys Ala Ala Met Arg Glu Thr Trp Leu Ser Glu Asn Gln Arg Leu Val
            420                 425                 430

Ser Gln Asp Asn Phe Gly Phe Asp Leu Pro Ala Val Glu Ala Ala Thr
        435                 440                 445

Lys Lys His Glu Ala Ile Glu Thr Asp Ile Ala Ala Tyr Glu Glu Arg
    450                 455                 460

Val Gln Ala Val Val Ala Val Ala Arg Glu Leu Glu Ala Glu Asn Tyr
465                 470                 475                 480

His Asp Ile Lys Arg Ile Thr Ala Arg Lys Asp Asn Val Ile Arg Leu
                485                 490                 495

Trp Glu Tyr Leu Leu Glu Leu Leu Arg Ala Arg Arg Gln Arg Leu Glu
            500                 505                 510

Met Asn Leu Gly Leu Gln Lys Ile Phe Gln Glu Met Leu Tyr Ile Met
        515                 520                 525

Asp Trp Met Asp Glu Met Lys Val Leu Leu Leu Ser Gln Asp Tyr Gly
    530                 535                 540

Lys His Leu Leu Gly Val Glu Asp Leu Leu Gln Lys His Ala Leu Val
545                 550                 555                 560

Glu Ala Asp Ile Ala Ile Gln Ala Glu Arg Val Arg Gly Val Asn Ala
                565                 570                 575

Ser Ala Gln Lys Phe Ala Thr Asp Gly Glu Gly Tyr Lys Pro Cys Asp
            580                 585                 590

Pro Gln Val Ile Arg Asp Arg Val Ala His Met Glu Phe Cys Tyr Gln
        595                 600                 605

Glu Leu Cys Gln Leu Ala Ala Glu Arg Arg Ala Arg Leu Glu Glu Ser
    610                 615                 620

Arg Arg Leu Trp Lys Phe Phe Trp Glu Met Ala Glu Glu Glu Gly Trp
625                 630                 635                 640

Ile Arg Glu Lys Glu Lys Ile Leu Ser Ser Asp Asp Tyr Gly Lys Asp
                645                 650                 655

Leu Thr Ser Val Met Arg Leu Leu Ser Lys His Arg Ala Phe Glu Asp
            660                 665                 670

Glu Met Ser Gly Arg Ser Gly His Phe Glu Gln Ala Ile Lys Glu Gly
        675                 680                 685

Glu Asp Met Ile Ala Glu Glu His Phe Gly Ser Glu Lys Ile Arg Glu
    690                 695                 700

Arg Ile Ile Tyr Ile Arg Glu Gln Trp Ala Asn Leu Glu Gln Leu Ser
705                 710                 715                 720

Ala Ile Arg Lys Lys Arg Leu Glu Glu Ala Ser Leu Leu His Gln Phe
                725                 730                 735
```

-continued

```
Gln Ala Asp Ala Asp Asp Ile Asp Ala Trp Met Leu Asp Ile Leu Lys
            740                 745                 750

Ile Val Ser Ser Asn Asp Val Gly His Asp Glu Tyr Ser Thr Gln Ser
        755                 760                 765

Leu Val Lys Lys His Lys Asp Val Ala Glu Glu Ile Thr Asn Cys Arg
    770                 775                 780

Pro Thr Ile Asp Thr Leu His Glu Gln Ala Ser Ala Leu Pro Gln Ala
785                 790                 795                 800

His Ala Glu Ser Pro Asp Val Lys Gly Arg Leu Ala Gly Ile Glu Glu
                805                 810                 815

Arg Cys Lys Glu Met Ala Glu Leu Thr Arg Leu Arg Lys Gln Ala Leu
            820                 825                 830

Gln Asp Thr Leu Ala Leu Tyr Lys Met Phe Ser Glu Ala Asp Ala Cys
        835                 840                 845

Glu Leu Trp Ile Asp Glu Lys Glu Gln Trp Leu Asn Asn Met Gln Ile
    850                 855                 860

Pro Glu Lys Leu Glu Asp Leu Glu Val Ile Gln His Arg Phe Glu Ser
865                 870                 875                 880

Leu Glu Pro Glu Met Asn Asn Gln Ala Ser Arg Val Ala Val Val Asn
                885                 890                 895

Gln Ile Ala Arg Gln Leu Met His Asn Gly His Pro Ser Glu Lys Glu
            900                 905                 910

Ile Arg Ala Gln Gln Asp Lys Leu Asn Thr Arg Trp Ser Gln Phe Arg
        915                 920                 925

Glu Leu Val Asp Arg Lys Lys Asp Ala Leu Leu Ser Ala Leu Ser Ile
    930                 935                 940

Gln Asn Tyr His Leu Glu Cys Asn Glu Thr Lys Ser Cys Ile Arg Glu
945                 950                 955                 960

Lys Thr Lys Val Ile Glu Ser Thr Gln Asp Leu Gly Asn Asp Leu Ala
                965                 970                 975

Gly Val Met Ala Leu Gln Cys Lys Leu Thr Gly Met Glu Arg Asp Leu
            980                 985                 990

Val Ala Ile Glu Ala Lys Leu Ser Asp Leu Gln Lys Glu Ala Glu Lys
        995                 1000                1005

Leu Glu Ser Glu His Pro Asp Gln Ala Gln Ala Ile Leu Ser Arg Leu
   1010                1015                1020

Ala Glu Ile Ser Asp Val Trp Glu Glu Met Lys Thr Thr Leu Lys Asn
1025                1030                1035                1040

Arg Glu Ala Ser Leu Gly Glu Ala Ser Lys Leu Gln Gln Phe Leu Arg
               1045                1050                1055

Asp Leu Asp Asp Phe Gln Ser Trp Leu Ser Arg Thr Gln Thr Ala Ile
           1060                1065                1070

Ala Ser Glu Asp Met Pro Asn Thr Leu Thr Glu Ala Glu Lys Leu Leu
       1075                1080                1085

Thr Gln His Glu Asn Ile Lys Asn Glu Ile Asp Asn Tyr Glu Glu Asp
   1090                1095                1100

Tyr Gln Lys Met Arg Asp Met Gly Glu Met Val Thr Gln Gly Gln Thr
1105                1110                1115                1120

Asp Ala Gln Tyr Met Phe Leu Arg Gln Arg Leu Gln Ala Leu Asp Thr
               1125                1130                1135

Gly Trp Asn Glu Leu His Lys Met Trp Glu Asn Arg Gln Asn Leu Leu
           1140                1145                1150
```

-continued

```
Ser Gln Ser His Ala Tyr Gln Gln Phe Leu Arg Asp Thr Lys Gln Ala
       1155                1160                1165

Glu Ala Phe Leu Asn Asn Gln Glu Tyr Val Leu Ala His Thr Glu Met
   1170                1175                1180

Pro Thr Thr Leu Glu Gly Ala Glu Ala Ala Ile Lys Lys Gln Glu Asp
1185                1190                1195                1200

Phe Met Thr Thr Met Asp Ala Asn Glu Glu Lys Ile Asn Ala Val Val
               1205                1210                1215

Glu Thr Gly Arg Arg Leu Val Ser Asp Gly Asn Ile Asn Ser Asp Arg
           1220                1225                1230

Ile Gln Glu Lys Val Asp Ser Ile Asp Asp Arg His Arg Lys Asn Arg
       1235                1240                1245

Glu Ala Ala Ser Glu Leu Leu Met Arg Leu Lys Asp Asn Arg Asp Leu
   1250                1255                1260

Gln Lys Phe Leu Gln Asp Cys Gln Glu Leu Ser Leu Trp Ile Asn Glu
1265                1270                1275                1280

Lys Met Leu Thr Ala Gln Asp Met Ser Tyr Asp Glu Ala Arg Asn Leu
               1285                1290                1295

His Ser Lys Trp Leu Lys His Gln Ala Phe Met Ala Glu Leu Ala Ser
           1300                1305                1310

Asn Lys Glu Trp Leu Asp Lys Ile Glu Lys Glu Gly Met Gln Leu Ile
       1315                1320                1325

Ser Glu Lys Pro Glu Thr Glu Ala Val Val Lys Glu Lys Leu Thr Gly
   1330                1335                1340

Leu His Lys Met Trp Glu Val Leu Glu Ser Thr Thr Gln Thr Lys Ala
1345                1350                1355                1360

Gln Arg Leu Phe Asp Ala Asn Lys Ala Glu Leu Phe Thr Gln Ser Cys
               1365                1370                1375

Ala Asp Leu Asp Lys Trp Leu His Gly Leu Glu Ser Gln Ile Gln Ser
           1380                1385                1390

Asp Asp Tyr Gly Lys Asp Leu Thr Ser Val Asn Ile Leu Leu Lys Lys
       1395                1400                1405

Gln Gln Met Leu Glu Asn Gln Met Glu Val Arg Lys Lys Glu Ile Glu
   1410                1415                1420

Glu Leu Gln Ser Gln Ala Gln Ala Leu Ser Gln Glu Gly Lys Ser Thr
1425                1430                1435                1440

Asp Glu Val Asp Ser Lys Arg Leu Thr Val Gln Thr Lys Phe Met Glu
               1445                1450                1455

Leu Leu Glu Pro Leu Ser Glu Arg Lys His Asn Leu Leu Ala Ser Lys
           1460                1465                1470

Glu Ile His Gln Phe Asn Arg Asp Val Glu Asp Glu Ile Leu Trp Val
       1475                1480                1485

Gly Glu Arg Met Pro Leu Ala Thr Ser Thr Asp His Gly His Asn Leu
   1490                1495                1500

Gln Thr Val Gln Leu Leu Ile Lys Lys Asn Gln Thr Leu Gln Lys Glu
1505                1510                1515                1520

Ile Gln Gly His Gln Pro Arg Ile Asp Asp Ile Phe Glu Arg Ser Gln
               1525                1530                1535

Asn Ile Ile Thr Asp Ser Ser Ser Leu Asn Ala Glu Ala Ile Arg Gln
           1540                1545                1550

Arg Leu Ala Asp Leu Lys Gln Leu Trp Gly Leu Leu Ile Glu Glu Thr
       1555                1560                1565

Glu Lys Arg His Arg Arg Leu Glu Glu Ala His Lys Ala Gln Gln Tyr
```

-continued

```
        1570                1575                1580

Tyr Phe Asp Ala Ala Glu Ala Glu Ala Trp Met Ser Glu Gln Glu Leu
1585                1590                1595                1600

Tyr Met Met Ser Glu Glu Lys Ala Lys Asp Glu Gln Ser Ala Val Ser
                1605                1610                1615

Met Leu Lys Lys His Gln Ile Leu Glu Gln Ala Val Glu Asp Tyr Ala
            1620                1625                1630

Glu Thr Val His Gln Leu Ser Lys Thr Ser Arg Ala Leu Val Ala Asp
        1635                1640                1645

Ser His Pro Glu Ser Glu Arg Ile Ser Met Arg Gln Ser Lys Val Asp
    1650                1655                1660

Lys Leu Tyr Ala Gly Leu Lys Asp Leu Ala Glu Glu Arg Arg Gly Lys
1665                1670                1675                1680

Leu Asp Glu Arg His Arg Leu Phe Gln Leu Asn Arg Glu Val Asp Asp
                1685                1690                1695

Leu Glu Gln Trp Ile Ala Glu Arg Glu Val Val Ala Gly Ser His Glu
            1700                1705                1710

Leu Gly Gln Asp Tyr Glu His Val Thr Met Leu Gln Glu Arg Phe Arg
        1715                1720                1725

Glu Phe Ala Arg Asp Thr Gly Asn Ile Gly Gln Glu Arg Val Asp Thr
    1730                1735                1740

Val Asn Asn Met Ala Asp Glu Leu Ile Asn Ser Gly His Ser Asp Ala
1745                1750                1755                1760

Ala Thr Ile Ala Glu Trp Lys Asp Gly Leu Asn Glu Ala Trp Ala Asp
                1765                1770                1775

Leu Leu Glu Leu Ile Asp Thr Arg Thr Gln Ile Leu Ala Ala Ser Tyr
            1780                1785                1790

Glu Leu His Lys Phe Tyr His Asp Ala Lys Glu Ile Phe Gly Arg Ile
        1795                1800                1805

Gln Asp Lys His Lys Lys Leu Pro Glu Glu Leu Gly Arg Asp Gln Asn
    1810                1815                1820

Thr Val Glu Thr Leu Gln Arg Met His Thr Thr Phe Glu His Asp Ile
1825                1830                1835                1840

Gln Ala Leu Gly Thr Gln Val Arg Gln Leu Gln Glu Asp Ala Ala Arg
                1845                1850                1855

Leu Gln Ala Ala Tyr Ala Gly Asp Lys Ala Asp Asp Ile Gln Lys Arg
            1860                1865                1870

Glu Asn Glu Val Leu Glu Ala Trp Lys Ser Leu Leu Asp Ala Cys Glu
        1875                1880                1885

Gly Arg Arg Val Arg Leu Val Asp Thr Gly Asp Lys Phe Arg Phe Phe
    1890                1895                1900

Ser Met Val Arg Asp Leu Met Leu Trp Met Glu Asp Val Ile Arg Gln
1905                1910                1915                1920

Ile Glu Ala Gln Glu Lys Pro Arg Asp Val Ser Ser Val Glu Leu Leu
                1925                1930                1935

Met Asn Asn His Gln Gly Ile Lys Ala Glu Ile Asp Ala Arg Asn Asp
            1940                1945                1950

Ser Phe Thr Ala Cys Ile Glu Leu Gly Lys Ser Leu Leu Ala Arg Lys
        1955                1960                1965

His Tyr Ala Ser Glu Glu Ile Lys Glu Lys Leu Leu Gln Leu Thr Glu
    1970                1975                1980

Lys Arg Lys Glu Met Ile Asp Lys Trp Glu Asp Arg Trp Glu Trp Leu
1985                1990                1995                2000
```

```
Arg Leu Ile Leu Glu Val His Gln Phe Ser Arg Asp Ala Ser Val Ala
               2005                2010                2015

Glu Ala Trp Leu Leu Gly Gln Glu Pro Tyr Leu Ser Ser Arg Glu Ile
           2020                2025                2030

Gly Gln Ser Val Asp Glu Val Glu Lys Leu Ile Lys Arg His Glu Ala
       2035                2040                2045

Phe Glu Lys Ser Ala Ala Thr Trp Asp Glu Arg Phe Ser Ala Leu Glu
   2050                2055                2060

Arg Leu Thr Thr Leu Glu Leu Leu Glu Val Arg Arg Gln Gln Glu Glu
2065                2070                2075                2080

Glu Glu Arg Lys Arg Arg Pro Pro Ser Pro Asp Pro Asn Thr Lys Val
               2085                2090                2095

Ser Glu Glu Ala Glu Ser Gln Gln Trp Asp Thr Ser Lys Gly Asp Gln
           2100                2105                2110

Val Ser Gln Asn Gly Leu Pro Ala Glu Gln Gly Ser Pro Arg Val Ser
       2115                2120                2125

Tyr Arg Ser Gln Thr Tyr Gln Asn Tyr Lys Asn Phe Asn Ser Arg Arg
   2130                2135                2140

Thr Ala Ser Asp His Ser Trp Ser Gly Met
2145                2150
```

<210> SEQ ID NO 5
<211> LENGTH: 8176
<212> TYPE: DNA
<213> ORGANISM: Mus musculus

<400> SEQUENCE: 5

```
cctgcgtcct tcctcctttt cctccttccc tcctccctcc cgggtaattt atttctagct     60

tccaggcaag ggccacacaa ggaaggaaat ccacagggga ttagatgccg gggtggtaac    120

tccaccaggc taggttggac tctgcagcca acttcctatc agatcaccct gcacctattt    180

ccgacccgac cggaatgcga ctggcttgag gtccagccct ttcgcctggg cgggagcaga    240

gccgcggaag ctgcttggag ttggatgggg gtaggaaggg gctggagcgg gaatcctacg    300

atgcaactgg cctgggccta aggttgggca taatggagtt gcagaggaca tccagcgttt    360

cagggccgct gtcgccggcc tacaccgggc aggtgcctta caactacaac caactggagg    420

gaagattcaa acagctccaa gatgagcgtg aagctgtaca gaagaagacc ttcaccaagt    480

gggtcaattc ccaccttgca agagtgtcct gccgaatcac agacctgtac acggaccttc    540

gagatggacg gatgctcatc aagctactgg aggtcctctc tggagagagg ctgcctaaac    600

ccactaaggg acggatgcgg atccactgtc tggagaatgt cgacaaggct cttcaattcc    660

tgaaagagca gagagtccat cttgagaaca tgggctccca tgacattgtg gatggaaacc    720

accggctgac cctcggcctc atctggacaa ttattctgcg cttccagatc caggatatta    780

gtgtggagac tgaagataac aaagagaaaa agtctgctaa ggatgcattg ctgctgtggt    840

gccagatgaa gacagctggg taccccaatg tcaacattca caatttcacc actagctgga    900

gggatggcat ggccttcaat gcactgatac ataaacatcg gcctgacctg atagattttg    960

ataaactgaa gaaatctaat gcacactaca atctgcagaa tgcatttaac ctggcagagc   1020

agcaccttgg cctcactaaa ctgttagacc ctgaagatat cagtgtggac caccctgatg   1080

agaagtctat catcacatac gtggtgactt actaccacta cttctccaag atgaaggcct   1140

tggctgtcga aggaaagcgc attggaaagg tgcttgataa tgctatagaa acagagaaaa   1200
```

-continued

```
tgattgagaa gtacgagaca cttgcttctg accttctgga gtggattgaa caaaccatca   1260

tcatcctaaa caaccgcaaa tttgctaatt cactggttgg ggtccaacag cagctccaag   1320

cattcaacac gtaccgcaca gtggagaaac cacctaagtt tactgagaag ggaatttgg   1380

aggtgctcct tttcgcgatt cagagcaaga tgcgagcgaa taatcagaag gtctacatgc   1440

cccgcgaggg gaagctcatc tctgacatca acaaggcctg ggaaagactg gaaaaagcag   1500

aacatgagag agaactggct ctgcggaatg agctcatacg gcaggaaaaa ctggaacaac   1560

tcgcccgaag atttgatcgc aaggcagcta tgagggagac atggctgagt gaaaaccagc   1620

gtcttgtgtc tcaggacaac tttggatttg accttcccgc tgttgaggct gctaccaaaa   1680

aacacgaggc cattgagaca gacatcgctg catatgaaga acgagttcag gccgtggtgg   1740

ctgtggccag ggaacttgaa gccgagaact accatgacat caagcgcatc acagcgagga   1800

aggacaatgt catccggctc tgggaatact tgctggaact gctcagggcc aggaggcagc   1860

gtcttgagat gaacctggga ttgcaaaaga tattccagga aatgctttat attatggact   1920

ggatggatga aatgaaggtg ctattgctgt ctcaagacta tggcaaacac ttacttggtg   1980

ttgaagacct gttacagaag catgccctgg ttgaagcaga cattgcaatc caagcagagc   2040

gtgtaagagg tgtgaatgcc tctgcccaga agtttgcaac agatggggaa ggctacaagc   2100

catgtgaccc ccaggtaatt cgagaccgtg ttgcccacat ggagttctgc tatcaagagc   2160

tttgtcagct ggctgccgag cgtagggctc gcctggaaga gtcccgtcgc ctctggaagt   2220

tcttctggga gatggcagaa gaggaaggct ggatacgaga gaaggaaaag atcctgtcct   2280

ctgatgatta cgggaaagac ttgaccagtg tcatgcgcct gctgagcaag caccgggcat   2340

ttgaggatga gatgagtggc cgtagtggcc attttgagca ggccattaaa gaaggtgaag   2400

acatgattgc agaggaacac tttggatcgg aaaagatccg tgagagaatc atttatatcc   2460

gggagcagtg ggccaacctg gaacagctct cagccattag gaagaagcgc ctagaggaag   2520

cctcattact gcaccagttc caggctgatg ctgatgatat tgatgcttgg atgttagata   2580

tactcaagat tgtctccagc aatgatgtgg gccatgatga gtactccacg cagtctctgg   2640

tcaagaagca taaagatgta gcagaagaga tcaccaactg caggcccact attgacacac   2700

tgcatgagca agccagtgcc cttccacaag cacatgcaga gtctccagat gtgaagggcc   2760

ggctggcagg aattgaggag cgctgcaagg agatggcaga gttaacacgg ctaaggaagc   2820

aggctctgca ggacaccctg gccctgtaca agatgttcag tgaggctgat gcctgtgagc   2880

tctggattga cgagaaggag cagtggctca acaacatgca gatcccagag aagctggagg   2940

acctggaagt catccagcac agatttgaga gcctagaacc agaaatgaac aaccaggctt   3000

cccgggttgc tgtggtgaac cagattgcac ggcagctgat gcacaatggc caccccagtg   3060

aaaaggaaat cagagctcag caagacaaac tcaacacgag gtggagtcag ttcagagaac   3120

tggtggacag gaaaaaggat gctcttctgt ctgccctgag catccagaac taccacctcg   3180

agtgcaatga aaccaaatcc tgcatccggg agaagaccaa ggtcatcgag tctacccaag   3240

accttggcaa tgacctggca ggtgtcatgg ccctgcagtg caagctgact ggcatggaac   3300

gagacttggt agccattgag ggcgaagctga gtgacctgca gaaagaagct gagaagctgg   3360

agtccgagca ccctgaccag gctcaagcta tcctgtctcg gctggccgag atcagtgatg   3420

tgtgggagga aatgaagaca accctgaaga accgagaggc ctccctggga gaggccagca   3480

agctgcagca gtttctgcgg gacttggacg acttccagtc ttggctctcc aggacccaga   3540

ctgctatcgc ctcagaggac atgcccaata ccctcactga ggcagagaag cttctcacac   3600
```

-continued

```
agcacgagaa tatcaaaaat gagatcgaca attatgagga agactaccag aagatgcggg   3660
acatgggcga gatggtcacc caggggcaga ctgatgccca gtatatgttt ctgcggcagc   3720
ggctgcaggc cttagacact ggctggaatg agctccacaa aatgtgggag aacaggcaaa   3780
acctcctctc ccagtcccat gcctaccagc agttccttag ggacaccaaa caagctgaag   3840
cttttcttaa taaccaggag tatgttttgg ctcatactga aatgcccacc accctggaag   3900
gagctgaagc agccattaaa aagcaggagg acttcatgac caccatggat gccaacgagg   3960
agaagatcaa tgctgttgtg gagactggcc gaagactggt gagcgatggg aacatcaact   4020
ccgaccgcat ccaggagaag gtggactcta ttgacgacag acacaggaag aatcgagaag   4080
cagccagtga acttctgatg aggttaaagg acaaccgtga tctacagaag ttcctgcaag   4140
attgtcaaga gctgtccctc tggatcaatg aaaagatgct tacagctcaa gacatgtctt   4200
atgatgaagc cagaaatctg cacagtaaat ggttaaagca tcaagcattt atggcggaac   4260
ttgcatccaa caaagaatgg cttgacaaaa ttgagaagga aggaatgcag cttatttcag   4320
aaaagccaga aacagaagct gtggtaaagg aaaaactcac tggtttacat aaaatgtggg   4380
aagtccttga atccacaacc cagaccaagg cccagcggct ctttgatgca aataaggctg   4440
agcttttcac acaaagctgc gcagatcttg acaaatggct acatggcctg gagagccaga   4500
ttcaatctga cgactatggc aaagacctta ccagtgtcaa tattcttctg aaaaagcaac   4560
agatgctgga gaatcagatg gaagttcgga agaaagagat cgaggaactg cagagccaag   4620
cccaggcgct gagtcaggag gggaagagca cagatgaggt ggacagcaaa cgccttactg   4680
tgcagaccaa gttcatggag cttctggagc ccttgagtga gaggaagcat aacctgttag   4740
cttccaagga gatccatcag ttcaacaggg atgtggagga cgaaatccta tgggttggcg   4800
agaggatgcc tttggcaact tccacagatc atggccataa ccttcaaact gtgcagctgt   4860
taataaagaa aaaccagacc ctccagaaag aaatccaggg acaccagcct cgtattgatg   4920
acatctttga gaggagtcaa aacatcatca cagatagcag cagcctcaat gccgaggcta   4980
tcaggcagag gctcgctgac ctgaagcagc tgtgggggct cctcattgag gaaactgaga   5040
aacgccatag acggctggag gaggcacaca aggcgcagca gtactacttt gatgcagctg   5100
aagccgaggc atggatgagt gaacaggagt tgtacatgat gtctgaggaa aaggccaagg   5160
atgagcagag tgctgtctct atgttgaaaa agcaccagat tttagagcaa gctgttgagg   5220
actatgcaga gacagtacac cagctctcca agactagccg ggcgctggtg gctgacagcc   5280
atcccgaaag tgagcgtatt agcatgcggc agtcaaaggt cgacaagctg tatgctggcc   5340
tgaaggacct tgctgaggag aggagaggaa aacttgatga gaggcacagg ctgttccagc   5400
tcaacagaga ggtggatgac ctggaacagt ggatcgctga gagggaagtg gtcgcaggct   5460
cccatgagtt gggacaggac tatgagcatg tcacgatgtt acaagaacgg ttccgagaat   5520
ttgctcgaga cacaggaaac attgggcagg agcgtgtgga tacagttaat aacatggcag   5580
atgaactcat caactctgga cattcagatg ctgccaccat tgctgagtgg aaagatggtc   5640
tcaatgaagc ctgggctgac ctcctggagc tcattgacac aagaacacag attcttgctg   5700
cctcatatga acttcataag ttttaccatg atgccaagga gatctttggc cgaatccagg   5760
acaaacacaa gaaactccct gaggagcttg gaagagatca aaacactgtg gaaactttac   5820
agagaatgca caccaccttt gagcacgaca tccaagctct gggcactcag gtgaggcagc   5880
tgcaggagga tgcagctcgc ctccaggcag cctatgcagg ggacaaggct gatgacatcc   5940
```

-continued

```
agaagcgtga gaatgaggtc ctggaagcct ggaagtccct gctggatgct tgtgagggtc   6000

gcagggtgcg gctggtagac acaggagaca agttccgctt cttcagcatg gtgcgtgacc   6060

tcatgctctg gatggaagat gtcatccggc agatcgaggc ccaggagaaa ccacgggatg   6120

tgtcatctgt tgaactgtta atgaataatc atcaaggtat caaagctgaa attgatgctc   6180

gtaatgacag ctttacagcc tgcattgagc ttgggaaatc cctgctggca cggaaacact   6240

atgcttctga ggagatcaag gaaaagttac tgcagctgac agagaaaaga aaagaaatga   6300

ttgacaagtg ggaagaccgg tgggagtggt taagactgat tttggaggtc catcagttct   6360

caagggatgc cagtgtggca gaggcttggc tgcttggaca ggaaccatac ctatccagcc   6420

gtgaaattgg ccagagtgta gacgaagtgg agaagcttat taagcgccat gaggcgtttg   6480

aaaagtctgc agcgacctgg gatgagagat tctctgctct ggaaaggctg acaacgttgg   6540

agctactgga agtgcgcaga cagcaagagg aagaagaaag aaagaggcgg ccaccttctc   6600

cggacccaaa cacgaaggtt tcagaggagg ctgagtccca gcaatgggat acttcaaaag   6660

gagaccaagt ttcccagaat ggtttgccgg ctgagcaggg atctccacgg gttagttacc   6720

gctctcaaac gtaccaaaac tacaaaaact ttaatagcag acggacagcc agtgaccatt   6780

catggtctgg aatgtgaagt tcactaccat ttgtcaagaa ccactctgtc cacatccttt   6840

gaccttttgg cttccacgtc acccagagtg ttaaaatttt tacttaattc atagctgtcc   6900

ttgatttcat atttgtttgc atttaattta tgtttctttg gatcctcatt gcctcaaagc   6960

agcatactta atttttgttt atttattgtg agctttttac tttaagattt tacatgagta   7020

atcaaaatta aattatagca taatgaaatt agactcttaa caggtacggc acacacaagt   7080

taatagtact ctgctatagg tgctatgtta cttacaagta ttattaacct attggcttcc   7140

attgtatagt agttagtaac tatgaaaact ggtttgtaag gaaggaaacg tttactacta   7200

aggttaggcc tgcagttgct ctggaacatt ccatggagaa tgcattcatc aaacggcccg   7260

aaagaagcta cattttgttg ggaagctgga taagttttag gtgcaggacc ccaaatgttc   7320

tgagaccttt ggggccattt attactttgt acaagcccaa taatcctctc ttttctgcca   7380

agtcctcaac ccagaaatgt aggcttctgt gcaccacacg gcacagccca ctgattgctg   7440

ccaccggctc tgtcttggtc agtgttacca ctgccagcac tcaggctgtg gcagatgcca   7500

gcagctctta ccatcagtca gagtcttcag ggtgtcaagc tgttttcatt ttttaggcaa   7560

atagaacaaa agccattttg gttcatcctg atcacttgaa tgatagactc aatgccctgt   7620

gcctggcagg gagcgcttgc agaggtgtcc tagccttaga gggctacttc agtgtctcta   7680

ctgacagaaa ctcctgtatc tcaaatggat ctcgaagttc tctagtaagg agtcctaagg   7740

atgacatgta ttgggccact agcagggatt gaaaacattt taaaagaaat ccttttttctt   7800

aggagtaaaa gctggtaaaa ggggtgactt cctggttctg atcaaaacca gaccaaaccc   7860

tcatttcagc aaagccttgc aagacactcc cttgctcatt tgccatattt agatgtctta   7920

gtggagtcag agccctgttt ggtatgtgtt tttcatgcta agtctaaatt gtcttttcat   7980

ttcatgatgc atttttttctc ttttgtcagg ataacatcat atagcatctt gtttgttttt   8040

cctaatctct atgaacatat ctatctacct gtaaccgtag ataggtatct agatagatac   8100

caagctttta agctctgggc cactatgcat cattattggg tctctgcctt aaaacacatc   8160

caaatttata ttaaaa                                                   8176
```

<210> SEQ ID NO 6
<211> LENGTH: 1312

-continued

```
<212> TYPE: DNA
<213> ORGANISM: Mus musculus
<220> FEATURE:
<221> NAME/KEY: CDS
<222> LOCATION: (402)..(1061)

<400> SEQUENCE: 6

gcgctgctct gtgagctgga gcacagcgtg cttagagttg gccatattta aaatattttc      60

caataggatc ctgcgtcctt cctccttttc ctccttccct cctccctccc gggtaattta     120

tttctagctt ccaggcaagg gccacacaag gaaggaaatc cacaggggat tagatgccgg     180

ggtggtaact ccaccaggct aggttggact ctgcagccaa cttcctatca gatcaccctg     240

cacctatttc cgacccgacc ggaatgcgac tggcttgagg tccagccctt tcgcctgggc     300

gggagcagag ccgcggaagc tgcttggagt tggatggggg taggaagggg ctggagcggg     360

aatcctacgg tgcaactggc ctgggcctaa ggttgggcat a atg gag ttg cag agg     416
                                              Met Glu Leu Gln Arg
                                              1               5

aca tcc agc att tca ggg ccg ctg tcg ccg gcc tac acc ggg cag gtg       464
Thr Ser Ser Ile Ser Gly Pro Leu Ser Pro Ala Tyr Thr Gly Gln Val
                10                  15                  20

cct tac aac tac aac caa ctg gaa gga aga ttc aaa cag ctc caa gat       512
Pro Tyr Asn Tyr Asn Gln Leu Glu Gly Arg Phe Lys Gln Leu Gln Asp
            25                  30                  35

gag cgt gaa gct gta cag aag aag acc ttc acc aag tgg gtc aat tcc       560
Glu Arg Glu Ala Val Gln Lys Lys Thr Phe Thr Lys Trp Val Asn Ser
        40                  45                  50

cac ctt gcg aga gtg tcc tgc cga atc aca gac ctg tac acg gac ctt       608
His Leu Ala Arg Val Ser Cys Arg Ile Thr Asp Leu Tyr Thr Asp Leu
    55                  60                  65

cga gat gga cgg atg ctc atc aag cta ctg gag gtc ctc tct gga gag       656
Arg Asp Gly Arg Met Leu Ile Lys Leu Leu Glu Val Leu Ser Gly Glu
70                  75                  80                  85

agg ctg cct aaa ccc act aag gga cgg atg cgg atc cac tgt ctg gag       704
Arg Leu Pro Lys Pro Thr Lys Gly Arg Met Arg Ile His Cys Leu Glu
                90                  95                  100

aat gtc gac aag gct ctt caa ttc ctg aaa gag cag aga gtc cat ctt       752
Asn Val Asp Lys Ala Leu Gln Phe Leu Lys Glu Gln Arg Val His Leu
            105                 110                 115

gag aac atg ggc tcc cat gac att gtg gat gga aac cac cgg ctg aca       800
Glu Asn Met Gly Ser His Asp Ile Val Asp Gly Asn His Arg Leu Thr
        120                 125                 130

acg ttg gag cta ctg gaa gtg cgc aga cag caa gag gaa gaa gaa aga       848
Thr Leu Glu Leu Leu Glu Val Arg Arg Gln Gln Glu Glu Glu Glu Arg
    135                 140                 145

aag agg cgg cca cct tct ccg gac cca aac acg aag gtt tca gag gag       896
Lys Arg Arg Pro Pro Ser Pro Asp Pro Asn Thr Lys Val Ser Glu Glu
150                 155                 160                 165

gct gag tcc cag caa tgg gat act tca aaa gga gac caa gtt tcc cag       944
Ala Glu Ser Gln Gln Trp Asp Thr Ser Lys Gly Asp Gln Val Ser Gln
                170                 175                 180

aat ggt ttg ccg gct gag cag gga tct cca cgg gtt agt tac cgc tct       992
Asn Gly Leu Pro Ala Glu Gln Gly Ser Pro Arg Val Ser Tyr Arg Ser
            185                 190                 195

caa acg tac caa aac tac aaa aac ttt aat agc aga cgg aca gcc agt      1040
Gln Thr Tyr Gln Asn Tyr Lys Asn Phe Asn Ser Arg Arg Thr Ala Ser
        200                 205                 210

gac cat tca tgg tct gga atg tgaagttcac taccatttgt caagaaccac         1091
Asp His Ser Trp Ser Gly Met
    215                 220
```

```
tctgtccaca tcctttgacc ttttggcttc cacgtcaccc agagtgttaa aatttttact   1151

taattcatag ctgtccttga tttcatattt gtttgcattt aatttatgtt tctttggatc   1211

ctcattgcct caaagcagca tacttaattt ttgtttattt attgtgagct ttttacttta   1271

agattttaca tgagtaatca aaattaaatt atagcataat g                       1312
```

<210> SEQ ID NO 7
<211> LENGTH: 220
<212> TYPE: PRT
<213> ORGANISM: Mus musculus

<400> SEQUENCE: 7

```
Met Glu Leu Gln Arg Thr Ser Ser Ile Ser Gly Pro Leu Ser Pro Ala
1               5                   10                  15

Tyr Thr Gly Gln Val Pro Tyr Asn Tyr Asn Gln Leu Glu Gly Arg Phe
            20                  25                  30

Lys Gln Leu Gln Asp Glu Arg Glu Ala Val Gln Lys Lys Thr Phe Thr
        35                  40                  45

Lys Trp Val Asn Ser His Leu Ala Arg Val Ser Cys Arg Ile Thr Asp
    50                  55                  60

Leu Tyr Thr Asp Leu Arg Asp Gly Arg Met Leu Ile Lys Leu Leu Glu
65                  70                  75                  80

Val Leu Ser Gly Glu Arg Leu Pro Lys Pro Thr Lys Gly Arg Met Arg
                85                  90                  95

Ile His Cys Leu Glu Asn Val Asp Lys Ala Leu Gln Phe Leu Lys Glu
            100                 105                 110

Gln Arg Val His Leu Glu Asn Met Gly Ser His Asp Ile Val Asp Gly
        115                 120                 125

Asn His Arg Leu Thr Thr Leu Glu Leu Leu Glu Val Arg Arg Gln Gln
    130                 135                 140

Glu Glu Glu Glu Arg Lys Arg Arg Pro Pro Ser Pro Asp Pro Asn Thr
145                 150                 155                 160

Lys Val Ser Glu Glu Ala Glu Ser Gln Gln Trp Asp Thr Ser Lys Gly
                165                 170                 175

Asp Gln Val Ser Gln Asn Gly Leu Pro Ala Glu Gln Gly Ser Pro Arg
            180                 185                 190

Val Ser Tyr Arg Ser Gln Thr Tyr Gln Asn Tyr Lys Asn Phe Asn Ser
        195                 200                 205

Arg Arg Thr Ala Ser Asp His Ser Trp Ser Gly Met
    210                 215                 220
```

<210> SEQ ID NO 8
<211> LENGTH: 1964
<212> TYPE: DNA
<213> ORGANISM: Mus musculus
<220> FEATURE:
<221> NAME/KEY: CDS
<222> LOCATION: (322)..(1509)

<400> SEQUENCE: 8

```
ttggaacagt tacttcagtg gaggcagcag aaatgaggct agtccagact cacaggaata     60

gggttccatt ctcaagaaga tgatttaaag taattatcct ttacgcatag ttatcatcac    120

cacaaaaaaa gattccaacc ttttccacag aactattatg atttattttt atatgaatgt    180

atgtatttat tattatatga actcctataa tgatcacctt tacatattca cattttctta    240

ataattagtt tagccgcgtc cggaggtccg acagctctgc agctccgagc gcgcgactag    300
```

-continued

```
ccagaaagtt tcaggccatc c atg agc cac cag gaa agg att gcc agc cag      351
                        Met Ser His Gln Glu Arg Ile Ala Ser Gln
                         1               5                  10

agg agg aca aca gcc gaa gtc cca atg cac aga tca act gcc aat caa      399
Arg Arg Thr Thr Ala Glu Val Pro Met His Arg Ser Thr Ala Asn Gln
                15                  20                  25

agc aag agg agc cgg tca cca ttt gcc agc aca cgt cgt cgc tgg gat      447
Ser Lys Arg Ser Arg Ser Pro Phe Ala Ser Thr Arg Arg Arg Trp Asp
            30                  35                  40

gac agc gag agc tcg gga gcc agc ctg gct gtt gag agt gag gat tat      495
Asp Ser Glu Ser Ser Gly Ala Ser Leu Ala Val Glu Ser Glu Asp Tyr
        45                  50                  55

tcc agg tgg cgg gat gct gcc gat gct gag gag gct cat gcc gag ggc      543
Ser Arg Trp Arg Asp Ala Ala Asp Ala Glu Glu Ala His Ala Glu Gly
    60                  65                  70

cta gcc aga aga ggc cga ggt gag gct gcc agc agc tca gag cca agg      591
Leu Ala Arg Arg Gly Arg Gly Glu Ala Ala Ser Ser Ser Glu Pro Arg
 75                  80                  85                  90

tat gct gaa gac cag gat gcc agg agt gaa caa gcg aag gca gac aaa      639
Tyr Ala Glu Asp Gln Asp Ala Arg Ser Glu Gln Ala Lys Ala Asp Lys
                95                 100                 105

gtg cca aga cgg cgg cga acc atg gca gac cct gac ttc tgg gca tac      687
Val Pro Arg Arg Arg Arg Thr Met Ala Asp Pro Asp Phe Trp Ala Tyr
            110                 115                 120

acc gac gat tac tac cga tac tac gag gaa gat tct gac agc gac aaa      735
Thr Asp Asp Tyr Tyr Arg Tyr Tyr Glu Glu Asp Ser Asp Ser Asp Lys
        125                 130                 135

gag tgg atg gct gcc ctg cgc agg aag tac cga agc cga gag caa ccc      783
Glu Trp Met Ala Ala Leu Arg Arg Lys Tyr Arg Ser Arg Glu Gln Pro
    140                 145                 150

cag tcc tcc agc gga gaa agc tgg gag ctt ctg cca gga aag gaa gaa      831
Gln Ser Ser Ser Gly Glu Ser Trp Glu Leu Leu Pro Gly Lys Glu Glu
155                 160                 165                 170

ctg gaa cgt cag caa gcc gga gct ggg agc ctc gcc agt gct ggc agc      879
Leu Glu Arg Gln Gln Ala Gly Ala Gly Ser Leu Ala Ser Ala Gly Ser
               175                 180                 185

aat ggc agt ggt tat cct gaa gaa gta caa gac cca tct ctt cag gag      927
Asn Gly Ser Gly Tyr Pro Glu Glu Val Gln Asp Pro Ser Leu Gln Glu
            190                 195                 200

gaa gaa cag gcc tct ctg gaa gaa gga gaa atc cct tgg ctt cgc tac      975
Glu Glu Gln Ala Ser Leu Glu Glu Gly Glu Ile Pro Trp Leu Arg Tyr
        205                 210                 215

aat gag aat gaa agc agc agc gag ggt gat aat gag tct acc cat gag     1023
Asn Glu Asn Glu Ser Ser Ser Glu Gly Asp Asn Glu Ser Thr His Glu
    220                 225                 230

ctc ata cag cct ggg atg ttc atg ctg gat gga aac aac aac ctg gaa     1071
Leu Ile Gln Pro Gly Met Phe Met Leu Asp Gly Asn Asn Asn Leu Glu
235                 240                 245                 250

gat gac tcc agc gtg agc gaa gac ctc gaa gtg gac tgg agc ctg ttt     1119
Asp Asp Ser Ser Val Ser Glu Asp Leu Glu Val Asp Trp Ser Leu Phe
                255                 260                 265

gat ggg ttt gcc gat ggc ttg gga gtg gcc gaa gcc atc tcc tac gtg     1167
Asp Gly Phe Ala Asp Gly Leu Gly Val Ala Glu Ala Ile Ser Tyr Val
            270                 275                 280

gat cct cag ttc ctc acc tac atg gct ctg gaa gag cgt ctg gcc cag     1215
Asp Pro Gln Phe Leu Thr Tyr Met Ala Leu Glu Glu Arg Leu Ala Gln
        285                 290                 295

gca atg gag acg gcc ctg gca cac ttg gag tct ctc gcc gtt gat gtc     1263
Ala Met Glu Thr Ala Leu Ala His Leu Glu Ser Leu Ala Val Asp Val
```

-continued

```
    300                 305                 310

gaa gtg gcc aac cca cca gca agc aag gag agc att gat gcc ctt cct      1311
Glu Val Ala Asn Pro Pro Ala Ser Lys Glu Ser Ile Asp Ala Leu Pro
315                 320                 325                 330

gag atc ctg gtc acc gaa gat cat ggt gca gtg ggc cag gaa atg tgc      1359
Glu Ile Leu Val Thr Glu Asp His Gly Ala Val Gly Gln Glu Met Cys
                335                 340                 345

tgt cct atc tgc tgc agc gaa tat gtg aag ggg gag gtg gca act gag      1407
Cys Pro Ile Cys Cys Ser Glu Tyr Val Lys Gly Glu Val Ala Thr Glu
            350                 355                 360

cta cca tgc cac cac tat ttc cac aag ccc tgc gtg tcc atc tgg ctt      1455
Leu Pro Cys His His Tyr Phe His Lys Pro Cys Val Ser Ile Trp Leu
        365                 370                 375

cag aag tct ggc acc tgc cca gtg tgc cgc tgc atg ttc cct ccc ccg      1503
Gln Lys Ser Gly Thr Cys Pro Val Cys Arg Cys Met Phe Pro Pro Pro
    380                 385                 390

ctc taa aagccaaggc tcgtcgtaac agtcagcctg gttacattcc ctgtccgaaa      1559
Leu
395

cccacaatac tacaggagcc cttgttctaa acttacaatg aaaccagtca gtcaattaga   1619

ctaaagttgt tgattccttg tgattatttc catgtgaaaa tggttgtgta caatgacatt   1679

taaaaaaaat catcctctcg tttagaaggt agaaaggggg aaaggaaact ttctaaatgc   1739

tgcttgagat tgcagtaaga acatacattt tctaacctga aagttgaaac aaatcccact   1799

tgttctgtag actgtgtctc tcttacctgt tgctgtcagg gttacctatc tgctaaacta   1859

tgtcggaaag acaaaattac ttttgttgca tgtcatgggt taatgttcct gtatttgcag   1919

tggtgtaaaa gcttattaaa gttcttcttt tgctttgacc ccgaa                   1964


<210> SEQ ID NO 9
<211> LENGTH: 395
<212> TYPE: PRT
<213> ORGANISM: Mus musculus

<400> SEQUENCE: 9

Met Ser His Gln Glu Arg Ile Ala Ser Gln Arg Arg Thr Thr Ala Glu
  1               5                  10                  15

Val Pro Met His Arg Ser Thr Ala Asn Gln Ser Lys Arg Ser Arg Ser
             20                  25                  30

Pro Phe Ala Ser Thr Arg Arg Arg Trp Asp Asp Ser Glu Ser Ser Gly
         35                  40                  45

Ala Ser Leu Ala Val Glu Ser Glu Asp Tyr Ser Arg Trp Arg Asp Ala
     50                  55                  60

Ala Asp Ala Glu Glu Ala His Ala Glu Gly Leu Ala Arg Arg Gly Arg
 65                  70                  75                  80

Gly Glu Ala Ala Ser Ser Ser Glu Pro Arg Tyr Ala Glu Asp Gln Asp
                 85                  90                  95

Ala Arg Ser Glu Gln Ala Lys Ala Asp Lys Val Pro Arg Arg Arg Arg
            100                 105                 110

Thr Met Ala Asp Pro Asp Phe Trp Ala Tyr Thr Asp Asp Tyr Tyr Arg
        115                 120                 125

Tyr Tyr Glu Glu Asp Ser Asp Ser Asp Lys Glu Trp Met Ala Ala Leu
    130                 135                 140

Arg Arg Lys Tyr Arg Ser Arg Glu Gln Pro Gln Ser Ser Ser Gly Glu
145                 150                 155                 160

Ser Trp Glu Leu Leu Pro Gly Lys Glu Glu Leu Glu Arg Gln Gln Ala
```

-continued

```
                165                 170                 175

Gly Ala Gly Ser Leu Ala Ser Ala Gly Ser Asn Gly Ser Gly Tyr Pro
            180                 185                 190

Glu Glu Val Gln Asp Pro Ser Leu Gln Glu Glu Glu Gln Ala Ser Leu
        195                 200                 205

Glu Glu Gly Glu Ile Pro Trp Leu Arg Tyr Asn Glu Asn Glu Ser Ser
    210                 215                 220

Ser Glu Gly Asp Asn Glu Ser Thr His Glu Leu Ile Gln Pro Gly Met
225                 230                 235                 240

Phe Met Leu Asp Gly Asn Asn Asn Leu Glu Asp Asp Ser Ser Val Ser
                245                 250                 255

Glu Asp Leu Glu Val Asp Trp Ser Leu Phe Asp Gly Phe Ala Asp Gly
            260                 265                 270

Leu Gly Val Ala Glu Ala Ile Ser Tyr Val Asp Pro Gln Phe Leu Thr
        275                 280                 285

Tyr Met Ala Leu Glu Glu Arg Leu Ala Gln Ala Met Glu Thr Ala Leu
    290                 295                 300

Ala His Leu Glu Ser Leu Ala Val Asp Val Glu Val Ala Asn Pro Pro
305                 310                 315                 320

Ala Ser Lys Glu Ser Ile Asp Ala Leu Pro Glu Ile Leu Val Thr Glu
                325                 330                 335

Asp His Gly Ala Val Gly Gln Glu Met Cys Cys Pro Ile Cys Cys Ser
            340                 345                 350

Glu Tyr Val Lys Gly Glu Val Ala Thr Glu Leu Pro Cys His His Tyr
        355                 360                 365

Phe His Lys Pro Cys Val Ser Ile Trp Leu Gln Lys Ser Gly Thr Cys
    370                 375                 380

Pro Val Cys Arg Cys Met Phe Pro Pro Pro Leu
385                 390                 395


<210> SEQ ID NO 10
<211> LENGTH: 2992
<212> TYPE: DNA
<213> ORGANISM: Mus musculus

<400> SEQUENCE: 10

gggcaactga aggcagatga agagccctgc ccctgcccac atgtggaacc ttgtgctgtt      60

cttgccttca ctgttggctg tgcttccgac cactactgcc gagaagaatg gcatcgatat     120

ctacagcctc acggtggact cccgggtctc ttcccgattt gcccatactg ttgtcaccag     180

ccgggtggtc aacagagccg atgctgttca agaagcgacc ttccaagtag agctacccag     240

gaaagccttc atcaccaact tctccatgat catcgatggc gtgacctacc caggggttgt     300

caaagagaag gccgaagccc agaaacaata cagtgccgcc gtgggcaggg gagagagtgc     360

tggcatcgtc aagaccactg ggaggcagac agagaagttt gaagtgtcag tcaacgtggc     420

ccctggttcc aagattacct tcgaactcat ataccaggaa ctgctccaaa ggcgactggg     480

aatgtatgag ctactcctca aagtgaggcc tcagcagctg gtgaagcacc ttcagatgga     540

catctacatc tttgagcctc agggtattag catcctggag acagagagca ccctcatgac     600

cccggagctg gcaaatgccc ttaccacttc acagaacaag accaaggctc atatccggtt     660

caagccgacg ctctcccagc aacagaagtc tcagagtgag caggacacgg tgctgaatgg     720

ggacttcatc gtccgctatg atgtcaaccg gtctgactct gggggctcca ttcagattga     780

ggaaggctac tttgtgcacc actttgctcc agagaacctt cctacaatgt ccaagaatgt     840
```

```
gatctttgtc attgataaaa gcggatctat gtcaggcaag aaaatccagc agacccgaga    900

agccctagtc aagatcttga aagacctcag cccccaagac cagttcaacc tcattgagtt    960

cagtggggaa gcaaaccaat ggaagcagtc actggtgcaa gcgacagaag agaatttgaa   1020

caaggctgta aactatgctt ccaggatccg ggctcacgga gggaccaaca tcaataatgc   1080

agtgctgttg gctgtggagc tgctggacag aagcaaccaa gctgagctac tgccctcgaa   1140

gagcgtctcc cttatcatcc tgctcacgga cggtgacccc actgtgggag aaaccaaccc   1200

cacgattatc cagaacaacg tgcgggaagc catcaatggg cagtatagcc tcttctgcct   1260

ggggttcggc tttgatgtga actatccttt cctggagaag atggcactgg acaatggtgg   1320

cctggccagg cgcatctatg aggattcaga ctctgcactg cagcttcagg atttctacca   1380

cgaagtagcc aatccactgc tctcatcagt ggccttcgaa taccccagtg atgctgtgga   1440

ggaagtcact cggtacaagt tccaacacca ctttaagggc tcagagatgg tggtggctgg   1500

gaagctccag gaccagggtc ctgatgtcct cttagccaaa gtcagtgggc agatgcacat   1560

gcagaacatc actttccaaa cggaggccag cgtagcccaa caagagaagg agtttaagag   1620

ccccaagtac atctttcaca actttatgga gagactgtgg gcactgctga ctatacagca   1680

acagctggag cagaggattt cagcgtcagg tgccgaatta gaggccctcg aggcccaagt   1740

tctgaacttg tcactcaagt acaattttgt cacccctctc acgcacatgg tggtcaccaa   1800

acctgaaggt caagaacaat tccaagttgc tgagaagcct gtggaagtcg gtgatggcat   1860

gcagagactc cccttagcag ctcaagccca ccccttcagg cctcctgtca gaggatctaa   1920

actgatgacc gtgctgaaag gaagcaggtc ccagataccc agacgcggtg atgccgttag   1980

ggcatctagg caatacattc ctcccggatt ccccggacct cctggacctc ccggatttcc   2040

tgcacccccct ggacctcctg gatttcctgc accccctgga cctcctcttg cttctggctc   2100

tgacttcagc cttcagcctt cctatgaaag gatgctaagc ctgccctccg ttgcagcaca   2160

atatcctgct gacccacatc tggttgtgac ggaaaaaagt aaagaaagca ccataccaga   2220

ggaatcccca aacccagacc acccccaggt tcctactatt accttgccgc ttccgggatc   2280

cagtgtggac cagctctgtg tggatatctt acattctgag aagcccatga agctgttcgt   2340

agaccccagt cagggtctgg aggtgactgg taagtatgag aatactgggt tctcgtggct   2400

cgaagtgacc atccagaagc ctcacctgca ggtccatgca acccctgaac gactggtggt   2460

gacacgaggc agaaaaaaca ctgaatacaa gtggaagaag acgctgttct ctgtgttacc   2520

tggcttgaag atgaccatga atatgatggg actcctacag ctcagtggcc cagacaaagt   2580

caccatcggc ctcctgtccc tggatgaccc tcagagagga ctaatgctgc ttttgaatga   2640

cacccagcac ttctccaaca acgttaaagg ggagcttggt cagttttacc gggacatcgt   2700

ctgggagcca cccgtcgagc cagataatac aaaacggaca gtcaaagttc aaggagttga   2760

ctacctggct accagagagc tcaagttgag ttaccaagaa gggttcccag gagcagagat   2820

ttcctgctgg acagtggaga tatagaactg ttaggagcgc cgctccctgc catgttgtcc   2880

tcgtacgcag gcagatgaca ccttatgcca acagggacgc ctgtgaggcc gagaccttga   2940

tgggaagagg atgctccctt gttacaaata aagaagggca gtgtgaaccc ga           2992
```

<210> SEQ ID NO 11
<211> LENGTH: 1177
<212> TYPE: DNA
<213> ORGANISM: Mus musculus
<220> FEATURE:

<221> NAME/KEY: misc_feature
<222> LOCATION:
<223> OTHER INFORMATION: n=a or c or t or g

<400> SEQUENCE: 11

```
ggtggccaag agcagttcac ctgctctggg gcaagccttg cttgtgtttt agtgagtcag     60
ggcctcccca ggcagtaaga tgttgagtgt ggaggcccag gccgctgacc tgcagccctg    120
tcccccacag gcaggctgca tgctcttccc ccacatttct ccttgcgagg tgcgcgtgct    180
catgctcctg tactcgtcta agaagaagat cttcatgggc ctcatcccct acgaccagag    240
cggnttcgtc aacgccatac gacaggtcat caccacccgc aaacaggtgt gccagctgag    300
ggtagnctgc tcctgctcct acccttggta gacccactgn ctcccactgg tgtggaatgt    360
ggcatcaagg ctgagtcggc gnctggggag gagctgtgac gangcagtgc catacccaaa    420
tgggctcgag ggaaacntag ctttataggc ttcagagggg cagaactaga gggtggggcc    480
tgggtgtaga ggcagggcag gagtggggtg gcaggtttgg caagaggccc agagtctctg    540
gagggtcaca gtgttgatga catctttctn agaancctgc tactngctta gncagctgtg    600
gtcctctctn ccacctgggg gatacctggc nacaggcngt gggcnncggg ggtgaanact    660
ctggacctgt tnagantgtc aacaacaaat tcttgacatg gagtggtgtc atggagtggn    720
aggaggtgan ctgccgggga ctgtgtggac tgttgnccct aagctgccct cccctgaagt    780
gccttctcgc tctgccccaa aacccagacc tgagcccaac agccggtcca agaggtggct    840
gccatcccac gtctatgtga accaagggga gatcctgtga ttccgggtac ccccgggtgg    900
ccccattgac agtgccgccc ccctgggggga ggacttctga ctgatacctc ctgtcttgtg    960
tggcaggaga acagaccagt ggcctcggag gctcttcatg cagctcattc cccagcagtt   1020
gctggtgagg ggtcagggga ttccaggctg gggtgggcc aaagaccctg tggtgggctg   1080
gttcagaggc ctgcctggct tccccagcaa gctagggttc cataaagaag ccctcggcct   1140
tcccccagac caccctcgtg ccactgttcc ggaattc                            1177
```

<210> SEQ ID NO 12
<211> LENGTH: 2998
<212> TYPE: DNA
<213> ORGANISM: Mus musculus
<220> FEATURE:
<221> NAME/KEY: misc_feature
<222> LOCATION:
<223> OTHER INFORMATION: n=(a or c or t or g)

<400> SEQUENCE: 12

```
ggcacgagct taactgtgct aacttctgtg atgatcatgt gtgatgagta tgtgctctca     60
tttgatttgt gggaaaaaac aaaacaaaaa aatccgaagg acacaaagag gactaatctt    120
aaaccagata tctagtagtc accaaagcca cactttgaat tcgaaaagct tagcactgta    180
gcttagctca tgctatcttt taaagagaga atttaattat ttaatatatg gaaggacatt    240
aggctagtgt gtctggcaca tggtataaac tcaataaatg gtggacgtta tcagtgctac    300
tataatgagt ttaataattt ggtttcatct cctttaatca gaccagtgtt cactactagc    360
tgggtctctg gaataggcac agatatattc atctggagtg tcacacatac tctgtgcgcg    420
aaagagttca gaatagccct tcaataagcc aattactctt gctgtcatcc ttatttctta    480
actttccctt agcgttgctt ttatgtatca aacttttctt ccttatttta cgtaatactt    540
ttaatgacaa ctttctagaa ataagaacta taccctaaaa gattgaaata ttcttagttt    600
tctttatcta catcagaaat tgtttagctg atacaacata cttatattgt ttaaggaatt    660
```

-continued

```
ctgtttaata ccttggtatt tataattttc ataagtttat ttgtattaat aggaactctt    720
acaaagaatg tatagaaaat aagccccatc atttgtcagt gtgacaattt tcccagtgtt    780
taaattgttt aagctgtttg taccccctata taagctctgt tccttctttg gccctttccc    840
ccttagccta aatctccatt ttgcctgacg atctcttccc tgacaaaatg cctgcttctg    900
cgcactgagt cacagtctac taaaatgcat tccattgtgc ccatgtccct cttaatgtga    960
tgaccccaga catgaccagg gcagagcaca gagggagcat cactttcttt gaccagagca   1020
tctatttcca gcaatgcagc ctaaggtcac attagcattt ttggcagcaa aatacaccct   1080
tggctcatgc tgttatgctg tcaaccaaat cctccatgac tttttcacat gaactcccat   1140
taaataaggc ttcccacatc cggtacgaat atagacagta atgtgcagtc tggtgaagtt   1200
atttacataa gttcctatta aacatcagct aatctatatt tattatttta gaatattgag   1260
acagatttct attcccagct atatagatat ggttttagaa tactttatta ttattttttt   1320
aatgtgtctt ctctgaaccc gataagaaca tagtcccaga caatctttaa gttcagagtc   1380
ttacagtttg tatagagacc tagaggctag ctatatttct ttagacatca acacatcatc   1440
agataggatc cacccaaggg ccttacaaat cctgtatact gaaatgcctt ttcctgacga   1500
tattctggag actgttaagt gaatgcgcag atctgaaccg agccgagcct gtagtgggga   1560
agagctaaag catggcagtt gtcttcatca atgatggagt ctttcattat gttgtctcaa   1620
aagacacatg cttcagccct gggtctcaaa actctcatgc ttcggccctg ggtctcacac   1680
tcctggcttc ccgagtggtc atagctaaga ccttctcaca ctaaatccca ggatgagctc   1740
atgttgatgt tcctgcttgc ttctctgaaa ttggcagttc tcgtgggaaa aaaaatctac   1800
ttatacttgt gtgcttcata aagcaactcg gtagcagggc ttaggggtgc ttcgagtgtg   1860
gcagtgatag agaagaccga taaagcgaaa tctatgatat ctcatacatc attttaatta   1920
tttaaattac ttttgttagt acacaaaagt attttgttag tacaccctgt ttatctatgt   1980
gtatactcta cctttcgcat acactgactt catttctttt tctcctcacc catcctgatg   2040
agctgctctc ctcccagaca agctctggca gttttaaagt cacgtgtgta tcttttaact   2100
ctagcttctg cctattagac aaaacaagat acttgtcttt ctccccatct ccctcctttt   2160
gtttaattct cctccagccc tacatggatc ccccttgacc tcgtgtcata tatctaaatc   2220
tgtataaata aagagatgat ttaatctacg ttctatgtac aaaagagaat ataaatgctc   2280
gtctttctga atctgtctta tttggtttca cacaatatct gctctctttt accgcaaatg   2340
gtatcatctc gttcccttta cacgttgaag aaaatttcat tttgtgtgtg tgtgtgtgtg   2400
tgtgtgtgtg aactatatat ttttacgcta tctggtgagg aacatcaagg ccaagatatg   2460
gatcttggct attgtaaaga gtgtagtaag aaacacaacc gtataatcat ctctgttgca   2520
tgctggcatg ctggctacaa tcctcacctg tgtacccaga gtgagagctg gaccacatgg   2580
taatgcaacc tgtagttatt atttaatgtg tacttcttgt ttaatgttta aagatactac   2640
ttattttaat gttatgtgta tggatgtttt atctatgtgt ttgtctgtat atagtgggca   2700
cgtactggtc tcagagccag aggaaggcat cagagtccct ggggttggaa ttaaagatgt   2760
ttgtgagtac ctgcgtgtat cctggacttc aaacccgggt cttcttcaag agcagccagt   2820
gctcttaacc actgaggatc tctccagcct catcgctgat ttaggaagga cttttactga   2880
tttggagtag ctgtaggcaa tgcagtctat gacgatttcc ttttagcagt tcttgtttgt   2940
tttcttaatg atagccatac tgattgctga gatttacagc agcactagca agctggaa     2998
```

<210> SEQ ID NO 13
<211> LENGTH: 1121
<212> TYPE: DNA
<213> ORGANISM: Mus musculus
<220> FEATURE:
<221> NAME/KEY: misc_feature
<222> LOCATION:
<223> OTHER INFORMATION: n=a or c or t or g

<400> SEQUENCE: 13
ctcgagtttt tttttttttt ttttggagaa gggnaacatt tattcattca acaaatnttg 60
atgacctgat ggggnagata actgagctag tcagcgcgta ggtagcaaac ataaggntat 120
agtaccccag ntaatggtct ncccacatgt cactgaagga gtgtcagttc tcagcatttt 180
acctttaatt ttaattttta cctctaaatg cgctttagga ggctacccac agttgatgac 240
aaacagtgta gccaggcatg ccagaactgt taccagcaga acttttggcc gactgtagct 300
ggcagtgttc tcagtagtgc agttcatgcc tggtgggtgt aactagggta caacgaagtc 360
actttgaact cttttgctaa ctaaataagc caaataaaca aatcatgaaa tactgattag 420
caatgcaata tttcatggca tgggaagagc ttcgacttct ccatcggtga caaggagcag 480
cttctggaag gaaggtctgg agaaaacaac tgacggggag ctccgaggag ccctgaacac 540
gtcactcaac agcactggcg ttgacacagc tgctgtggtc cagcagtcac tcagtggaga 600
gtgccaaagg gtgggcagac agncagncct acttcttcat ctccaggatg gcacttccag 660
gcccacggtt cttagcacta cagatgttgc agtattgtgc aggagcattc atgctcggca 720
taggcaggca ctccttgtgg aacatgtgcc ggcagtggaa gaccaccacg ctgaagggct 780
tcnctgcatc tgttgggagg atgggagaaa ggcatgattc acagatattc tcttcatcaa 840
ccagaacgcc tttcatttgg gttcggngca tttttttcaca caccaacgac aatgagtcag 900
ctacgaggat tttcttgcag ccttcccgaa gcagaatctt caagttataa tcttgcagaa 960
ttttaaccaa ggaatctctc aaattgggaa tctccattcc ttccttaatt cggtggataa 1020
gtagaatcgg gtccacatgt gtgccaatgt tgttcaacaa gccagtgata aatggtggtt 1080
tgtcgatgga gtatagaatc agatcttctc gtgccgaatt c 1121

<210> SEQ ID NO 14
<211> LENGTH: 779
<212> TYPE: DNA
<213> ORGANISM: Mus musculus
<220> FEATURE:
<221> NAME/KEY: misc_feature
<222> LOCATION:
<223> OTHER INFORMATION: n=a or c or t or g

<400> SEQUENCE: 14
ctcgagagat gccccacagt ccctcaggac ccgagtcagg taatctgcct ttggccttag 60
tgacctcctt ttctgggcga gtataccatc cactttcctc cctgacaggc agttcagtaa 120
cccaaccctt tcattcctcc ttcagttgtc aaagacaact taacatccaa gactaacaag 180
caagatgact caggagcatg gnctctgggt tcccctggca ccatgcatgg tgatgctagt 240
taaggctgac ttagctctta gcaaccttgg ttgggatagc ttaagctcat ctccactttc 300
ctaccaaaca gaaaagaatt tgagtcctct tgctatgagg ctctcgctcc catctcaggc 360
gagcttcctg cccctcaccc aagcttggga ggtagagtta tggagagggc aaggaagcag 420
gactggaaag atagacttat ggatccacca ctcataaagt cacaaagtcc cctcacacct 480
gctagactta gactctaaat cattacgttg tcaccaacag aggtgactcc tcaaccacaa 540

```
gagcctgtag tgagcttcaa gagagaagag gacaagncag acctggactg catgaccttg    600

cacctgtgat gaagtcacag caataggtga tgctcaaaaa gccccaataa aatgcaagac    660

agncaaacag aagccctgtc tgtccccatt ggtgggtaat gtagctgatg tggctggttc    720

tccttccttg acttcaccct gactatggga attgtccttc agtgcctcgt gccgaattc     779
```

<210> SEQ ID NO 15
<211> LENGTH: 981
<212> TYPE: DNA
<213> ORGANISM: Mus musculus
<220> FEATURE:
<221> NAME/KEY: misc_feature
<222> LOCATION:
<223> OTHER INFORMATION: n=(a or c or t or g)

<400> SEQUENCE: 15

```
ctcgagaggt gaaggcagaa gtatcacaag ttcaagttca aggncagcct gggcttcaca     60

agacccaaaa aaataaatat gaggncagtc caggctggga ctcaggtcac tgctgtgctg    120

agccatcgtc agagaagttt cttctttnnt tttgatagga gctaacacag cgacccacan    180

ctggacagnc tgcagtgagt gagtgagtaa gtgacctaaa agtgatgtct tcattaatct    240

cccctcccca ggcntcaggg agctctgagg aagaggaggc agaaagatgg tgagagccag    300

cagggatgga ggacaccaag gaagcagtgt cttccgacac aacaggactg gcatttagga    360

agtcacagag gctgtggctg cccagggcct gcacggtcca agctggctga gattccagtg    420

ctgagagaga caattcaaca cggnctccca cccctagnca agaagttatc tccaactgat    480

atccacttgc aaaggaaaaa attagggggn tagagagatg gctcagtggn taagagcact    540

gacttanaaa atagaaatng canattngnt nngangttng cnaaatngct gagaaatggc    600

caattggctg gaaaacttgc aacattgcct ggagaactgc caaattgcct ggagagctgc    660

caaattggcc tggagagctg cctacatggc ctggagagct gcccacatgg cctggagaac    720

tggctacatg tcctggagag ctgccaacat gtcctggaga tctgcctaca tggcctggag    780

aactgcctac atgacctgga gagctggcca catggcctgg agagctggct acatgacctg    840

gagagctgnc tacatggcct ggagagctgg ctacatggcc tggagagctg gctacatggc    900

ctggagagct ggctacatgg cctggagagc tggctacatg gcctggagag cctcccagca    960

aggcctctct aagccgaatt c                                              981
```

<210> SEQ ID NO 16
<211> LENGTH: 685
<212> TYPE: DNA
<213> ORGANISM: Mus musculus
<220> FEATURE:
<221> NAME/KEY: misc_feature
<222> LOCATION:
<223> OTHER INFORMATION: n=(a or c or t or g)

<400> SEQUENCE: 16

```
ctcgagatgc attaaagctt tgntgcagaa ggatccgagt gtgtcctgtg tgtgtgtcct     60

cactggcgag accctttatc acacagggac accccttagg ttggagtttt ccttgtaatg    120

tccactatac gtctgcttta tacaataata ttgnttaaat ttgnctctat catgaaatac    180

ctcactttcc ttatctgtat tgattgaaag ttttggtgga tgtaatagtt tgggcttgga    240

tctgaagtct tttagagttt attggacatg tgcctngatt cattggnttn aaaatcntcc    300

acnacttggg ggtgtaaagg ttacccacnc nattantgga ggttcttctg agttccagag    360
```

-continued

```
anaangantg agccaccngg aattctccct aaacacactt tgatcatttc ctgcctaacc    420

ctgcagagga aatattaata ccctgtagta ccaaaggaaa caaataagaa ggaagactgn    480

tctctcatgt ctggaggaag tttggtgaag gagtcttctg tttgctcaca taggagagat    540

ctaatacagc cactatccat aattaaaaat ctctgtgaga gaggcatgac gaggttctcc    600

cagtctgtca agggatgtga atatgtgttn ccctgtcatc ctgtcatgaa gcctctcttt    660

ctctctctct cctcgtgccg aattc                                          685


<210> SEQ ID NO 17
<211> LENGTH: 471
<212> TYPE: DNA
<213> ORGANISM: Mus musculus
<220> FEATURE:
<221> NAME/KEY: misc_feature
<222> LOCATION:
<223> OTHER INFORMATION: n=(a or c or t or g)

<400> SEQUENCE: 17

gaattcngcn ttggggtaca tggaccngga gagcttggnt acatggcctg gagagctggn     60

tacatggccc ggngagctgg tttnataaac ctggggangt tgggttnaat ggccccgggg    120

angtnggttn aatanaccng gggaggtgtc tgaaaanagt ggncacgtac tgttctcaga    180

cccagnggaa gncatcagag tcccctgggg ttggaattaa agatgtttgt gagtcnctgc    240

gtgtatcctg gacttcaaac ccgggtcttc ttcaagagca gccagtgctc ttaaccactg    300

agggatctct ccagcctcat cgctgattta ggaaggactt ttactgattt ggagtanctg    360

tagccaatnc agtctatgac gatttccttt tagcagttct tgtttgtttt cttaatgata    420

gccatactga ttgctgagat ttacagcagc actagcaagc tggaactcga g             471


<210> SEQ ID NO 18
<211> LENGTH: 467
<212> TYPE: DNA
<213> ORGANISM: Mus musculus
<220> FEATURE:
<221> NAME/KEY: misc_feature
<222> LOCATION:
<223> OTHER INFORMATION: n=(a or c or t or g)

<400> SEQUENCE: 18

ctcgagnttt tttttttttt tttttttttt tttttttttt tttttttttt tttttttttt     60

tttttnnnnn aanaaaanttt taaagttttt ttttttttat naaaaannttt ccaagggggg  120

gangggttag aaganagcca nagcctggnc cccccctgcca gaaaaaaacca gaggggggtt  180

gatgtcccca agtccagttg tcaccctgaa gaagttcccc acgatttccc tggtggcccc    240

ccgggagtac gtccagagtg tcaccctttc catttgggag ctgtgggaag ggngtgggnt    300

ccctcccagn ggggccccaa acccttctcc tgaacagntc ctgatttctg accatctttc    360

caattccacg gattcaaaga gcatgaccct aggtaagcaa gccaggtcaa gagcattgct    420

tgtctgnagg aaaaggaagg gtccctcctg gcctcgtgcc gaattcc                  467


<210> SEQ ID NO 19
<211> LENGTH: 13
<212> TYPE: PRT
<213> ORGANISM: Mus musculus

<400> SEQUENCE: 19

Glu Leu Gln Arg Thr Ser Ser Val Ser Gly Pro Leu Ser
1               5                   10
```

-continued

<210> SEQ ID NO 20
<211> LENGTH: 14
<212> TYPE: PRT
<213> ORGANISM: Mus musculus

<400> SEQUENCE: 20

Phe Asn Ser Arg Arg Thr Ala Ser Asp His Ser Trp Ser Gly
1 5 10

<210> SEQ ID NO 21
<211> LENGTH: 13
<212> TYPE: PRT
<213> ORGANISM: Mus musculus

<400> SEQUENCE: 21

Leu Arg Arg Lys Tyr Arg Ser Arg Glu Gln Pro Gln Ser
1 5 10

<210> SEQ ID NO 22
<211> LENGTH: 18
<212> TYPE: PRT
<213> ORGANISM: Mus musculus

<400> SEQUENCE: 22

Ser Ala Gln Ser Leu Val Val Thr Leu Gly Arg Val Glu Gly Gly Ile
1 5 10 15

Arg Val

<210> SEQ ID NO 23
<211> LENGTH: 19
<212> TYPE: PRT
<213> ORGANISM: Mus musculus

<400> SEQUENCE: 23

Cys Ser Ala Gln Ser Leu Val Val Thr Leu Gly Arg Val Glu Gly Gly
1 5 10 15

Ile Arg Val

<210> SEQ ID NO 24
<211> LENGTH: 17
<212> TYPE: PRT
<213> ORGANISM: Mus musculus

<400> SEQUENCE: 24

Lys Ile Glu Gly Ser Ser Lys Cys Ala Pro Leu Arg Pro Ala Ser Arg
1 5 10 15

Leu

<210> SEQ ID NO 25
<211> LENGTH: 17
<212> TYPE: PRT
<213> ORGANISM: Mus musculus

<400> SEQUENCE: 25

Cys Ala Pro Leu Arg Pro Ala Ser Arg Leu Pro Ala Ser Gln Thr Leu
1 5 10 15

Gly

<210> SEQ ID NO 26
<211> LENGTH: 16
<212> TYPE: PRT
<213> ORGANISM: Mus musculus

```
<400> SEQUENCE: 26

Pro Pro Arg Glu Tyr Arg Ala Ser Gly Ser Arg Arg Gly Met Ala Tyr
1               5                   10                  15


<210> SEQ ID NO 27
<211> LENGTH: 17
<212> TYPE: PRT
<213> ORGANISM: Mus musculus

<400> SEQUENCE: 27

Pro Pro Arg Glu Tyr Arg Ala Ser Gly Ser Arg Arg Gly Met Ala Tyr
1               5                   10                  15

Cys


<210> SEQ ID NO 28
<211> LENGTH: 16
<212> TYPE: PRT
<213> ORGANISM: Mus musculus

<400> SEQUENCE: 28

Cys Lys Val Pro Arg Arg Arg Arg Thr Met Ala Asp Pro Asp Phe Trp
1               5                   10                  15
```